US006090552A

United States Patent [19]
Nazarenko et al.

[11] Patent Number: 6,090,552
[45] Date of Patent: *Jul. 18, 2000

[54] NUCLEIC ACID AMPLIFICATION OLIGONUCLEOTIDES WITH MOLECULAR ENERGY TRANSFER LABELS AND METHODS BASED THEREON

[75] Inventors: Irina A. Nazarenko; Satish K. Bhatnagar, both of Gaithersburg; Emily S. Winn-Deen, Potomac; Robert J. Hohman, Gaithersburg, all of Md.

[73] Assignee: Intergen Company, Purchase, N.Y.

[*] Notice: This patent is subject to a terminal disclaimer.

[21] Appl. No.: 08/891,516

[22] Filed: Jul. 11, 1997

Related U.S. Application Data

[63] Continuation-in-part of application No. 08/837,034, Apr. 11, 1997, which is a continuation-in-part of application No. 08/778,487, Jan. 3, 1997, Pat. No. 5,866,336, which is a continuation-in-part of application No. 08/683,667, Jul. 16, 1996, abandoned.

[51] Int. Cl.⁷ .............................. C12Q 1/68; C12P 19/34; C07H 21/04; C12N 15/00
[52] U.S. Cl. .......................... 435/6; 435/91.2; 536/24.3; 536/24.33; 536/24.32; 935/77; 935/78
[58] Field of Search ................... 435/6, 91.2; 536/24.33, 536/24.3, 25.32; 935/77, 78

[56] References Cited

U.S. PATENT DOCUMENTS

| | | | |
|---|---|---|---|
| 2,998,943 | 9/1961 | Dobbins et al. | 244/121 |
| 3,996,345 | 12/1976 | Ullman et al. | 424/8 |
| 4,160,016 | 7/1979 | Ullman | 424/8 |
| 4,174,384 | 11/1979 | Ullman et al. | 424/8 |
| 4,199,559 | 4/1980 | Ullman et al. | 424/8 |
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 4,996,143 | 2/1991 | Heller et al. | 435/6 |

(List continued on next page.)

FOREIGN PATENT DOCUMENTS

| | | | |
|---|---|---|---|
| 0 070 685 A2 | 1/1983 | European Pat. Off. | G01N 33/58 |
| 0 229 943 A2 | 7/1987 | European Pat. Off. | C12Q 1/68 |
| 628 640 A1 | 5/1994 | European Pat. Off. | C12Q 1/68 |
| 0 601 889 A2 | 6/1994 | European Pat. Off. | C12Q 1/68 |
| 0 678 582 A1 | 4/1995 | European Pat. Off. | C12Q 1/68 |
| 4-262799 | 9/1992 | Japan | C12Q 1/68 |
| 4-304900 | 10/1992 | Japan | C12Q 1/68 |
| WO 92/14845 | 9/1992 | WIPO | C12Q 1/68 |
| WO 94/17206 | 8/1994 | WIPO | C12Q 1/68 |
| WO 95/32306 | 11/1995 | WIPO | C12Q 1/16 |

OTHER PUBLICATIONS

Antequera, F. et al., 1990, "High Levels of De Novo Methylation and Altered Chromatin Structure at CpG Islands in Cell Lines", Cell 62:503–514.

(List continued on next page.)

*Primary Examiner*—Ardin H. Marschel
*Assistant Examiner*—Joyce Tung
*Attorney, Agent, or Firm*—Foley & Lardner

[57] ABSTRACT

The present invention provides labeled nucleic acid amplification oligonucleotides, which can be linear or hairpin primers or blocking oligonucleotides. The oligonucleotides of the invention are labeled with donor and/or acceptor moieties of molecular energy transfer pairs. The moieties can be fluorophores, such that fluorescent energy emitted by the donor is absorbed by the acceptor. The acceptor may be a fluorophore that fluoresces at a wavelength different from the donor moiety, or it may be a quencher. The oligonucleotides of the invention are configured so that a donor moiety and an acceptor moiety are incorporated into the amplification product. The invention also provides methods and kits for directly detecting amplification products employing the nucleic acid amplification primers. When labeled linear primers are used, treatment with exonuclease or by using specific temperature eliminates the need for separation of unincorporated primers. This "closed-tube" format greatly reduces the possibility of carryover contamination with amplification products, provides for high throughput of samples, and may be totally automated.

103 Claims, 48 Drawing Sheets

U.S. PATENT DOCUMENTS

| | | |
|---|---|---|
| 5,079,352 | 1/1992 | Gelfand et al. ............................ 536/27 |
| 5,118,801 | 6/1992 | Lizardi et al. ............................. 536/27 |
| 5,119,801 | 6/1992 | Eizenhoefer et al. .............. 128/24 EL |
| 5,312,728 | 5/1994 | Lizardi et al. ............................... 435/6 |
| 5,348,853 | 9/1994 | Wang et al. ................................. 435/6 |
| 5,391,480 | 2/1995 | Davis et al. ................................. 435/6 |
| 5,409,818 | 4/1995 | Davey et al. .......................... 435/91.2 |
| 5,487,972 | 1/1996 | Gelfand et al. ............................. 435/6 |
| 5,532,129 | 7/1996 | Heller .......................................... 435/6 |
| 5,538,871 | 7/1996 | Nuovo et al. .......................... 435/91.2 |
| 5,565,322 | 10/1996 | Heller .......................................... 435/6 |
| 5,567,583 | 10/1996 | Wang et al. ................................. 435/6 |
| 5,573,906 | 11/1996 | Bannwarth et al. ......................... 435/6 |
| 5,593,840 | 1/1997 | Bhatnagar et al. .......................... 435/6 |
| 5,607,834 | 3/1997 | Bagwell ...................................... 435/6 |
| 5,681,145 | 10/1997 | Pitner et al. ................................. 435/6 |
| 5,866,336 | 2/1999 | Nazarenko et al. ......................... 435/6 |

OTHER PUBLICATIONS

Bagasra and Seshamma, 1994, Protocol: In–Situ Amplification and Hybridization, Second Ed., John Wiley and Sons, Somerset, NJ, pp. 1–40.

Bird, A., 1992, "The Essentials of DNA Methylation", Cell 70:5–8.

Cantor, C., 1996, "Lighting Up Hybridization", Nature Biotechnology 14:264.

Cardullo, R. et al., 1988, "Detection of Nucleic Acid Hybridization by Nonradiative Fluoresence Resonance Energy Transfer", Proc. Natl. Acad. Sci. USA 85:8790–8794.

Cimino, G. et al., 1990, "Post–PCR Sterilization: A Method to Control Carryover Contamination for the Polymerase Chain Reaction", Nucleic Acids Res. 19:99–107.

Clegg, R. et al., 1993, "Observing the Helical Geometry of Double–Stranded DNA in Solution by Fluorescence Resonance Energy Transfer", Proc. Natl. Acad. Sci. USA 90:2994–2998.

Clegg, R., 1992, "Fluorescence Resonance Energy Transfer and Nucleic Acids", Methods in Enzymology 211:353–355.

Clegg, R. et al., "Fluorescence Resonance Energy Transfer Analysis of the Structure of the Four–Way DNA Junction", Biochemistry 31:4846–4856.

Clementi, M. et al., 1994, "Competitive Polymerase Chain Reaction and Analysis of Viral Activity at the Molecular Level", GATA 11:1–6.

Coghlan, A., 1996, "Brilliant Beacons Colour–Code Genes", New Scientist, p. 24.

Compton, J., 1991, "Nucleic Acid Sequence–based Amplification" Nature 350:91–92.

Cooper and Hangerman, 1990, "Analysis of Fluorescence Energy Transfer in Duplex and Branched DNA Molecules", Biochemistry 29:9261–9268.

Daubendiek and Kool, 1997, "Generation of Catalytic RNAs by Rolling Transcription of Synthetic DNA Molecules", Nature Biotechnology 15:273–277.

Dexter, D.L., 1953, "A Theory of Sensitized Luminescence in Solids", J. of Chemical Physics 21:836–850.

Förster, V.T., 1949, Z. naturforschg. 4a:321–327.

Herman, J. et al., 1996, "Methylation–specific PCR: A Novel PCR Assay for Methylation Status of CpG Islands", Proc. Natl. Acad. Sci. USA 93:9821–9826.

Holland, P. et al., 1991, "Detection of Specific Polymerase Chain Reaction Prouct by Utilizing the 5'→3' Exonuclease Activity of *Thermus acuaticus* DNA Polymerase", Proc. Natl. Acad. Sci. USA 88:7276–7280.

Ju, J. et al., 1996, "Energy Transfer Primers: A New Fluorescence labeling Paradigm for DNA Sequencing and Analysis", Nature Medicine 2:246–249.

Ju, J. et al., 1995, "Fluroescence Energy Transfer Dye–labeled Primers for DNA Sequencing and Analysis", Proc. Natl. Acad. Sci. USA 92:4347–4351.

Landegren, U., 1993, "Molecular Mechanics of Nucleic Acid Sequence Amplification", Technical Focus 9:199–204.

Lee, L. et al., 1993, "Allelic Discrimination by Nick–Translation PCR with Fluorogenic Probes", Nucleic Acids Res. 21:3761–3766.

Li, E. et al., 1993, "Role for DNA Methylation in Genomic Imprinting", Nature 366:362–365.

Li, H. et al., 1991, "Eliminating Primers from Completed Polymerase Chain Reactions with Exonuclease VII", Nucleic Acids Res. 19:3139–3141.

Liu, D. et al., 1996, "Rolling Circle DNA Synthesis: Small Circular Oligonucleotides as Efficient Templates for DNA Polymerases", J. Am. Chem. Soc. 118:1587–1594.

Longo, M. et al., 1990, "Use of Uracil DNA Glycosylase to Control Carry–over Contamination in Polymerase Chain Reactions", Gene 93:125–128.

Lyamichev, V. et al., 1993, "Structure–Specific Endonucleolytic Cleavage of Nucleic Acids by Eubacterial DNA Polymerases", Science 260:778–783.

Matayoshi, E., 1990, "Novel Fluorogenic Substrates for Assaying Retroviral Proteases by Resonance Energy Transfer", Science 247:954–958.

Morrison and Stols, 1993, "Sensitive fluorescence–Based Thermodynamic and Kinetic Measurements of DNA Hybridization in Solution", Biochemistry 32:3095–3104.

Mullis and Faloona, 1987, "Specific Synthesis of DNA in Vitro via a Polymerase–Catalyzed Chain Reaction", Methods in Enzymology 155:335–350.

Newton, C.R. et al., 1989, "Analysis of Any Point Mutation in DNA. The Amplivication Refractory Mutation System (ARMS)", Nucleic Acids Research 17:2503–2517.

Nilsson, M. et al., 1994, "Padlock Probes: Circularizing Oligonucleotides for Localized DNA Detection", Science 265:2085–2088.

Okayama, H. et al., 1989, "Rapid, Nonradioactive Detection of Mutations in the Human Genome by Allele–specific Amplification", J. Lab. Clin. Med. 114:105–113.

Orrego, 1990, in Innis et al. (eds), PCR Protocols, A Guide to Methods and Applications, Academic Press, San Diego, CA, pp. 447–454.

Ozaki and McLaughlin, 1992, "The Estimation of Distances Between Specific Backbone–labeled Sites in DNA Using Fluorescence Resonance Energy Transfer", Nucleic Acids Res. 20:5205–5214.

Pfeifer, G. et al., 1989, "Genomic Sequencing and Methylation Analysis by Ligation Mediated PCR", Science 246:810–813.

Sarin, P. et al., 1988, "Inhibition of Acquired Immunodeficiency Syndrom Virus by Oligodeoxynucleoside Methylphosphonates", Proc. Natl. Acad. Sci. USA 85:7448–7451.

Schutzbank and Smith, 1995, "Detection of Human Immunodeficiency Virus Type I Proviral DNA by PCR Using an Electrochemiluminescence–Tagged Probe", J. of Clinical Microbioloby 33:2036–2041.

Selvin, P., 1995, "Fluorescence Resonance Energy Transfer", Methods in Enzymology 246:300–334.

Siebert and Larrick, 1992, "Competitive PCR", Nature 259:557–558.

Sommer, S. et al., 1992, "PCR Amplificaiton of Specific Alleles (PASA) is a General Method for Rapidly Detecting Known Single–Base Changes", BioTechniques 12:82–87.

Stein, C.A. et al., 1988, "Physicochemical Properties of Phosphorothioate Oligodeoxynucleotides", Nucleic Acids Research 16:3209–3221.

Steinberg, I., 1971, "Long–Range Nonradiative Transfer of Electronic Excitaton Energy in Proteins and Polypeptides", Ann. Rev. Biochem. 40:81–114.

Stryer, L., 1978, "Fluorescence Energy Transfer as a Spectroscopic Ruler", Ann. Rev. Biochem. 47:819–846.

Tyagi and Kramer, 1996, "Molecular Beacons: Probes that Fluoresce upon Hybridization", Nature Biotechnology 14:303–308.

Varani, G., 1995, "Exceptionally Stable Nucleic Acid Hairpins", Annu. Rev. Biophys. Biomol. Struct. 24:379–404.

Walder, R. et al., 1993, "Use of PCR Primers Containing a 3'–terminal Ribose Residue to Prevent Cross–Contamination of Amplifice Sequences", Nucleic Acids Res. 21:4339–4343.

Walker, T., Handout from Gene Detection and Quantitation Meeting, San Diego, CA, Jun. 9–11, 1997.

Walker, G.T. et al., 1996, "Strand Displacement Amplification (SDA) and Transient–State Fluroescence Polarization Detection of *Mycobacterium Tuberculosis* DNA" Clinical Chemistry 42:9–13.

Walker and Linn, 1996, "Detection of *Mycobacterium Tuberculosis* DNA with Thermophilic Strand Displacement Amplification and Fluorescence Polarization", Clinical Chemistry 42:1604–1608.

Walker, G.T. et al., 1992, "Isothermal in Vitro Amplification of DNA by a Restriciton Enzyme/DNA Polymerase System", Proc. Natl. Acad. Sci. USA 89:392–396.

Walker, G. et al., 1992, Strand Displacement Amplification–An Isothermal, In Vitro DNA Amplification Technique, Nucleic Acids Res. 20:1691–1696.

Wang, G. et al., 1990, "Design and Synthesis of New Fluorogenic HIV Protease Substrates Based on Resonance Energy Transfer", Tetrahedron Letters 31:6493–6496.

Wang, Y. et al., 1995, "Rapid Sizing of Short Tandem Repeat Alleles Using Capillary Array Electrophoresis and Energy–Transfer Fluorescent Primers", Anal. Chem. 67:1197–1203.

Digby et al., 1989, "Human Prostate Specific Antigen (PSA) Gene: Structure and Linkage to the Kallikrein–Like Gene, hGK–1", Nucl. Acids Res. 17:2137.

Frommer et al., 1992, "A Genomic Sequencing Protocol that Yields a Positive Display of 5–Methylcytosine Residues in Individual DNA Strands", Proc. Natl. Acad. Sci. USA 89:1827–1831.

Wilson et al., 1994, "2.2 Mb of Contiguous Nucleotide Sequence from Chromosome III of C. elegans", Nature 368:32–38.

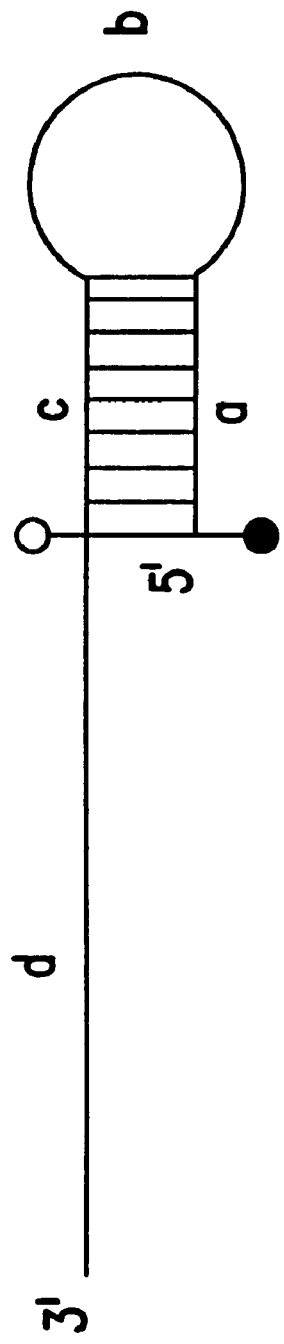
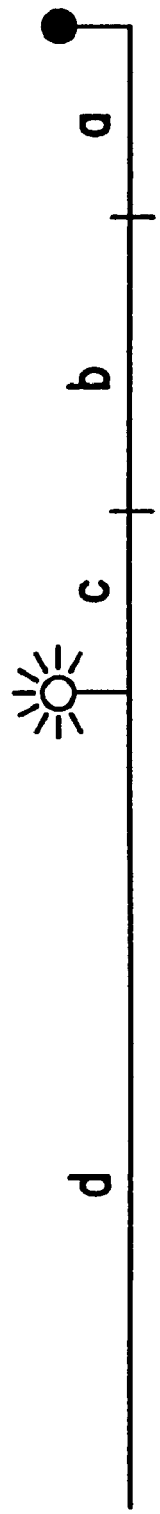
FIG.1A
FIG.1B

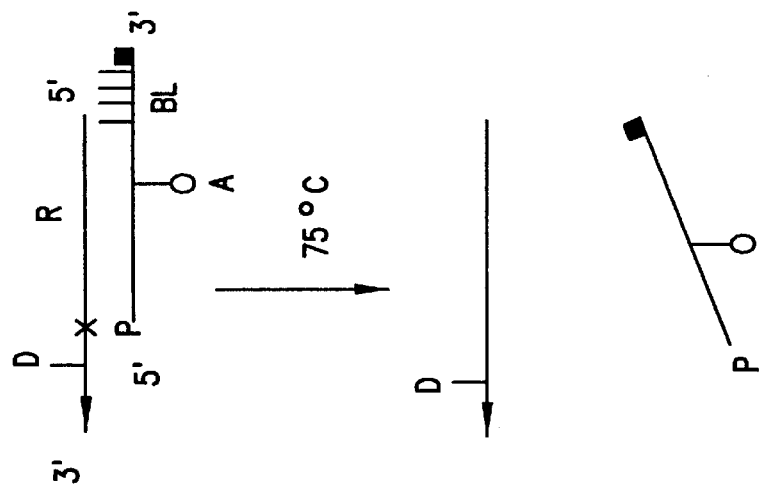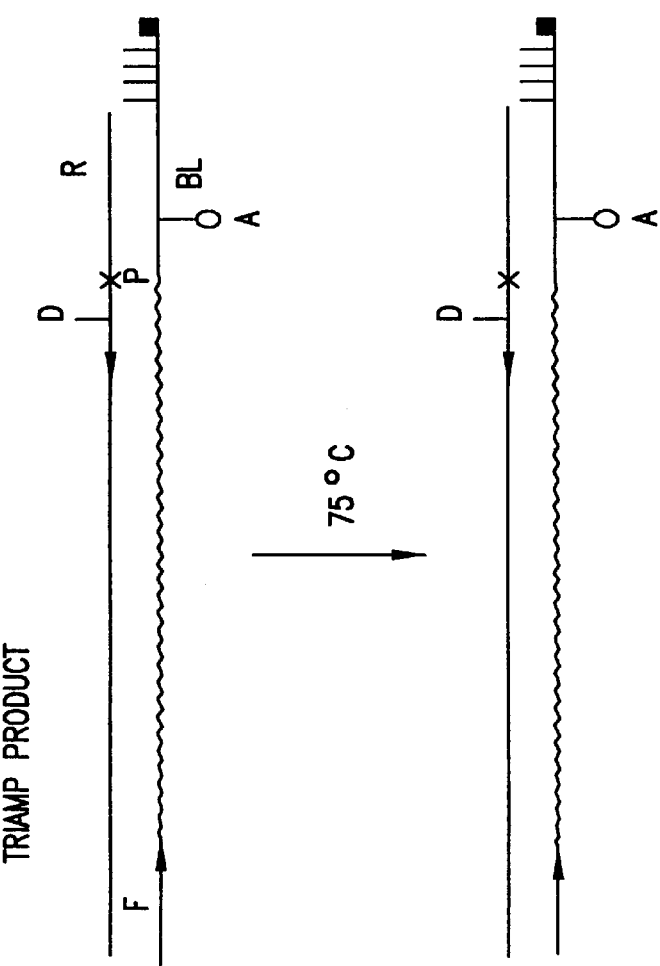
FIG. 8B

5' CTGGGGCAGCATTGAACCAGAGGAGTTCTT...CATGTGCCTGCCCGAAAGGCCTTCCCTGTACACCAAGGTG 3'
                                                    ACGGGCTTTCCGGAAGGGACATGTGG 5'
                                                              PSA-1
         PSA-P                              PSA-B
5' GCAGCATTGAACCAGAGGAGTT 3'          5' CCGAAAGGCCTTCCCTGTACACCAAAA 3'
3' GACCCCGTGTAACTTGGTCTCCTCAAGAA...GTACACGGACGGGCTTTCCGGAAGGGACATGTGGTTCCAC 5'

FIG. 12

|  | 3' SINGLE STRANDED SEQUENCE (nucl) | STEM (bp) | LOOP (bp) | FLUORESCENCE rel (%) |
|---|---|---|---|---|
| C<sup>CTC</sup> AGAAGG↓GACCAAGTTCAT3'<br>C<sub>ATA</sub> TCTTCCA<sub>f</sub> | 12 | 7 | 8 | 104 |

FIG.24E

|  | 3' SINGLE STRANDED SEQUENCE (nucl) | STEM (bp) | LOOP (bp) | FLUORESCENCE rel (%) |
|---|---|---|---|---|
| C<sup>TCA</sup> GAAGG↓GACCAAGTTCAT3'<br>C<sub>CA</sub> CTTCCA<sub>f</sub> | 11 | 7 | 7 | 108 |

FIG.24F

|  | 3' SINGLE STRANDED SEQUENCE (nucl) | STEM (bp) | LOOP (bp) | FLUORESCENCE rel (%) |
|---|---|---|---|---|
| C<sup>TC</sup> AGAAGG↓GACCAA3'<br>C<sub>CA</sub> TCTTCCA<sub>f</sub> | 6 | 7 | 6 | 5 |

FIG.24G

Uup (UPSTREAM)

5'- TGGTTATTAGAGGGTGGGGTGGATTGT -3'  (SEQ ID NO: 19)

Ud (DOWNSTREAM)
```
    T A          DAB
  A     AGTAGCTTACCCAACCCCAAACCACAACCATAA -3'   (SEQ ID NO: 20)
  G     TCATCGA
    T C          FAM
```

Mup (UPSTREAM)

5'- TTATTAGAGGGTGGGGCGGATCGC       (SEQ ID NO: 21)

Md (DOWNSTREAM)
```
    T A          DAB
  A     AGTAGCTGACCCCGAACCGCGACCGTAA -3'   (SEQ ID NO: 22)
  G     TCATCGA
    T C          FAM
```

Wup (UPSTREAM)

5'- CAGAGGGTGGGGCGGACCGC       (SEQ ID NO: 23)

Wd (DOWNSTREAM)
```
    T A          DAB
  A     AGTAGCTCCCGGGCCGCGGCCGTGG -3'   (SEQ ID NO: 24)
  G     TCATCGA
    T C          FAM
```

FIG. 26

```
         DAB
          |
ctatccagctccacctatcccagtaggagaaat-3'
g caaggtcga
          FLU-5'
```

FIG. 27

STEP 1
(ADDITION OF TELOMERIC REPEATS BY TELOMERASE)

TS-TELOMERASE PRODUCT

TELOMERIC REPEATS

5'— AATCCGTCGAGCAGAGTT ag ggttag ggttag ggttag ggttag —3'
     TS                 ag ggttag ggttag ggttag ggttag ggttag —3'
                        ag ggttag ggttag ggttag ggttag ggttag (ggttag)n —3'

FIG.29A

STEP 2
(AMPLIFICATION OF TS-TELOMERASE PRODUCT BY PCR)

| | PRIMER BINDING SITE (nucl) | STEM (bp) | LOOP (nucl) | HAIRPIN Tm's |
|---|---|---|---|---|
| ROLLING CIRCLE PRIMERS | | | | |
| 1.       C A<br>   T      T<br>   TCTGGT\*-CAGAACTGC-<u>ACTAGAGCTGAGACATGACGAGTC</u>-3'<br>   AGACCA\*-5' | 24 | 6 | 6 | 82° |
| 2.       C C<br>      T C<br>   G      G<br>   AGAACT\*-GC-<u>ACTAGAGCTGAGACATGACGAGTC</u>-3'<br>   TCTTGA\*-5'<br>   T C | 24 | 6 | 6 | 64° |
| REVERSE PRIMERS | | | | |
| 1.       T G<br>   C      C<br>   <u>GCTGAT\*CTTAGTGTCAGGATACGG</u>-3'<br>   CGACTA\*-5' | 24 | 6 | 6 | 81° |
| 2.       C A<br>      <u>C</u> <u>I</u><br>   <u>G</u>      <u>GATCT\*TAGTGTCAGGATACGG</u>-3'<br>   T      CTAGA\*-5'<br>      C T | 24 | 5 | 6 | 51° |

FIG.32A

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GCCGGTGACC AAGTTCAT                                                              18

(2) INFORMATION FOR SEQ ID NO:2:

(i) SEQUENCE CHARACTERISTICS:
        (A) LENGTH: 23 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:2:

GGCTACGAAC CAGGTAAGCC GTA                                           23

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:3:

CTGGGGCAGC ATTGAACCAG AGGAGTTCTT                                    30

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:4:

CATGTGCCTG CCCGAAAGGC CTTCCCTGTA CACCAAGGTG                         40

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GGTGTACAGG GAAGGCCTTT CGGGCA                                        26

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCAGCATTGA ACCAGAGGAG TT                                            22

(2) INFORMATION FOR SEQ ID NO:7:

(i) SEQUENCE CHARACTERISTICS:
        (A) LENGTH: 27 base pairs
        (B) TYPE: nucleic acid

```
          (C) STRANDEDNESS: single
          (D) TOPOLOGY: linear (ii) MOLECULE TYPE: DNA (genomic)

(xi) SEQUENCE DESCRIPTION: SEQ ID NO:7:

CCGAAAGGCC TTCCCTGTAC ACCAAAA                                         27

(2) INFORMATION FOR SEQ ID NO:8:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic oligonucleotide"

(xi) SEQUENCE DESCRIPTION: SEQ ID NO:8:

AAGAACTCCT CTGGTTCAAT GCTGCCCCAG                                      30

(2) INFORMATION FOR SEQ ID NO:9:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic oligonucleotide"

(xi) SEQUENCE DESCRIPTION: SEQ ID NO:9:

CACCTTGGTG TACAGGGAAG GCCTTTCGGG CAGGCACATG                            40

(2) INFORMATION FOR SEQ ID NO:10:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic oligonucleotide"

(xi) SEQUENCE DESCRIPTION: SEQ ID NO:10:

ACCTTCTACC CTCAGAAGGT GACCAAGTTC AT                                   32

(2) INFORMATION FOR SEQ ID NO:11:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic oligonucleotide"

(xi) SEQUENCE DESCRIPTION: SEQ ID NO:11:

CCCTCAGAAG GTGACCAAGT TCAT                                            24

(2) INFORMATION FOR SEQ ID NO:12:

(i) SEQUENCE CHARACTERISTICS:
          (A) LENGTH: 26 base pairs
          (B) TYPE: nucleic acid
```

(C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO:12:

GGTGTACAGG GAAGGCCTTT CGGGAC                                           26

(2) INFORMATION FOR SEQ ID NO:13:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO:13:

ACCTTCTACC CTCAGAAGGT GACCAAGTTC AT                                    32

(2) INFORMATION FOR SEQ ID NO:14:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO:14:

ACCTTCTGTT CACCCTCAGA AGGTGACCAA GTTCAT                                36

(2) INFORMATION FOR SEQ ID NO:15:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO:15:

ACCTTCGATT CACCCTCAGA AGGTGACCAA GTTCAT                                36

(2) INFORMATION FOR SEQ ID NO:16:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO:16:

ACCTTCTGTA CCCTCAGAAG GTGACCAAGT TCAT                                  34

(2) INFORMATION FOR SEQ ID NO:17:

(i) SEQUENCE CHARACTERISTICS:
            (A) LENGTH: 34 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:17:

ACCTTCTATA CCCTCAGAAG GTGACCAAGT TCAT                                    34

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:18:

CACCTTCACC CTCAGAAGGT GACCAAGTTC AT                                      32

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:19:

TGGTTATTAG AGGGTGGGGT GGATTGT                                            27

(2) INFORMATION FOR SEQ ID NO:20:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:20:

AGCTACTCTG ATAAGTAGCT TACCCAACCC CAAACCACAA CCATAA                       46

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:21:

TTATTAGAGG GTGGGGCGGA TCGC                                               24

(2) INFORMATION FOR SEQ ID NO:22:

(i) SEQUENCE CHARACTERISTICS:

(A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:22:

AGCTACTCTG ATAAGTAGCT GACCCCGAAC CGCGACCGTA A                41

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:23:

CAGAGGGTGG GGCGGACCGC                                        20

(2) INFORMATION FOR SEQ ID NO:24:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:24:

AGCTACTCTG ATAAGTAGCT CCCGGGCCGC GGCCGTGG                    38

(2) INFORMATION FOR SEQ ID NO:25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:25:

ACCTTCTACC CTCAGAAGGT GACCAA                                 26

(2) INFORMATION FOR SEQ ID NO:26:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:26:

AGCTGGAACG CTATCCAGCT CCACCTATCC CAGTAGGAGA AAT              43

(2) INFORMATION FOR SEQ ID NO:27:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO:27:

AGGGTTAGGG TTAGGGTTAG GGTTAGGGTT AGGGTTAG                                    38

(2) INFORMATION FOR SEQ ID NO:28:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO:28:

AATCCGTCGA GCAGAGTT                                                         18

(2) INFORMATION FOR SEQ ID NO:29:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO:29:

ACGCAATGTA TGCGTGG                                                          17

(2) INFORMATION FOR SEQ ID NO:30:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(xi) SEQUENCE DESCRIPTION: SEQ ID NO:30:

AGCTGGAACG CTATCCAGCT CCTGCAGGCT GAGGT                                      35

(2) INFORMATION FOR SEQ ID NO:31:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:31:

GGTGTACAGG GAAGGCCTTT CGGGAC                                                26

(2) INFORMATION FOR SEQ ID NO:32:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:32:

CCTGCAGGCT GAGGTGAAGG TGACCAAGTT CAT                                33

(2) INFORMATION FOR SEQ ID NO:33:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:33:

GTACTAGAGG ACTTACCTCT TCCC                                         24

(2) INFORMATION FOR SEQ ID NO:34:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:34:

CCTGCAGGCT GAGGTCTGTA ACAACAAGTC AGGTT                              35

(2) INFORMATION FOR SEQ ID NO:35:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:35:

CAGAGGGTGG GGCGGACCGC                                              20

(2) INFORMATION FOR SEQ ID NO:36:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:36:

CCTGCAGGCT GAGGTCCCGG GCCGCGGCCG TGG                                33

(2) INFORMATION FOR SEQ ID NO:37:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(xi) SEQUENCE DESCRIPTION: SEQ ID NO:37:

ACGCAATGTA TGCGTGGCTT ACCCTTACCC TTACCCTAAC C                          41

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

TGCTGGTCAT CGTGGCCATC GCCTGGA                                          27

(2) INFORMATION FOR SEQ ID NO:39:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

TGCTGGTCAT CGTGGCCATC GCCCGGA                                          27

(2) INFORMATION FOR SEQ ID NO:40:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:40:

ACGATGACTG ACGGTCATCG TGGTCATCGT GGCCATCGCC T                          41

(2) INFORMATION FOR SEQ ID NO:41:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:41:

ACGATGACTG ACGGTCATCG TGGTCATCGT GGCCATCGCC C                          41

(2) INFORMATION FOR SEQ ID NO:42:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:42:

CCACTACCCT GAGGACCACC                                                    20

(2) INFORMATION FOR SEQ ID NO:43:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:43:

ATAATCCACC TATCCCAGTA GGAGAAAT                                           28

(2) INFORMATION FOR SEQ ID NO:44:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:44:

TTTGGTCCTT GTCTTATGTC CAGAATGC                                           28

(2) INFORMATION FOR SEQ ID NO:45:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "hybridization probe"

(xi) SEQUENCE DESCRIPTION: SEQ ID NO:45:

ATCCTGGGAT TAAATAAAAT AGTAAGAATG TATAGCCCTA C                            41

(2) INFORMATION FOR SEQ ID NO:46:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:46:

ACCAGACCTT CATCTGGTCA GAACTGCACT AGAGCTGAGA CATGACGAGT C                 51

(2) INFORMATION FOR SEQ ID NO:47:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:47:

AGTTCTCTGG TCAGAACTGC ACTAGAGCTG AGACATGACG AGTC                        44

(2) INFORMATION FOR SEQ ID NO:48:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:48:

ATCAGCACCC TGGCTGATCT TAGTGTCAGG ATACGG                                 36

(2) INFORMATION FOR SEQ ID NO:49:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:49:

AGATCTCTGC TGATCTTAGT GTCAGGATAC GG                                     32

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:50:

ACTAGAGCTG AGACATGACG AGTC                                              24

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:51:

GCTGATCTTA GTGTCAGGAT ACGG                                              24

(2) INFORMATION FOR SEQ ID NO:52:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

TGTAGCCGTA GTTAGGCCAC CACTTCAAGA ACTCT                                      35

(2) INFORMATION FOR SEQ ID NO:53:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

GTTGGAGCTG GTGGCGTAG                                                        19

NUCLEIC ACID AMPLIFICATION OLIGONUCLEOTIDES WITH MOLECULAR ENERGY TRANSFER LABELS AND METHODS BASED THEREON

This application is a continuation-in-part of application Ser. No. 08/837,034 filed Apr. 11, 1997, which in turn is a continuation-in-part of application Ser. No. 08/778,487 filed Jan. 3, 1997, now U.S. Pat. No. 5,886,336 which in turn is a continuation-in-part of application Ser. No. 08/683,667 filed Jul. 16, 1996, now abandoned each of which is incorporated by reference herein in its entirety.

1. INTRODUCTION

The present invention relates to oligonucleotides for amplification of nucleic acids that are detectably labeled with molecular energy transfer (MET) labels. It also relates to methods for detecting the products of nucleic acid amplification using these oligonucleotides. It further relates to a rapid, sensitive, and reliable method for detecting amplification products that greatly decreases the possibility of carryover contamination with amplification products and that is adaptable to many methods for amplification of nucleic acid sequences, including polymerase chain reaction (PCR), triamplification, and other amplification systems.

2. BACKGROUND OF THE INVENTION
2.1. FLUORESCENCE RESONANCE ENERGY TRANSFER (FRET)

Molecular energy transfer (MET) is a process by which energy is passed non-radiatively between a donor molecule and an acceptor molecule. Fluorescence resonance energy transfer (FRET) is a form of MET. FRET arises from the properties of certain chemical compounds; when excited by exposure to particular wavelengths of light, they emit light (i.e., they fluoresce) at a different wavelength. Such compounds are termed fluorophores. In FRET, energy is passed non-radiatively over a long distance (10–100 Å) between a donor molecule, which is a fluorophore, and an acceptor molecule. The donor absorbs a photon and transfers this energy nonradiatively to the acceptor (Förster, 1949, Z. Naturforsch. A4:321–327; Clegg, 1992, Methods Enzymol. 211: 353–388).

When two fluorophores whose excitation and emission spectra overlap are in close proximity, excitation of one fluorophore will cause it to emit light at wavelengths that are absorbed by and that stimulate the second fluorophore, causing it in turn to fluoresce. In other words, the excited-state energy of the first (donor) fluorophore is transferred by a resonance induced dipole—dipole interaction to the neighboring second (acceptor) fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher.

Pairs of molecules that can engage in fluorescence resonance energy transfer (FRET) are termed FRET pairs. In order for energy transfer to occur, the donor and acceptor molecules must typically be in close proximity (up to 70 to 100 Å)(Clegg, 1992, Methods Enzymol. 211: 353–388; Selvin, 1995, Methods Enzymol. 246: 300–334). The efficiency of energy transfer falls off rapidly with the distance between the donor and acceptor molecules. According to Förster (1949, Z. Naturforsch. A4:321–327), the efficiency of energy transfer is proportional to $D \times 10^{-6}$, where D is the distance between the donor and acceptor. Effectively, this means that FRET can most efficiently occur up to distances of about 70 Å.

Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

In the 1970's, FRET labels were incorporated into immunofluorescent assays used to detect specific antigens (Ullman et al. U.S. Pat. Nos. 2,998,943; 3,996,345; 4,160,016; 4,174,384; and 4,199,559). Later, in the early 1980's, several patents were received by Heller and coworkers concerning the application of energy transfer for polynucleotide hybridization (U.S. Pat. Nos. 4,996,143, 5,532,129, and 5,565,322). In European Patent Application 82303699.1 (publication number EP 0 070 685 A2 dated Jan. 26, 1983), "Homogeneous nucleic acid hybridization diagnostics by non-radioactive energy transfer," the inventors claim that they can detect a unique single stranded polynucleotide sequence with two oligonucleotides: one containing the donor fluorophore, the other, an acceptor. When both oligonucleotides hybridize to adjacent fragments of analyzed DNA at a certain distance, energy transfer can be detected.

In European Patent Application 86116652.8 (publication number EP 0 229 943 A2 dated Jul. 29, 1987; "EP '943"), entitled "Fluorescent Stokes shift probes for polynucleotide hybridization assays," Heller et al. propose the same schema, but with specified distances between donor and acceptor for maximum FRET. They also disclose that the donor and acceptor labels can be located on the same probe (see, e.g., EP '943: Claim 2 and FIG. 1).

A similar application of energy transfer was disclosed by Cardullo et al. in a method of detecting nucleic acid hybridization (1988, Proc. Natl. Acad. Sci. USA 85: 8790–8794). Fluorescein (donor) and rhodamine (acceptor) are attached to 5' ends of complementary oligodeoxynucleotides. Upon hybridization, FRET may be detected. In other experiments, FRET occurred after hybridization of two fluorophore-labeled oligonucleotides to a longer unlabeled DNA. This system is the subject of U.S. patent application Ser. No. 661,071, and PCT Application PCT/US92/1591, Publication No. WO 92/14845 dated Sep. 3, 1992 ("PCT '845," entitled "Diagnosing cystic fibrosis and other genetic diseases using fluorescence resonance energy transfer"). PCT '845 discloses a method for detection of abnormalities in human chromosomal DNA associated with cystic fibrosis by hybridization. The FRET signal used in this method is generated in a manner similar to that disclosed by Heller et al. (see PCT '845 FIG. 1). Other publications have disclosed the use of energy transfer in a method for the estimation of distances between specific sites in DNA (Ozaki and McLaughlin, 1992, Nucl. Acids Res. 20: 5205–5214), in a method for the analysis of structure of four way DNA junction (Clegg et al. 1992, Biochem. 31: 4846–4856), and in a method for observing the helical geometry of DNA (Clegg et al., 1993, Proc. Natl. Acad. Sci. USA 90: 2994–2998).

2.2. OTHER TYPES OF MOLECULAR ENERGY TRANSFER (MET)

As described in Section 2.1, fluorescence resonance energy transfer (FRET) is one form of molecular energy transfer (MET). In FRET, the energy donor is fluorescent, but the energy acceptor may be fluorescent or non-fluorescent. In the case of a fluorescent energy acceptor, energy transfer results in a decrease in the emission of the donor or an increase in emission of the acceptor (Clegg, 1992, Methods Enzymol. 211: 353–388; Selvin, 1995, Methods Enzymol. 246: 300–334; Stryer, 1978, Ann. Rev. Biochem. 47:819–846). In the case of a non-fluorescent acceptor, e.g., a chromophore or a quencher, energy transfer results in an increase in the emission of the donor (Matayoshi, et al., 1990, Science 247: 954–958; Tyagi and Kramer, 1996, Nature Biotech. 14:303–309; Steinberg, 1991, Ann. Rev. Biochem. 40:83–114).

In another form of MET, the energy donor is non-fluorescent, e.g., a chromophore, and the energy acceptor is fluorescent. In this case, energy transfer results in an increase in the emission of the acceptor (Heller, U.S. Pat. Nos. 5,532,129 and 5,565,322; Steinberg, 1991, Ann. Rev. Biochem. 40:83–114).

In yet another form of MET, the energy donor is luminescent, e.g. bioluminescent, chemiluminescent, electrochemiluminescent, and the acceptor is fluorescent. In this case, energy transfer results in an increase in the emission of the acceptor (Selvin, 1995, Methods Enzymol. 246: 300–334, Heller European Patent Publication 0070685A2, dated Jan. 26, 1993; Schutzbank and Smith, 1995, J. Clin. Microbiol. 33:2036–2041). An example of such an energy transfer system is described by Selvin (supra), wherein a luminescent lanthanide chelate, e.g., terbium chelate or lanthanide chelate, is the donor, and an organic dye such as fluorescein, rhodamine or CY-5, is the acceptor. Particularly efficient MET systems using this strategy include terbium as a donor and fluorescein or rhodamine as an acceptor, and europium as a donor and CY-5 as an acceptor. The reverse situation, i.e., wherein the donor is fluorescent and the acceptor is luminescent, is termed "sensitized luminescence," and energy transfer results in an increase in emission of the acceptor (Dexter, 1953, J. Chem. Physics 21: 836–850).

In a theoretically possible form of MET, the energy donor may be luminescent and the energy acceptor may be non-fluorescent. Energy transfer results in a decrease in the emission of the donor.

2.3. METHODS OF MONITORING NUCLEIC ACID AMPLIFICATION

Prior to the present invention, application of energy transfer to the direct detection of genetic amplification products had not been attempted. In prior art methods of monitoring amplification reactions using energy transfer, a label is not incorporated into the amplification product. As a result, these methods have relied on indirect measurement of the amplification reaction.

Commonly used methods for detecting nucleic acid amplification products require that the amplified product be separated from unreacted primers. This is commonly achieved either through the use of gel electrophoresis, which separates the amplification product from the primers on the basis of a size differential, or through the immobilization of the product, allowing washing away of free primer. However, three methods for monitoring the amplification process without prior separation of primer have been described. All of them are based on FRET, and none of them detect the amplified product directly. Instead, all three methods detect some event related to amplification. For that reason, they are accompanied by problems of high background, and are not quantitative, as discussed below.

One method, described in Wang et al. (U.S. Pat. No. 5,348,853; Wang et al., 1995, Anal. Chem. 67: 1197–1203), uses an energy transfer system in which energy transfer occurs between two fluorophores on the probe. In this method, detection of the amplified molecule takes place in the amplification reaction vessel, without the need for a separation step. This method results in higher sensitivity than methods that rely on monolabeled primers.

The Wang et al. method uses an "energy-sink" oligonucleotide complementary to the reverse primer. The "energy-sink" and reverse-primer oligonucleotides have donor and acceptor labels, respectively. Prior to amplification, the labeled oligonucleotides form a primer duplex in which energy transfer occurs freely. Then, asymmetric PCR is carried out to its late-log phase before one of the target strands is significantly overproduced.

A primer duplex complementary to the overproduced target strand is added to prime a semi-nested reaction in concert with the excess primer. As the semi-nested amplification proceeds, the primer duplex starts to dissociate as the target sequence is duplicated. As a result, the fluorophores configured for energy transfer are disengaged from each other, causing the energy transfer process preestablished in all of the primer duplexes to be disrupted for those primers involved in the amplification process. The measured fluorescence intensity is proportional to the amount of primer duplex left at the end of each amplification cycle. The decrease in the fluorescence intensity correlates proportionately to the initial target dosage and the extent of amplification.

This method, however, does not detect the amplified product, but instead detects the dissociation of primer from the "energy-sink" oligonucleotide. Thus, this method is dependent on detection of a decrease in emissions; a significant portion of labeled primer must be utilized in order to achieve a reliable difference between the signals before and after the reaction. This problem was apparently noted by Wang et al., who attempted to compensate by adding a preliminary amplification step (asymmetric PCR) that is supposed to increase the initial target concentration and consequently the usage of labeled primer, but also complicates the process.

A second method for detection of amplification product without prior separation of primer and product is the 5' nuclease PCR assay (also referred to as the TaqMan® assay) (Holland et al., 1991, Proc. Natl. Acad. Sci. USA 88: 7276–7280; Lee et al., 1993, Nucleic Acids Res. 21: 3761–3766). This assay detects the accumulation of a specific PCR product by hybridization and cleavage of a doubly labeled fluorogenic probe (the "TaqMan" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

In the TaqMan assay, the donor and quencher are preferably located on the 3' and 5'-ends of the probe, because the requirement that 5'-3' hydrolysis be performed between the fluorophore and quencher may be met only when these two moieties are not too close to each other (Lyamichev et al., 1993, Science 260:778–783). However, this requirement is a serious drawback of the assay, since the efficiency of energy transfer decreases with the inverse sixth power of the distance between the reporter and quencher. In other words, the TaqMan assay does not permit the quencher to be close enough to the reporter to achieve the most efficient quenching. As a consequence, the background emissions from unhybridized probe can be quite high.

Furthermore, the TaqMan assay does not measure the amplification product directly, because the amplification primers are not labeled. This assay measures an event related to amplification: the hydrolysis of the probe that hybridizes to the target DNA between the primer sequences. As a result, this assay method is accompanied by significant problems.

First, hybridization will never be quantitative unless the labeled oligonucleotide is present in great excess. However, this results in high background (because the quenching is never quantitative). In addition, a great excess of oligonucleotide hybridized to the middle of the target DNA will decrease PCR efficiency. Furthermore, not all of the oligonucleotides hybridized to the DNA will be the subject of 5'-3' exonuclease hydrolysis: some will be displaced without hydrolysis, resulting in a loss of signal.

Another method of detecting amplification products that relies on the use of energy transfer is the "beacon probe" method described by Tyagi and Kramer (1996, Nature Biotech. 14:303–309) which is also the subject of U.S. Pat. Nos. 5,119,801 and 5,312,728 to Lizardi et al. This method employs oligonucleotide hybridization probes that can form hairpin structures. On one end of the hybridization probe (either the 5' or 3' end) there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce (Tyagi and Kramer, 1996, Nature Biotechnol. 14: 303–306. As a result, the amount of fluorescence will increase as the amount of PCR product increases, and thus may be used as a measure of the progress of the PCR.

However, since this method is based on hybridization of the probe to template between the primer sequences, it has a number of problems associated with it, some of which are similar to those described above in connection with the TaqMan method. First, it is unlikely that the beacon probes will hybridize quantitatively to one strand of double-stranded PCR product, especially when the amplification product is much longer than the beacon probe. Even those probes that are hybridized could be displaced by the second DNA strand over a short period of time; as a result, this method cannot be quantitative.

Efforts to increase the hybridization efficiency by increasing the concentration of beacon probe will result in decreased amplification efficiency, since the necessity for DNA polymerase to displace hybridized beacons during the reaction will slow down the rate of polymerization. An excess of probe will also increase the background. In addition, the ratio between the amplification product and the beacon probes will change as amplification proceeds, and so will change the efficiency of hybridization. Thus the detection of the amplified product may not be quantitative.

Therefore, in view of the deficiencies in prior art methods of detecting amplification products, it is clear that there exists in the art a need for an improved method of detecting amplification products rapidly, sensitively, reliably and quantitatively. The present invention solves this problem by providing nucleic acid amplification primers that are detectably labeled with energy-transfer labels. It also solves this problem by providing methods for detecting amplification products that are adaptable to many methods for amplification of nucleic acid sequences and that greatly decrease the possibility of carryover contamination with amplification products.

Citation of references herein shall not be construed as an admission that such references are prior art to the present invention.

3. SUMMARY OF THE INVENTION

The present invention relates to oligonucleotides for amplification of nucleic acids that are detectably labeled with molecular energy transfer (MET) labels. One or more oligonucleotides of the invention containing a donor and/or acceptor moiety of a MET pair are incorporated into the amplified product of an amplification reaction, such that the amplified product contains both a donor and acceptor moiety of a MET pair. When the amplified product is double-stranded, the MET pair incorporated into the amplified product may be on the same strand or, when the amplification is triamplification, on opposite strands. In certain instances wherein the polymerase used in amplification has 5'-3' exonuclease activity, one of the MET pair moieties may be cleaved from at least some of the population of amplified product by this exonuclease activity. Such exonuclease activity is not detrimental to the amplification methods of the invention.

The invention also relates to methods for detecting the products of nucleic acid amplification using these labeled oligonucleotides of the invention. It further relates to a rapid, sensitive, and reliable method for detecting amplification products that greatly decreases the possibility of carryover contamination with amplification products and that is adaptable to many methods for amplification of nucleic acid sequences, including polymerase chain reaction (PCR), triamplification, and other amplification systems.

The nucleic acid amplification oligonucleotides of the invention utilize the principle of molecular energy transfer (MET) between a donor moiety and an acceptor moiety. In a preferred embodiment, the MET is fluorescence resonance energy transfer (FRET), in which the oligonucleotides are labeled with donor and acceptor moieties, wherein the donor moiety is a fluorophore and the acceptor moiety may be a fluorophore, such that fluorescent energy emitted by the donor moiety is absorbed by the acceptor moiety. In one embodiment of the present invention, the acceptor moiety is a fluorophore that releases the energy absorbed from the donor at a different wavelength; the emissions of the acceptor may then be measured to assess the progress of the amplification reaction. In another embodiment, the acceptor moiety is a quencher.

In a preferred embodiment, the amplification primer is a hairpin primer that contains both donor and acceptor moieties, and is configured such that the acceptor moiety quenches the fluorescence of the donor. When the primer is incorporated into the amplification product its configuration changes, quenching is eliminated, and the fluorescence of the donor moiety may be detected.

In one embodiment, the present invention provides nucleic acid amplification primers that form a hairpin structure in which MET will occur when the primer is not incorporated into the amplification product. In a preferred embodiment, a primer forms a hairpin structure in which the energy of a donor fluorophore is quenched by a non-fluorescing fluorophore when the primer is not incorporated into the amplification product.

In another embodiment, the present invention provides oligonucleotides that are linear (non-duplex) and that are separately labeled with donor and acceptor moieties, such that MET will occur when the oligonucleotides are incorporated into the amplification product. For example, the blocking oligonucleotide and the reverse primer complementary to the blocking oligonucleotide can be so labeled in a triamplification reaction.

In yet another embodiment, the donor moiety and acceptor moiety are on a single, linear oligonucleotide used in an amplification reaction.

The present invention also provides a method of directly detecting amplification products. This improved technique meets two major requirements. First, it permits detection of the amplification product without prior separation of unincorporated oligonucleotides. Second, it allows detection of the amplification product directly, by incorporating the labeled oligonucleotide into the product.

The present invention provides a method of directly detecting amplification products through the incorporation of labeled oligonucleotide(s) (e.g., primers, blocking oligonucleotides) wherein instead of separating unincorporated oligonucleotides from amplification product, as in prior art approaches, signal from the remaining free oligonucleotide(s) is eliminated in one (or more) of the following ways:

a) by treatment with a 3'-5' exonuclease;
b) by heating the amplification product to a temperature such that the primer-oligonucleotide duplex dissociates and, as a result, will not generate any signal; or
c) by using a primer labeled with both donor and acceptor moieties and that can form a hairpin structure, in which the energy transfer from donor to acceptor will occur only when the primer is not incorporated into the amplification product.

In a further embodiment, the present invention provides a method for the direct detection of amplification products in which the detection may be performed without opening the reaction tube. This embodiment, the "closed-tube" format, reduces greatly the possibility of carryover contamination with amplification products that has slowed the acceptance of PCR in many applications. The closed-tube method also provides for high throughput of samples and may be totally automated. The present invention also relates to kits for the detection or measurement of nucleic acid amplification products. Such kits may be diagnostic kits where the presence of the nucleic acid being amplified is correlated with the presence or absence of a disease or disorder.

3.1. DEFINITIONS

As used herein, the following terms shall have the abbreviations indicated.

ARMS, amplification refractory mutation system
ASP, allele-specific polymerase chain reaction
bp, base pairs
CRCA, cascade rolling circle amplification
DAB or DABCYL, 4-(4'-dimethylaminophenylazo) benzoic acid
EDANS, 5-(2'-aminoethyl) aminonapthalene-1-sulfonic acid
FAM or Flu, 5-carboxyfluorescein
FRET, fluorescence resonance energy transfer
JOE, 2'7'-dimethoxy-4'5-dichloro-6-carboxyfluorescein
HPLC, high-performance liquid chromatography
MET, molecular energy transfer
NASBA, nucleic acid sequence-based amplification
PSA, prostate specific antigen
Rhod, rhodamine
ROX, 6-carboxy-X-rhodamine
R6G, 6-carboxyrhodamine
SDA, strand displacement amplification
TAMRA, N,N,N',N'-tetramethyl-6-carboxyrhodamine
TRAP, telomeric repeat amplification protocol

4. DESCRIPTION OF THE FIGURES

The present invention may be understood more fully by reference to the following detailed description of the invention, examples of specific embodiments of the invention and the appended figures described below:

FIGS. 1A–B illustrate schematically the structure of the hairpin primers of the invention in the (A) closed (quenched) and (B) open (emitting signal) states. ○, donor fluorophore; •, quencher fluorophore.

FIG. 2 illustrates schematically the use of hairpin primers to directly measure the amplification products from a PCR in which the employed DNA polymerase lacks 5'-3' exonuclease activity. An energy transfer signal is generated upon the incorporation of the hairpin primer into the double-stranded PCR product. (a) and (b), complementary strands of the target sequence to be amplified; ○ donor fluorophore; •, quencher; F, forward primer; R, reverse primer.

FIG. 3 (Steps A–D) illustrates the amplification products from a PCR in which the employed DNA polymerase has 5'-3' exonuclease activity. (a) and (b), complementary strands of the target sequence to be amplified; ○ donor fluorophore; •, quencher; F, forward primer; R, reverse primer.

FIG. 4 gives a schematic example of a selected target sequence (SEQ ID NO:1) ligated to a universal hairpin (SEQ ID NO:2). (d) is the selected primer sequence of 8–40 nucleotides, preferably ~15 nucleotides, that is complementary to the target nucleic acid sequence to be amplified. (d') is the 5' cohesive end of the selected primer sequence. The cohesive end is 1–10 nucleotides, preferably 3–4 nucleotides, and complementary to the 5' cohesive end (a') of the universal hairpin. (b) is a loop on the universal hairpin that is long enough provide a distance of 15–25 nucleotides, preferably 20 nucleotides, between the donor (F, FAM) and the quencher (D, DABCYL) when the hairpin is in the "open" configuration. (a) and (c) are the two strands of the stem of the universal hairpin. When the selected primer sequence is ligated to the universal hairpin, the quencher (DABCYL) will be located on a nucleotide that is internal to the 3' end. The donor (FAM) may be located on a nucleotide either at the 5' end (as shown) or internal to the 5' end. The only requirement is that the donor and quencher are close enough to enable quenching when the hairpin is in the "closed" ("silent") conformation.

FIG. 5 illustrates schematically the use of a FRET donor-acceptor-labeled hairpin primer in PCR. See Section 5.2.1 for a detailed description of Cycles 1–4.

FIG. 6 illustrates schematically the use of a FRET donor-acceptor-labeled hairpin primer in triamplification. In this embodiment of triamplification, unlike in PCR, a third oligonucleotide ("blocker") is ligated to the extended hairpin primer. The fluorescent signal is generated as a result of replication, however, as occurs in PCR.

FIG. 7 illustrates schematically triamplification using two linear primers, each labeled with a FRET moiety. BL, blocker; R, reverse primer; F, forward primer; ■, a commercially available 3' modifying group able to protect the oligonucleotide from extension by DNA polymerase or hydrolysis by 3'-5' exonuclease on the 3' end of the blocker; X, 2'-O-methyl-modification in reverse primer; D, donor fluorophore; A○, acceptor fluorophore.

FIGS. 8A–B illustrate the effect of (A) 3'-5' exonuclease and (B) elevated temperature on unincorporated FRET-labeled primers during triamplification. BL, blocker; R, reverse primer; F, forward primer; P, 5' phosphate; ■, protection group on 3'-end of blocker; X, 2'-O-methyl-modification in reverse primer; D, donor fluorophore; A○, acceptor fluorophore.

FIG. 9 illustrates schematically the use of hairpin primers in nucleic acid sequence-based amplification (NASBA). NASBA depends on continuous cycling of the reverse transcription and RNA transcription reactions at one temperature. See Section 5.2.3 for a detailed description of Steps 1–9.

FIG. 10 illustrates schematically the use of hairpin primers in strand displacement amplification (SDA) of a double-stranded DNA target. Primers 1 and 2 differ, being forward and reverse primers, respectively. SDA depends on continuous cycling of the nicking and the polymerization/displacement steps at one temperature. See Section 5.2.4 for a detailed description of Steps 1–4. pol, polymerase; restrictase, restriction endonuclease.

FIGS. 11A–B illustrate a two-chamber amplification tube in "closed-tube" format. The tube can be inverted (FIG. 11B) and used to mix 3'-5' exonuclease with amplification product only when desired, without opening the tube after amplification takes place (see Section 12, Example 6).

FIG. 12 illustrates portions of the two strands (upper strand: SEQ ID NO:3 and SEQ ID NO:4; lower strand: SEQ ID NO:8 and SEQ ID NO:9) of the template, and the oligonucleotides, PSA-I (SEQ ID NO:5), PSA-P (SEQ ID NO:6), and PSA-B (SEQ ID NO:7), used in the amplification of human prostate specific antigen (PSA) DNA as described in all the examples except those employing hairpin primers, the sequences of which are provided in Section 12.

FIGS. 13A–C. FIG. 13A illustrates schematically the PCR amplification procedure used in the experiment described in Section 7 (Example 1). The left portion of FIG. 13A illustrates a PCR amplification using a rhodamine-modified reverse primer. The right portion of FIG. 13A illustrates a PCR amplification using a non-modified reverse primer. The results are shown on the accompanying denaturing 6% polyacrylamide gel (FIG. 13B) and agarose gel (FIG. 13C). FIG. 13B compares the sizes of the DNA strands that were amplified with [$^{32}$P]-labeled forward primer when non-modified reverse primer (Lane 1) or rhodamine-modified reverse primer (Lane 2) was used. FIG. 13C compares the amounts of double-stranded PCR amplification product obtained with non-modified reverse primer (Lane 1) and rhodamine-modified reverse primer (Lane 2).

FIGS. 14. FIG. 14A–B illustrates schematically the experimental procedure used in Section 8 (Example 2). The results are shown in the accompanying denaturing 6% polyacrylamide gel (FIG. 14B). Lane 1 of the gel represents a strand of amplified DNA with incorporated [$^{32}$P]-and rhodamine-labeled reverse primer, while Lane 2 represents a strand of amplified DNA with incorporated [$^{32}$P]-labeled forward (F) primer.

FIGS. 15A–B. FIG. 15A illustrates schematically the experimental procedure used in Section 9 (Example 3). The results are shown on the accompanying denaturing 15% polyacrylamide gel (FIG. 15B). Lane 1 of the gel represents [$^{32}$P]- and rhodamine-labeled reverse primer, Lanes 2–4 represent [$^{32}$P]- and rhodamine-labeled reverse primer after incubation with T4 DNA polymerase that has 3'-5' exonuclease activity for 2 minutes (Lane 2), 5 minutes (Lane 3), and 15 minutes (Lane 4).

FIG. 16 illustrates the detection of amplification product by FRET after nuclease treatment (Section 10, Example 4). Emission spectrum 1 was obtained after triamplification with DNA template and exonuclease treatment. Spectrum 2 was obtained after triamplification without DNA template and exonuclease treatment (no DNA control).

FIGS. 17A–B illustrates the effect of elevated temperatures (750° C.) on FRET following triamplification (A) without and (B) with DNA template (Section 11, Example 5).

FIGS. 18A–B FIG. 18A depicts the structure of the PSA cDNA upstream hairpin primer (SEQ ID NO:10). The portion of the sequence complementary to the target DNA is shown in bold. FIG. 18B shows an emission spectrum of the fluorescein-labeled hairpin primer in the absence (1) and presence (2) of a DABCYL moiety. The spectra obtained from 0.5 ml of a 40 nM sample of oligonucleotide were measured as described in Section 6.4 using a 488 nm excitation wavelength.

FIG. 19 shows the efficiency of amplification with the hairpin primers. Products of amplification were separated on an MDE™ gel (FMC Bioproducts, Rockland Me.). An ethidium-bromide stained gel is shown. Lanes 1–3 show the products of amplification of $10^{-9}$ M PSA cDNA with unlabeled control linear primer (Lane 1), FAM-hairpin primer (Lane 2), and FAM/DABCYL-hairpin primer (Lane 3). Lanes 4–6 show the products of amplification of $10^{-11}$ M PSA cDNA with control primer (Lane 4), FAM-hairpin primer (Lane 5), and FAM/DABCYL-hairpin primer (Lane 6). Lane M contains a 100 bp marker (Gibco BRL).

FIGS. 20A–B illustrates schematically and shows the results, respectively, of a PCR amplification in the presence of hairpin primers. PCR amplification of PSA cDNA was performed with two primers: an upstream hairpin primer labeled with FAM and DABCYL, and a downstream primer labeled with $^{32}$P on its 5' end (FIG. 20A). An upstream primer without the hairpin structure was used as a control. The structure of the hairpin primer is presented in FIG. 18A and the sequences of the regular primers are presented in Section 12.3. FIG. 20B is an autoradiogram that shows the size of the PCR product synthesized. [$^{32}$P]-labeled strands of the PCR products were synthesized in the presence of the unlabeled control linear primer (Lane 1) or FAM/DABCYL-labeled hairpin primer (Lane 2) and analyzed on a 6% denaturing polyacrylamide gel.

FIGS. 21A–B FIG. 21A shows the fluorescence spectra of the amplification reactions performed with the hairpin primers labeled with FAM/DABCYL. The structure of the FAM/DABCYL labeled hairpin primer is presented in FIG. 18A and the sequence of the regular downstream primer is presented in Section 12.3. Spectra 1–6 show the fluorescence intensity of the amplified PSA cDNA after 0 (1), 20 (2), 25 (3), 30 (4), 35 (5) or 40 (6) cycles. FIG. 21B shows the fluorescence intensity of the amplification reaction mixtures and the fraction of the [$^{32}$P]-labeled primers incorporated into the PCR products plotted against the number of cycles. The incorporation of the [$^{32}$P]-labeled primers into the PCR products was determined by electrophoresis on a 6% denaturing gel and quantitated using the PhosphorImager.

FIG. 22 shows the sensitivity of PCR with hairpin primers. Spectra 1–6 show the results of the amplification when 0 (1), 10 (2), $10^2$ (3), $10^3$ (4), $10^4$ (5), $10^5$ (6) or $10^6$ (7) molecules of cloned PSA cDNA per reaction were used as template DNA for the 40 cycles of PCR. The structure of the FAM/DABCYL labeled hairpin primer is presented in FIG. 18A and the sequence of the regular downstream primer is presented in Section 12.3.

FIG. 23 shows the visible fluorescence of PCR products synthesized with hairpin primers. $10^6$ (Tube 1), $10^4$ (Tube 2), $10^3$ (Tube 3) and 0 (Tube 4) molecules of the cloned PSA cDNA template were used as template DNA for the 40 cycles of PCR with FAM/DABCYL labeled hairpin primers. DNA fluorescence was visualized in 0.2 ml thin-walled PCR tubes using an UV transilluminator image analysis system.

FIGS. 24A–G show the fluorescence intensity of PSA cDNA amplified with different FAM/DABCYL-labeled hairpin primers (FIGS. 24A–G correspond to SEQ ID NOS:13–18, and 25, respectively). All primers had at least an 18-nucleotide sequence complementary to the target, which consisted of a 3' single-stranded priming sequence, a 3' stem sequence and part of the loop. Sequences complementary to the target DNA are shown in shadowed bold italics. f, FAM; d, DABCYL; nucl, nucleotide number; rel. (%), percent intensity of fluorescence relative to DNA amplified with Primer A.

FIG. 25 illustrates schematically the use of linear primers to directly measure the amplification products from a PCR. An energy transfer signal is generated upon the incorporation of the primer into the double-stranded PCR product. After amplification, the signal from unincorporated primer is eliminated by 3'-5' exonuclease hydrolysis. D, donor moiety; A, acceptor moiety; F, forward primer; R, reverse primer.

FIG. 26 illustrates the three sets of PCR primers used in the experiments in Section 13, Example 7. Uup (SEQ ID NO:19) and Ud (SEQ ID NO:20), are the upstream and downstream primers, respectively, for sequences of bisulfite-treated unmethylated DNA. Mup (SEQ ID NO:21) and Md (SEQ ID NO:22), are the upstream and downstream primers, respectively, for sequences of bisulfite-treated methylated DNA. Wup (SEQ ID NO:23) and Wd (SEQ ID NO:24), are the upstream and downstream primers, respectively, for DNA not treated with bisulfite. One of the two primers in each set has a hairpin structure at its 5' end, labeled with a FAM/DAB (DABCYL) FRET pair at the positions illustrated.

FIG. 27 shows an example of the structure of a hairpin primer, BSK38, (SEQ ID NO:26) that can be used in the in situ PCR of a gag viral sequence, described in Section 17, Example 11.

FIGS. 28A–B show the visual fluorescence of PCR products synthesized with a universal hairpin primer, described in Section 14, Example 8. Cloned PSA cDNA (A; upper row) and Chlamydia genomic DNA (B; lower row) were used as a target. Column (1), complete reaction mixture. Column (2), Control 1, reaction mixture without tailed primer. Column (3), Control 2, reaction mixture without DNA template.

FIGS. 29A–B show a TRAP (telomeric repeat amplification protocol) assay that utilizes PCR and assays for telomerase activity cells or tissues of interest. In FIG. 29A (Step 1), telomerase adds a number of telomeric repeats (GGTTAG) (longest repeat shown in lower line being SEQ ID NO:27) on the 3' end of a substrate oligonucleotide (SEQ ID NO:28) (TS, telomerase substrate).

In FIG. 29B (Step 2), the extended products are amplified by PCR using the TS and a reverse primer (RP), generating a ladder of products with 6 base increments starting at 50 nucleotides: 50, 56, 62, 68, etc.

FIG. 30A shows the sequence of the hairpin primer (SEQ ID NO:37) that was used in the TRAP assay described in Example 9, Section 15.

FIG. 30B shows the results from a TRAP assay performed using TS primer and a hairpin RP primer of the sequence shown in FIG. 30A. Assays were run on cell extracts equivalent to 10,000, 1,000, 100 or 10 cells. Three negative controls were also run. No Taq, no Taq polymerase was added in the reaction (negative control 1). CHAPS, CHAPS lysis buffer was used instead of cell extract in the reaction (negative control 2). +H, cell extract from 10,000 cells was heat-treated prior to the assay (negative control 3). 10, TRAP assay with cell extract from 10 cells. 100, TRAP assay with cell extract from 100 cells. 1,000, TRAP assay with cell extract from 1,000 cells. 10,000, TRAP assay with cell extract from 10,000 cells.

FIG. 31 depicts diagrammatically Cascade Rolling Circle Amplification (CRCA), which is described in Section 25 5.2.6. Q, quencher; F, fluorophore.

FIGS. 32A and 32B show rolling circle (forward) hairpin primers 1 and 2 (SEQ ID NOS:46 and 47, respectively), reverse hairpin primers 1 and 2 (SEQ ID NOS:48 and 49, respectively), non-hairpin forward (rolling circle) primer (SEQ ID NO:50), non-hairpin reverse primer (SEQ ID NO:51), as described in Section 19, Example 13. The hairpin primer sequences complementary to the probe or rolling circle products are underlined. Non-hairpin (i.e., linear) forward primer (SEQ ID NO:50) had a sequence corresponding to the underlined portion of the forward (rolling circle) hairpin primer sequences 1 and 2. Non-hairpin reverse primer (SEQ ID NO:51) had a sequence corresponding to the underlined portion of the reverse hairpin primer sequences 1 and 2. Spacer sequences are shown in bold. The nucleotides to which the two moieties of a MET pair are attached are marked with asterisks (*).

Also depicted in FIG. 32 is a diagram of a circularized probe for CRCA, which comprises a target specific sequence (5'-TGTAGCCGTAGTTAGGCCACCACTTCAAGAACTCT-3') (SEQ ID NO:52) for pUC19 and a spacer (generic) sequence that includes a ligation junction as described in Section 19, Example 13. A target specific sequence for ras (5'-GTTGGAGCTGGTGGCGTAG-3') (SEQ ID NO:53) is also depicted. The ras-specific sequence was used as a target specific sequence in an additional experiment described in Section 19, Example 13. nucl, nucleotide number. bp, base pairs. T*, T nucleotide with DABCYL moiety attached. A*, A nucleotide with FAM moiety attached.

FIG. 33 shows the results of a series of Cascade Rolling Circle Amplifications (CRCAs) with hairpin primers, as described in Section 19, Example 13. The number of template circles, i.e. circularized probe made using pUC19 as target, used in each reaction is indicated on the X-axis. MET signals, as measured in fluorescence units (Y-axis), were detected by fluorometric analysis of signal levels in CRCAs (plus ligase) relative to background levels in control reactions (minus ligase). -☐-, minus ligase; -Δ-, plus ligase.

5. DETAILED DESCRIPTION OF THE INVENTION

Figure 2:
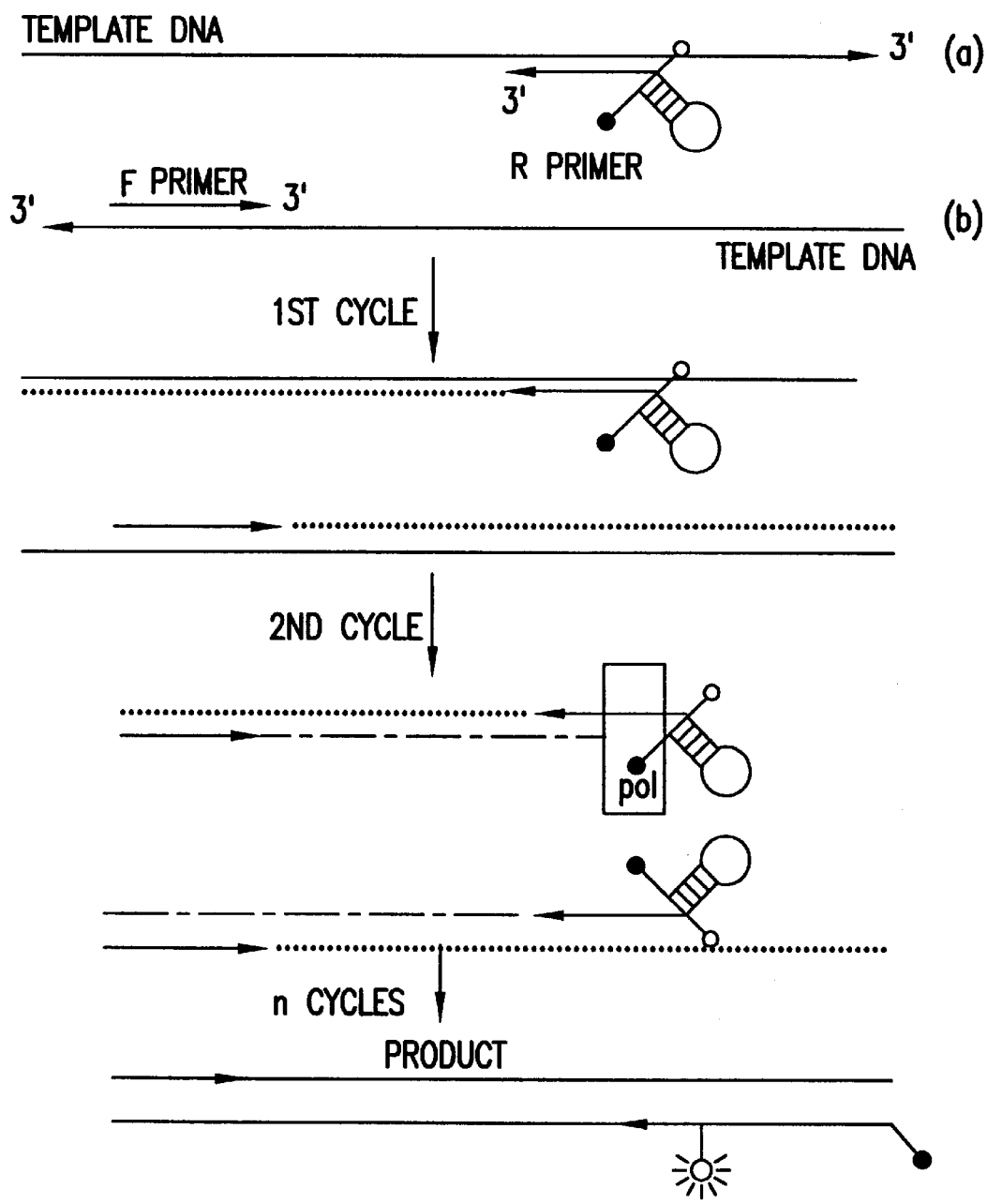

The present invention relates to oligonucleotides for amplification of nucleic acids that are detectably labeled with molecular energy transfer (MET) labels. One or more oligonucleotides of the invention containing a donor and/or acceptor moiety of a MET pair are incorporated into the amplified product of an amplification reaction, such that the amplified product contains both a donor and acceptor moiety of a MET pair. When the amplified product is double-stranded, the MET pair incorporated into the amplified product may be on the same strand or, when the amplification is triamplification, on opposite strands. In certain instances wherein the polymerase used in amplification has 5'-3' exonuclease activity, one of the MET pair moieties may be cleaved from at least some of the population of amplified product by this exonuclease activity. Such exonuclease activity is not detrimental to the amplification methods of the invention.

The invention also relates to methods for detecting the products of nucleic acid amplification using these labeled oligonucleotides of the invention. It further relates to a rapid, sensitive, and reliable method for detecting amplification products that greatly decreases the possibility of carryover contamination with amplification products and that is adaptable to many methods for amplification of nucleic acid sequences, including polymerase chain reaction (PCR), triamplification, and other amplification systems.

The nucleic acid amplification oligonucleotides of the invention utilize the principle of MET between a donor moiety and an acceptor moiety. In a preferred embodiment, the MET is fluorescence resonance energy transfer (FRET), in which the oligonucleotides are labeled with donor and acceptor moieties, wherein the donor moiety is a fluorophore and the acceptor moiety may be a fluorophore, such that fluorescent energy emitted by the donor moiety is absorbed by the acceptor moiety. In one embodiment of the present invention, the acceptor moiety is a fluorophore that releases the energy absorbed from the donor at a different wavelength; the emissions of the acceptor may then be measured to assess the progress of the amplification reaction.

In a preferred embodiment, the amplification primer is a hairpin primer that contains both donor and acceptor moieties and is configured such that the acceptor moiety quenches the fluorescence of the donor. When the primer is incorporated into the amplification product its configuration changes, quenching is eliminated, and the fluorescence of the donor moiety may be detected.

In one embodiment, the present invention provides nucleic acid amplification primers that form a hairpin structure in which MET will occur when the primer is not incorporated into the amplification product. In a preferred embodiment, a primer forms a hairpin structure in which the energy of a donor fluorophore is quenched by a non-fluorescing fluorophore when the primer is not incorporated into the amplification product.

In another embodiment, the present invention provides oligonucleotides that are linear (non-duplex) and that are separately labeled with donor and acceptor moieties, such that MET will occur when the oligonucleotides are incorporated into the amplification product. For example, the blocking oligonucleotide and the primer complementary to the blocking oligonucleotide can be so labeled in a triamplification reaction.

In yet another embodiment, using a pair of linear primers, the donor moiety and acceptor moiety are on a single linear primer used in the amplification reaction. Where the amplification reaction is triamplification, the oligonucleotide labeled with both the donor and acceptor moieties is not the blocking oligonucleotide.

The invention provides a method for detecting or measuring a product of a nucleic acid amplification reaction comprising: (a) contacting a sample comprising nucleic acids with at least two oligonucleotides, a first one of said oligonucleotides comprising a sequence complementary to a preselected target sequence that may be present in said sample, and said first one and a second of said oligonucleotides being a pair of primers adapted for use in said amplification reaction such that said primers are incorporated into an amplified product of said amplification reaction when said target sequence is present in the sample; at least one of said primers being labeled with a first moiety selected from the group consisting of a donor moiety and an acceptor moiety of a molecular energy transfer pair; and wherein the same or a different oligonucleotide is labeled with a second moiety selected from the group consisting of said donor moiety and said acceptor moiety, said second moiety being the member of said group that is not said first moiety, wherein said primer labeled with said first moiety and said oligonucleotide labeled with said second moiety are configured so as to be incorporated into said amplified product, wherein the donor moiety emits energy of one or more particular wavelengths when excited, and the acceptor moiety absorbs energy at one or more particular wavelengths emitted by the donor moiety; (b) conducting the amplification reaction; (c) stimulating light emission from said donor moiety; and (d) detecting or measuring energy emitted by said donor moiety or acceptor moiety.

The nucleic acids in the sample may be purified or unpurified.

In a specific embodiment, the oligonucleotides of the invention are used in in situ amplification reactions, performed on samples of fresh or preserved tissues or cells. In in situ reactions, it is advantageous to use methods that allow for the accurate and sensitive detection of the target directly after the amplification step. In contrast, conventional in situ PCR requires, in paraffin embedded tissue, detection by a hybridization step, as the DNA repair mechanism invariably present in tissue samples from, e.g., CNS, lymph nodes, and spleen, precludes detection by direct incorporation of a reporter nucleotide during the PCR step. Typically, when conventional linear primers labelled with biotin or digoxigenin moieties are employed in in situ PCR, little or no detectable label is incorporated during amplification, which comprises annealing and extension steps. Moreover, when amplification reaction conditions are modified to enhance incorporation of nucleotides labeled with such moieties, unacceptably high background and false positive results are obtained. This can be attributed to the activity of endogenous DNA repair enzymes, which incorporate the labeled nucleotides into nicked DNA in the sample. Others have attempted to use other types of singly labeled PCR primers (Nuovo, 1997, *PCR In Situ Hybridization: Protocols and Applications, Third Edition*, Lippincott-Raven Press, New York), but have not been able to achieve adequate sensitivity, which can lead to false negative results. The requirements for a hybridization step, followed by a washing step, add additional time and expense to conventional in situ PCR protocols. It is therefore advantageous to use methods that allow for the accurate and sensitive detection of the target directly after the amplification step. Such methods are afforded by the present invention.

In a specific embodiment, the energy emitted by the donor moiety (e.g., when a quencher is the acceptor moiety) or by the acceptor moiety (e.g., when a fluorophore or chromophore is the acceptor moiety), that is detected and measured after conducting an amplification reaction of the invention correlates with the amount of the preselected target sequence originally present in the sample, thereby allowing determination of the amount of the preselected target sequence present in the original sample. Thus, the methods of the invention can be used quantitatively to determine the number of chromosomes, or amount of DNA or RNA, containing the preselected target sequence.

A pair of primers, consisting of a forward primer and a reverse primer, for use in PCR or strand displacement amplification, consists of primers that are each complementary with a different strand of two complementary nucleic acid strands, such that when an extension product of one primer in the direction of the other primer is generated by a nucleic acid polymerase, that extension product can serve as a template for the synthesis of the extension product of the other primer. A pair of primers, consisting of a forward primer and a reverse primer, for use in triamplification, consists of primers that are each complementary with a different strand of two complementary nucleic acid strands, such that when an extension-ligation product of one primer in the direction of the other primer is generated by a nucleic acid polymerase and a nucleic acid ligase, that extension-ligation product can serve as a template for the synthesis of the extension-ligation product of the other primer. The amplified product in these instances is that content of a nucleic acid in the sample between and including the primer sequences.

As referred to herein, nucleic acids that are "complementary" can be perfectly or imperfectly complementary, as long as the desired property resulting from the complementarity is not lost, e.g., ability to hybridize.

In a specific embodiment, the invention provides a method for detecting or measuring a product of a nucleic acid amplification reaction comprising (a) contacting a sample comprising nucleic acids with at least two oligonucleotide primers, said oligonucleotide primers being adapted for use in said amplification reaction such that said primers are incorporated into an amplified product of said amplification reaction when a preselected target sequence is present in the sample; at least one of said oligonucleotide primers being a hairpin primer of the invention labeled with a donor moiety and an acceptor moiety; (b) conducting the amplification reaction; (c) stimulating energy emission from said donor moiety; and (d) detecting or measuring energy emitted by said donor moiety.

The present invention also provides a method of directly detecting amplification products. This improved technique meets two major requirements. First, it permits detection of the amplification product without prior separation of unincorporated oligonucleotides. Second, it allows detection of the amplification product directly, by incorporating the labeled oligonucleotide(s) into the product.

The present invention provides a method of directly detecting amplification products through the incorporation of labeled oligonucleotide(s) (e.g., primers, blocking oligonucleotides) wherein instead of separating unreacted oligonucleotides from amplification product, as in prior art approaches, signal from the remaining free oligonucleotide(s) is eliminated in one (or more) of the following ways:

a) by treatment with a 3'-5' exonuclease;

b) by heating the amplification product to a temperature such that the primer-oligonucleotide duplex dissociates and, as a result, will not generate any signal; or c) by using a primer labeled with both donor and acceptor moieties and that can form a hairpin structure, in which the energy transfer from donor to acceptor will occur only when the primer is not incorporated into the amplification product.

In a further embodiment, the present invention provides a method for the direct detection of amplification products in which the detection may be performed without opening the reaction tube. This embodiment, the "closed-tube" format, reduces greatly the possibility of carryover contamination with amplification products that has slowed the acceptance of PCR in many applications. The closed-tube method also provides for high throughput of samples and may be totally automated. The present invention also relates to kits for the detection or measurement of nucleic acid amplification products. Such kits may be diagnostic kits where the presence of the nucleic acid being amplified is correlated with the presence or absence of a disease or disorder.

For clarity of disclosure, and not by way of limitation, the detailed description of the invention is divided into the subsections set forth below.

5.1. OLIGONUCLEOTIDES

The present invention provides oligonucleotides for nucleic acid amplification that are incorporated into the amplified product and that utilize the principle of molecular energy transfer (MET) and, preferably, fluorescence resonance energy transfer (FRET). The oligonucleotides of the invention are labeled with a donor and/or an acceptor moiety, i.e., a "MET pair." The acceptor moiety may simply quench the emission of the donor moiety, or it may itself emit energy upon excitation by emission from the donor moiety. In a preferred embodiment, the donor moiety is a fluorophore and the acceptor moiety may or may not be a fluorophore, such that fluorescent energy emitted by the donor moiety is absorbed by the acceptor moiety. The labeled oligonucleotides are forward and/or reverse primers, and/or, in the case of triamplification, a blocking oligonucleotide. The oligonucleotides used in the amplification reaction are labeled such that at least one MET pair is incorporated into the amplified product (although 5'-3' exonuclease activity, if present, may subsequently remove a moiety from at least some of the amplified product population).

In one embodiment of the present invention, the acceptor moiety is a fluorophore that releases the energy absorbed from the donor at a different wavelength; use of the emissions of the donor and/or acceptor may then be measured to assess the progress of the amplification reaction, depending on whether the donor and acceptor moieties are incorporated into the amplification product close enough for MET to occur. In another embodiment, the acceptor moiety is a quencher that quenches the fluorescence of the donor when the donor and acceptor moieties are incorporated into the amplification product close enough for MET to occur.

In a further specific embodiment (see Section 5.1.1 infra), an oligonucleotide primer is used that forms a hairpin structure in which FRET will occur, when the primer is not incorporated into the amplification product. In a preferred embodiment, the hairpin primer is labeled with a donor-quencher FRET pair. When the hairpin primer is incorporated into the amplification product, its configuration changes (i.e., it is linearized), quenching is eliminated, and the fluorescence of the donor may be detected.

In yet another embodiment (see Section 5.1.2 infra), the labeled oligonucleotide, that can be a primer or, in the case of triamplification, a blocking oligonucleotide, is a linear molecule that does not form a hairpin configuration. In one embodiment, the donor-acceptor FRET pair is located on the same, single-stranded oligonucleotide primer. In another embodiment, the donor moiety is located on a first oligonucleotide and the acceptor is located on a second oligonucleotide. In a specific embodiment, one of the two FRET-labeled oligonucleotides is a primer for triamplification, and the other FRET-labeled oligonucleotide is a blocker for triamplification (see Section 5.4.2).

The oligonucleotides for use in the amplification reactions of the invention can be any suitable size, and are preferably in the range of 10–100 or 10–80 nucleotides, more preferably 20–40 nucleotides.

The oligonucleotide can be DNA or RNA or chimeric mixtures or derivatives or modified versions thereof, so long as it is still capable of priming the desired amplification reaction, or, in the case of a blocking oligonucleotide, functioning as a blocking oligonucleotide. In addition to being labeled with a MET moiety, the oligonucleotide can be modified at the base moiety, sugar moiety, or phosphate backbone, and may include other appending groups or labels, so long as it is still capable of priming the desired amplification reaction, or functioning as a blocking oligonucleotide, as the case may be.

For example, the oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

The oligonucleotides of the present invention may be derived by standard methods known in the art, e.g., by de novo chemical synthesis of polynucleotides using an automated DNA synthesizer (such as is commercially available from Biosearch, Applied Biosystems, etc.) and standard phosphoramidite chemistry; or by cleavage of a larger nucleic acid fragment using non-specific nucleic acid cleaving chemicals or enzymes or site-specific restriction endonucleases.

A preferable method for synthesizing oligonucleotides is conducted using an automated DNA synthesizer by methods known in the art. As examples, phosphorothioate oligonucleotides may be synthesized by the method of Stein et al. (1988, Nucl. Acids Res. 16:3209–3221), methylphosphonate oligonucleotides can be prepared by use of controlled pore glass polymer supports (Sarin et al., 1988, Proc. Natl. Acad. Sci. U.S.A. 85:7448–7451), etc. Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining oligonucleotide that has been separated on an acrylamide gel, or by measuring the optical density at 260 nm in a spectrophotometer.

Oligonucleotides of the invention may be labeled with donor and acceptor moieties during chemical synthesis or the label may be attached after synthesis by methods known in the art. In a specific embodiment, the following donor and acceptor MET pairs are used: a luminescent lanthanide chelate, e.g., terbium chelate or lanthanide chelate, is used as the donor, and an organic dye such as fluorescein, rhodamine or CY-5, is used as the acceptor. Preferably, terbium is used as a donor and fluorescein or rhodamine as an acceptor, or europium is used as a donor and CY-5 as an acceptor. In another specific embodiment, the donor is fluorescent, e.g. fluorescein, rhodamine or CY-5, and the acceptor is luminescent, e.g. a lanthanide chelate. In yet another embodiment, the energy donor is luminescent, e.g., a lanthanide chelate, and the energy acceptor may be nonfluorescent. Energy transfer results in a decrease in the emission of the donor.

In another specific embodiment, the donor moiety is a fluorophore. In another specific embodiment, both donor and acceptor moieties are fluorophores. Suitable moieties that can be selected as donor or acceptors in FRET pairs are set forth in Table 1.

Table 1. Suitable moieties that can be selected as donor or acceptors in FRET pairs 4-acetamido-4'-isothiocyanatostilbene-2,2' disulfonic acid
acridine and derivatives:
   acridine
   acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate (Lucifer Yellow VS)
N-(4-anilino-1-naphthyl)maleimide
anthranilamide
Brilliant Yellow
coumarin and derivatives:
   coumarin
      7-amino-4-methylcoumarin (AMC, Coumarin 120)
      7-amino-4-trifluoromethylcoumarin (Coumarin 151)
   cyanosine
4',6-diaminidino-2-phenylindole (DAPI)
5',5"-dibromopyrogallol-sulfonephthalein (Bromopyrogallol Red)
7-diethylamino-3-(4'-isothiocyanatophenyl)-4-methylcoumarin diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
eosin and derivatives:
   eosin
   eosin isothiocyanate
erythrosin and derivatives:
   erythrosin B
   erythrosin isothiocyanate
ethidium
fluorescein and derivatives:
   5-carboxyfluorescein (FAM)
   5-(4,6-dichlorotriazin-2-yl)aminofluorescein (DTAF)
   2'7'-dimethoxy-4'5'-dichloro-6-carboxyfluorescein (JOE)
   fluorescein
   fluorescein isothiocyanate
   QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
   pyrene
   pyrene butyrate
   succinimidyl 1-pyrene butyrate
Reactive Red 4 (Cibacron® Brilliant Red 3B–A)
rhodamine and derivatives:
   6-carboxy-X-rhodamine (ROX)
   6-carboxyrhodamine (R6G)
   lissamine rhodamine B sulfonyl chloride
   rhodamine (Rhod)
   rhodamine B
   rhodamine 123
   rhodamine X isothiocyanate
   sulforhodamine B
   sulforhodamine 101
   sulfonyl chloride derivative of sulforhodamine 101 (Texas Red)
   N,N,N',N'-tetramethyl-6-carboxyrhodamine (TAMRA)
   tetramethyl rhodamine
      tetramethyl rhodamine isothiocyanate (TRITC)
riboflavin
rosolic acid
terbium chelate derivatives One of ordinary skill in the art can easily determine, using art-known techniques of spectrophotometry, which fluorophores will make suitable donor-acceptor FRET pairs. For example, FAM (which has an emission maximum of 525 nm) is a suitable donor for TAMRA, ROX, and R6G (all of which have an excitation maximum of 514 nm) in a FRET pair. Primers are preferably modified during synthesis, such that a modified T-base is introduced into a designated position by the use of Amino-Modifier C6 dT (Glen Research), and a primary amino group is incorporated on the modified T-base, as described by Ju et al. (1995, Proc. Natl. Acad. Sci. USA 92:4347–4351). These modifications may be used for subsequent incorporation of fluorescent dyes into designated positions of the oligonucleotides.

The optimal distance between the donor and acceptor moieties will be that distance wherein the emissions of the donor moiety are absorbed by the acceptor moiety. This optimal distance varies with the specific moieties used, and may be easily determined by one of ordinary skill in the art using techniques known in the art. For energy transfer in which it is desired that the acceptor moiety be a fluorophore that emits energy to be detected, the donor and acceptor fluorophores are preferably separated by a distance of up to 30 nucleotides, more preferably from 3–20 nucleotides, and still more preferably from 6–12 nucleotides. For energy transfer wherein it is desired that the acceptor moiety quench the emissions of the donor, the donor and acceptor moieties are preferably separated by a distance of less than one nucleotide (e.g., on the opposite strand, complementary nucleotides of a duplex structure), although a 5 nucleotide distance (one helical turn) is also advantageous for use.

In yet another embodiment, the oligonucleotides may be further labeled with any other art-known detectable marker, including radioactive labels such as $^{32}P$, $^{35}S$, $^{3}H$, and the like, or with enzymatic markers that produce detectable signals when a particular chemical reaction is conducted, such as alkaline phosphatase or horseradish peroxidase. Such enzymatic markers are preferably heat stable, so as to survive the denaturing steps of the amplification process.

Oligonucleotides may also be indirectly labeled by incorporating a nucleotide linked covalently to a hapten or to a molecule such as biotin, to which a labeled avidin molecule may be bound, or digoxygenin, to which a labeled anti-digoxygenin antibody may be bound. Oligonucleotides may be supplementally labeled during chemical synthesis or the supplemental label may be attached after synthesis by methods known in the art.

The oligonucleotides of the invention have use in nucleic acid amplification reactions, as primers, or, in the case of triamplification, blocking oligonucleotides, to detect or measure a nucleic acid product of the amplification, thereby detecting or measuring a target nucleic acid in a sample that is complementary to a 3' primer sequence. Accordingly, the oligonucleotides of the invention can be used in methods of diagnosis, wherein a 3' primer sequence is complementary to a sequence (e.g., genomic) of an infectious disease agent, e.g. of human disease including but not limited to viruses, bacteria, parasites, and fungi, thereby diagnosing the presence of the infectious agent in a sample of nucleic acid from a patient. The target nucleic acid can be genomic or cDNA or mRNA or synthetic, human or animal, or of a microorganism, etc. In another embodiment that can be used in the diagnosis or prognosis of a disease or disorder, the target sequence is a wild type human genomic or RNA or cDNA sequence, mutation of which is implicated in the presence of a human disease or disorder, or alternatively, can be the mutated sequence. In such an embodiment, optionally, the amplification reaction can be repeated for the same sample with different sets of primers that amplify, respectively, the wild type sequence or the mutated version. By way of example, the mutation can be an insertion, substitution, and/or deletion of one or more nucleotides, or a translocation.

5.1.1. HAIRPIN PRIMERS

The present invention provides oligonucleotide primers that form a hairpin structure in which MET will occur when the primer is not incorporated into the amplification product.

Accordingly, in a specific embodiment, the invention provides a hairpin primer that is an oligonucleotide comprising, or alternatively consisting of, the following contiguous sequences in 5' to 3' order: (a) a first nucleotide sequence of 6–30 nucleotides, wherein a nucleotide within said first nucleotide sequence is labeled with a first moiety selected from the group consisting of a donor moiety and an acceptor moiety of a molecular energy transfer pair, wherein the donor moiety emits energy of one or more particular wavelengths when excited, and the acceptor moiety absorbs energy at one or more particular wavelengths emitted by the donor moiety; (b) a second, single-stranded nucleotide sequence of 3–20 nucleotides; (c) a third nucleotide sequence of 6–30 nucleotides, wherein a nucleotide within said third nucleotide sequence is labeled with a second moiety selected from the group consisting of said donor moiety and said acceptor moiety, and said second moiety is the member of said group not labeling said first nucleotide sequence, wherein said third nucleotide sequence is sufficiently complementary in reverse order to said first nucleotide sequence for a duplex to form between said first nucleotide sequence and said third nucleotide sequence such that said first moiety and second moiety are in sufficient proximity such that, when the donor moiety is excited and emits energy, the acceptor moiety absorbs energy emitted by the donor moiety; and (d) at the 3' end of said oligonucleotide, a fourth, single-stranded nucleotide sequence of 8–40 nucleotides that comprises at its 3' end a sequence sufficiently complementary to a preselected target sequence so as to be able to prime synthesis by a nucleic acid polymerase of a nucleotide sequence complementary to a nucleic acid strand comprising said target sequence; wherein when said duplex is not formed, said first moiety and said second moiety are separated by a distance that prevents molecular energy transfer between said first and second moiety.

In a specific embodiment wherein the donor and acceptor moieties are a FRET pair, separation of the first and second moiety by a distance that prevents FRET is observed by the failure of the second moiety to quench the fluorescence of the first moiety (when the second moiety is a quencher), or the failure of the second moiety to absorb the fluorescence of the first moiety and then itself to fluoresce (when the second moiety is a fluorophore).

In a specific embodiment, the second nucleotide sequence (the loop structure) and/or the first nucleotide sequence (of the duplex) and/or third nucleotide sequence (of the duplex) do not contain a sequence complementary to the target sequence. Alternatively, the second nucleotide sequence and/or the first nucleotide sequence and/or the third nucleotide sequence or any portion of the foregoing sequences may also contain a sequence complementary to the target sequence.

In a preferred embodiment, a primer forms a hairpin structure in which the energy of a donor fluorophore is quenched by a non-fluorescing acceptor moiety when the primer is not incorporated into the amplification product. One of ordinary skill in the art can easily determine, from the known structures and hydrophobicities of a given FRET pair, the steric arrangement that will bring the pair into closest proximity for MET.

In a specific embodiment, the hairpin primer comprises four parts (FIG. 1): Part (d) is a 3' terminal sequence and comprises a sequence complementary to the target sequence; it is a primer for DNA polymerase. Part (c) is a first stem sequence on the 5' end of the primer sequence. Part (b) forms a single-stranded loop of nucleotides. Part (a) is a second stem sequence, which is complementary to the first stem sequence. Parts (a), (b), and (c) or portions thereof may or may not be complementary to the target DNA to be amplified. Part (d) is preferably 8–30 nucleotides long; Part (c) is preferably 6–30 nucleotides long; Part (b) is preferably 3–20 nucleotides long, and most preferably, 4–6 nucleotides long.

The first stem sequence, Part (c), contains the donor fluorophore and the second stem sequence, Part (a), contains the acceptor (e.g., quencher), or it can be opposite. In a non-incorporated hairpin primer, the emission of the donor will be transferred to the acceptor, since the two moieties will be in close proximity to each other when two stem sequences are in duplex.

The donor and acceptor moieties can be located on either terminal nucleotides of the hairpin stem (duplex region), or internally located. Thus, in one embodiment of the invention, the donor and acceptor (or quencher) moieties are respectively located on the 5' end of the hairpin primer sequence that is complementary to the target and located on the complementary nucleotide residue on the hairpin stem (FIG. 1), or vice versa. Each moiety may alternatively be located on a nucleotide internal within a complementary stem sequence. Alternatively, one of the moieties may be located on an internal nucleotide and the other on the terminal nucleotide at the 5' end. One or both of the moieties may alternatively be located at the other end of the duplex region.

Preferably, donor and acceptor moieties are attached to the complementary strands of the stem, one moiety on the 5' end and the other moiety 5 bp apart on the complementary strand. For example, the two moieties can be offset by a 5 bp (180°) turn of the double helix formed by the two complementary strands of the stem, and will therefore be in closest proximity sterically, and the emission of the donor will be transferred to (and, e.g., quenched by) the acceptor.

Alternatively, the two moieties can be on complementary strands of the stem separated by a distance of less than 1 nucleotide (3.4 Å) when the hairpin is in the closed configuration. Most preferably, the two moieties are on complementary nucleotides on the stem, directly opposite from one another when the hairpin is in the closed configuration.

When a hairpin primer is linearized, the donor moiety must be separated from the acceptor (e.g., quencher) moiety by an intervening sequence that is long enough to substantially prevent MET. Where a FRET pair that consists of donor and acceptor fluorophores is used, the two FRET moieties are separated by an intervening sequence, comprising (a) at least a portion of the first stem sequence, (b) the loop, and (c) at least a portion of the second stem sequence; the intervening sequence being preferably 15–25 nucleotides in length, and more preferably, 20 nucleotides in length.

In one embodiment, the acceptor moiety is a fluorophore that will re-emit the energy provided by the donor at a different wavelength; that is, when the primer is in the closed state, emissions from the acceptor, but not from the donor, will be detected. In a preferred embodiment, the acceptor moiety is a quencher and absorbs the energy emitted by the donor without fluorescing. In either case, the fluorescence of donor may be detected only when the primer is in the linearized, open state i.e., is incorporated into a double-stranded amplification product. Energy transfer in this state will be minimal and the strong emission signal from the donor will be detected.

Figure 3:
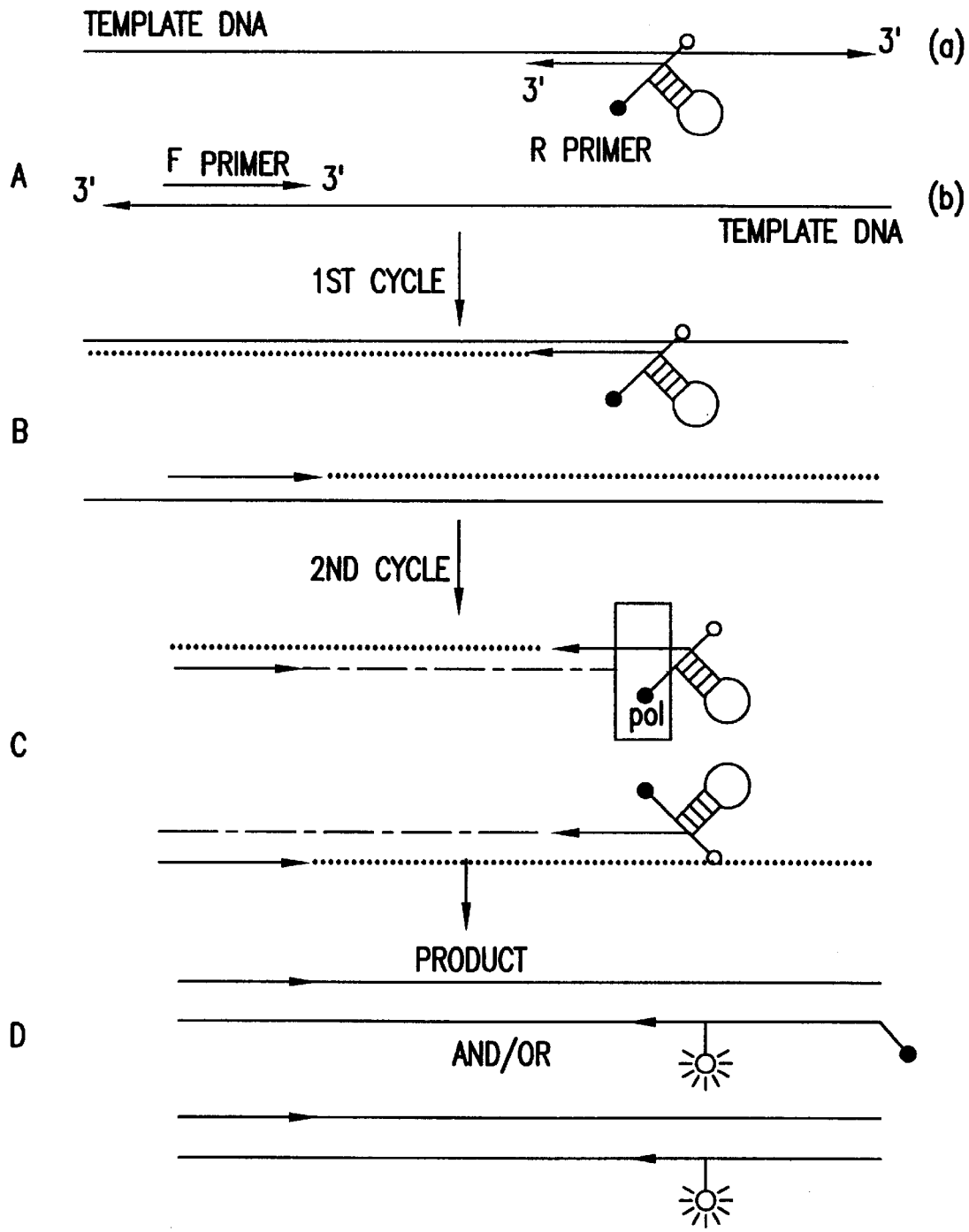

A critical aspect of the invention is that the transition from the closed to the open state occurs only during amplification. FIGS. 2 and 3 schematically illustrate the use of the hairpin primers of the present invention in PCR. In FIG. 2, the DNA polymerase used in PCR lacks 5'-3' exonuclease activity, whereas in FIG. 3, it has 5'-3' activity. For PCR, either one or both PCR primers can be a hairpin primer.

In FIGS. 2 and 3, (a) and (b) are two complementary strands of the target sequence to be amplified and "R" and "F" are the reverse and forward primers, respectively, for PCR amplification. By way of example and not limitation, the reverse hairpin primer is designed such that there is a donor fluorophore and quencher incorporated into it. Reverse hairpin primer that is not incorporated into the PCR product will have fluorophore and quencher in close proximity; thus the fluorescence from the free reverse primer will be quenched. See Section 5.2.1 infra for methods of use of hairpin primers in PCR.

5.1.1.1. UNIVERSAL HAIRPINS AND HAIRPIN PRIMERS

In one embodiment, the oligonucleotide of the invention is a "universal" hairpin that can be ligated, either chemically (e.g., using cyanogen bromide) or enzymatically (e.g., using ligase) to any selected primer sequence and used to amplify a target nucleic acid sequence that contains the complement of the primer sequence. The invention provides a "universal" hairpin that is an oligonucleotide, the nucleotide sequence of which consists of the following contiguous sequences in 5' to 3' order: (a) a first single-stranded nucleotide sequence of 1 to 10 nucleotides; (b) a second nucleotide sequence of 2–30 nucleotides, wherein a nucleotide within said first nucleotide sequence or said second nucleotide sequence is labeled with a first moiety selected from the group consisting of a donor moiety and an acceptor moiety of a molecular energy transfer pair, wherein the donor moiety emits energy of one or more particular wavelengths when excited, and the acceptor moiety absorbs energy at one or more particular wavelengths emitted by the donor moiety; (c) a third, single-stranded nucleotide sequence of 3–20 nucleotides; (d) a fourth nucleotide sequence of 2–30 nucleotides, wherein a nucleotide within said fourth nucleotide sequence is labeled with a second moiety selected from the group consisting of said donor moiety and said acceptor moiety, and said second moiety is the member of said group not labeling said first or second nucleotide sequence, wherein said fourth nucleotide sequence is sufficiently complementary in reverse order to said second nucleotide sequence for a duplex to form between said second nucleotide sequence and said fourth nucleotide sequence such that said first moiety and second moiety are in sufficient proximity such that, when the donor moiety is excited and emits energy, the acceptor moiety absorbs energy emitted by the donor moiety.

Figure 4:
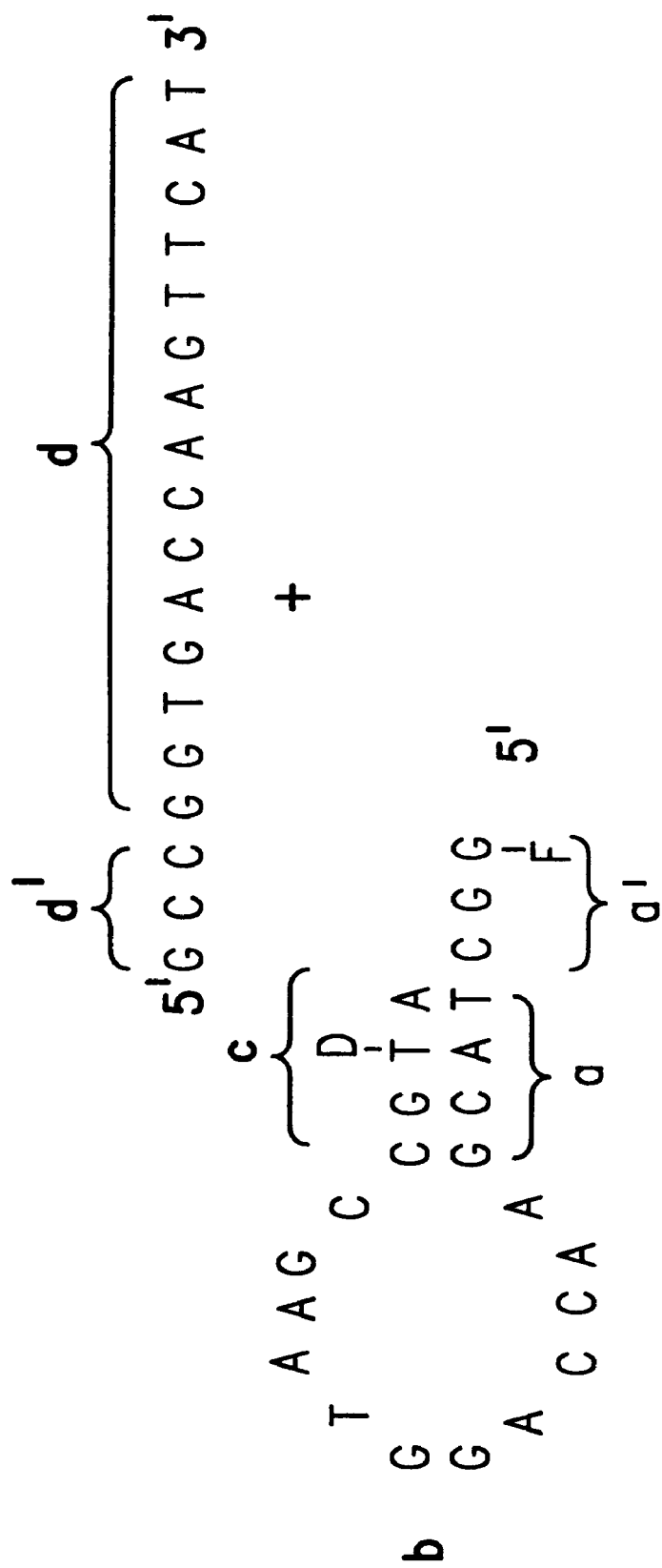

An example of a universal hairpin is shown in FIG. 4. The universal hairpin of the invention comprises a first stem sequence on the 3' end (2–30 nucleotides long, preferably 4–6 nucleotides long), a loop (3–20 nucleotides long, preferably 4–6 nucleotides long), a second stem sequence essentially complementary to the first stem sequence (2–30 nucleotides long, preferably 4–6 nucleotides long), and a 5' single-stranded cohesive ("sticky") end sequence (e.g., 1–10 nucleotides long, preferably 3–4 nucleotides long). In a specific embodiment, the "sticky" end sequence is 5'GGC-3'.

Selected primer sequences that are complementary to a target DNA sequence and that are suitable for ligation to the universal hairpin may be derived by standard methods known in the art, e.g., by de novo chemical synthesis of polynucleotides using an automated DNA synthesizer and standard phosphoramidite chemistry; or by cleavage of a larger nucleic acid fragment using non-specific nucleic acid cleaving chemicals or enzymes or site-specific restriction endonucleases.

In order to join a universal hairpin to the selected primer sequence, the selected primer sequence should contain a cohesive sequence on the 5' end essentially complementary to the cohesive sequence of the universal hairpin (FIG. 4). In one embodiment, the 5' cohesive end on the selected primer sequence is chemically synthesized to complement the 5' cohesive end on the universal hairpin. In another embodiment, the 5' cohesive end on the selected primer sequence is produced by the staggered cut of a restriction endonuclease.

A labeling moiety on the universal hairpin must not be situated so as to substantially interfere with subsequent ligation at its 3' end to the selected primer sequence. Thus, preferably, a labeling moiety is not located on the 3' terminal nucleotide of the universal hairpin (FIG. 4). At the 5' end of the hairpin, a labeling moiety may be located either on the terminal nucleotide at the 5' end (as shown in FIG. 4) or on a nucleotide internal to the 5' end.

The donor (fluorescent) and acceptor (quencher) moieties of a universal hairpin such as shown in FIG. 4 must be separated by a distance such that the emissions of the donor moiety are quenched by the acceptor moiety. Preferably, the donor and acceptor moieties are separated by a distance of less than 1 nucleotide (3.4 Å) when the hairpin is in the closed configuration.

In one embodiment, the two FRET moieties are separated by an intervening sequence, comprising a portion of the first stem sequence, the loop, and a portion of the second stem sequence, that is preferably 15–25 nucleotides in length. More preferably, the loop on the universal hairpin is long enough provide a distance of 20 nucleotides between a donor (e.g., FAM) and a quencher (e.g., DABCYL) when the hairpin is in the "open" configuration.

FIG. 4 gives a schematic example of a selected target sequence (8–40 nucleotides, preferably ~15 nucleotides) and a universal hairpin prior to their ligation to each other.

In another embodiment, a universal hairpin primer of the invention is used, that contains a 3' sequence that, instead of being complementary to a preselected target nucleic acid sequence to be amplified, is identical to the 5' single stranded sequence of another primer used in the amplification reaction. The 3' sequence of the other primer is complementary to the target nucleic acid sequence, while its 5' identical sequence is not complementary to the target nucleic acid sequence (see by way of example, FIG. 5 and Section 5.2.1).

5.1.2. LINEAR OLIGONUCLEOTIDES

In another embodiment, the oligonucleotide primers are both linear molecules that cannot form a hairpin configuration. In a specific embodiment, a donor-acceptor FRET pair are both fluorophores located on the same, single-stranded oligonucleotide primer, within distance of each other so that FRET can occur. In this embodiment, the double-labeling with a FRET pair increases the separation between the excitation and the emission frequencies of a label. This increased separation decreases background fluorescence that can interfere with accurate quantitation of the emission signal.

For example, in a specific embodiment, fluorescein may serve as the donor moiety and rhodamine as the acceptor moiety. Fluorescein exhibits peak excitation at 488 nm, but the excitation spectrum is broad and it exhibits some excitation at its emission frequency at 520 nm. This contributes to an emission artifact at 520 nm that decreases the accuracy and sensitivity of quantitative spectrophotometry when using fluorescein as a single label. If a fluorescein moiety is used as a donor and a rhodamine moiety as an acceptor (rhodamine has peak excitation at 520 nm and peak emission at 605 nm), however, excitation will occur at 488 nm and emission will occur at 605 nm, greatly decreasing background artifact.

In another specific embodiment, the donor moiety is located on a first oligonucleotide primer and the acceptor is located on a second, complementary oligonucleotide. In a preferred aspect of this embodiment, one of the two FRET-labeled primers is a primer for triamplification, and the other FRET-labeled oligonucleotide is a blocking oligonucleotide (blocker) for triamplification.

5.2. METHODS FOR DETECTION OF AMPLIFICATION PRODUCTS USING HAIRPIN PRIMERS

In a specific embodiment of a hairpin primer of the invention, the acceptor moiety is a fluorophore or quencher that absorbs the energy transmitted by the donor moiety. In a preferred embodiment, the acceptor moiety is a quencher; the primer is configured such that the acceptor moiety on free primer quenches the fluorescence from the donor. When the primer is incorporated into the amplification product, its configuration changes, quenching is eliminated, and the fluorescence of the donor moiety is detected.

The detection method of the present invention may be applied to any amplification system in which an oligonucleotide is incorporated into an amplification product e.g., polymerase chain reaction (PCR) systems (U.S. Pat. Nos. 4,683,195 and 4,683,202), triamplification systems (TriAmp™, Oncor Inc.; U.S. application Ser. No. 08/461,823, filed Jun. 5, 1995, which is incorporated by reference herein in its entirety; PCT International Publication No. WO 9417206 A1, dated Aug. 4, 1994; PCT International Publication No. WO 9417210 A1, dated Aug. 4, 1994), nucleic acid sequence-based amplification (NASBA) systems (U.S. Pat. No. 5,409,818; Compton, 1991, Nature 350:91–92), and strand displacement amplification (SDA) systems (Walker et al., 1992, Nucl. Acids Res. 20:1691–1696). As a result of amplification, the hairpin primers are incorporated into the double-stranded polynucleotide amplification products.

In a specific embodiment, the hairpin primers are used to prime an amplification in situ, on samples of preserved or fresh cells or tissues (see, e.g., Nuovo, 1997, *PCR In Situ Hybridization: Protocols and Applications, Third Edition*, Lippincott-Raven Press, New York).

Although various specific embodiments involving a FRET pair are described hereinbelow as involving a preferred FRET pair consisting of a donor fluorophore moiety and a quencher acceptor moiety, it will be understood that such embodiments could also have been described in terms of the acceptor moiety being a fluorophore rather than a quencher.

5.2.1. METHODS OF USE OF HAIRPIN PRIMERS IN POLYMERASE CHAIN REACTION (PCR)

In one embodiment, the hairpin primers of the invention are used to prime a polymerase chain reaction (PCR), thereby becoming incorporated into the amplification product (examples being illustrated in FIGS. 2 and 3A–D).

The PCR primers contain hairpin structures on their 5' ends with FRET donor and acceptor moieties located in close proximity (30 nucleotides or less) on the hairpin stem. The primers are designed in such a way that a fluorescent signal from the donor moiety is generated only when the primers are incorporated into an amplification product. The modified hairpin primers do not interfere with the activity of DNA polymerase, and in a preferred aspect, thermostable Pfu polymerase or Taq polymerase can be used. The forward and/or reverse primers can be hairpin primers.

In the example shown in FIG. 3, the hairpin primer has a quencher on its 5' terminal nucleotide, and contains a donor fluorophore on the opposite strand of its duplex, the fluorophore and quencher being a FRET pair. In the first cycle of PCR (FIG. 3B), both primers will hybridize to the respective target strands and will be extended by DNA polymerase. In the second cycle (FIG. 3C) the extended product from the reverse primer will become a template for the forward primer and extended product from the forward primer will become a template for the reverse primer. When the forward primer is extended to the 5' end of the hairpin structure, either of two things can happen, depending on the DNA polymerase used: either the 5'-3' exonuclease activity of the DNA polymerase will hydrolyze the 5' nucleotides with quencher, and/or DNA polymerase will displace the 5'-end of the hairpin and copy the template. In both cases, the quencher and the fluorophore will be separated from each other and a signal will be generated (FIG. 3D).

Hairpin primers may be employed in any amplification method in which the hairpin primer is not complementary to any other oligonucleotide used in the reaction mixture, and in which the hairpin primer is incorporated into a double-stranded DNA amplification product, e.g., PCR, triamplification, nucleic acid sequence-based amplification (NASBA), and strand displacement amplification (SDA) (see infra). Thus, for example, in triamplification involving the use of a hairpin primer, the other, non-hairpin primer is complementary to the blocking oligonucleotide.

In another specific embodiment (FIG. 5), a universal hairpin primer is used, along with two selected linear primers, Primer 1 and Primer 2, to prime a PCR. In this case, the universal hairpin primer is incorporated into the amplification product and is not ligated to one of the two linear primer sequences. In this embodiment, the 3' sequence of the universal hairpin primer is identical to the 5' sequence of one of the pair of linear forward and reverse primers used in the amplification, and this 5' sequence (sequence "A" on Primer 2 in FIG. 5) must not be complementary to the target sequence.

During the first cycle of PCR, Primer 1, which is complementary to a target DNA (+) strand is extended. Primer 2 has a 3' portion that has a sequence complementary to the target (−) strand and a 5' portion, designated "A" in FIG. 5, that has a sequence that is not complementary to the target. Sequence A is preferably 10–25 nucleotides, and more preferably, 12–15 nucleotides in length.

During the second cycle, the product of the extension of Primer 2 (shown by the arrow) becomes a template for Primer 1. Primer 1 is extended and the amplification product now includes a sequence, designated "A'," complementary to sequence A.

During the third cycle, the A sequence of the hairpin primer anneals to the A' sequence of the amplification product from the previous cycle.

During the fourth cycle, the extended hairpin primer becomes a template for Primer 1. During the extension of Primer 1, the hairpin unfolds, the quencher and fluorophore are separated, and a fluorescent signal is emitted from the amplification product. In a similar way, the method can be applied to triamplification. In this case, the hairpin primer is the primer not complementary to the blocker.

5.2.1.1. METHODS OF USE OF HAIRPIN PRIMERS IN ALLELE-SPECIFIC PCR (ASP)

In another embodiment, primers of the invention are used to prime an allele-specific PCR (ASP). In this embodiment, one or both amplification primers may be hairpin primers. In ASP, a target DNA is preferentially amplified if it is completely complementary to the 3' end of a PCR amplification primer. The 3' end of the hairpin primer should terminate at or within one or 2 bases of a known mutation site in a gene (target DNA) to which it has a complementary sequence. Under the appropriate reaction conditions, the target DNA is not amplified if there is a base mismatch (e.g., a nucleotide substitution caused by a mutation) or a small deletion or insertion, at the 3' end of the primer (Okayama et al, 1989, J. Lab. Clin. Med. 114:105–113; Sommer et al., 1992, BioTechniques 12:82–87). Thus, ASP can be used to detect the presence or absence of at least a single mismatch between the hairpin sequence that is complementary to the preselected target sequence and a nucleic acid in the sample; amplification indicates the absence of such a single mismatch.

5.2.2. METHODS OF USE OF HAIRPIN PRIMERS IN TRIAMPLIFICATION

5 5.2.2.1. GENERAL STEPS IN TRIAMPLIFICATION REACTIONS

Both hairpin primers and linear primers (see Sections 5.2 and 5.4) can be used in triamplification reactions.

Figure 6:
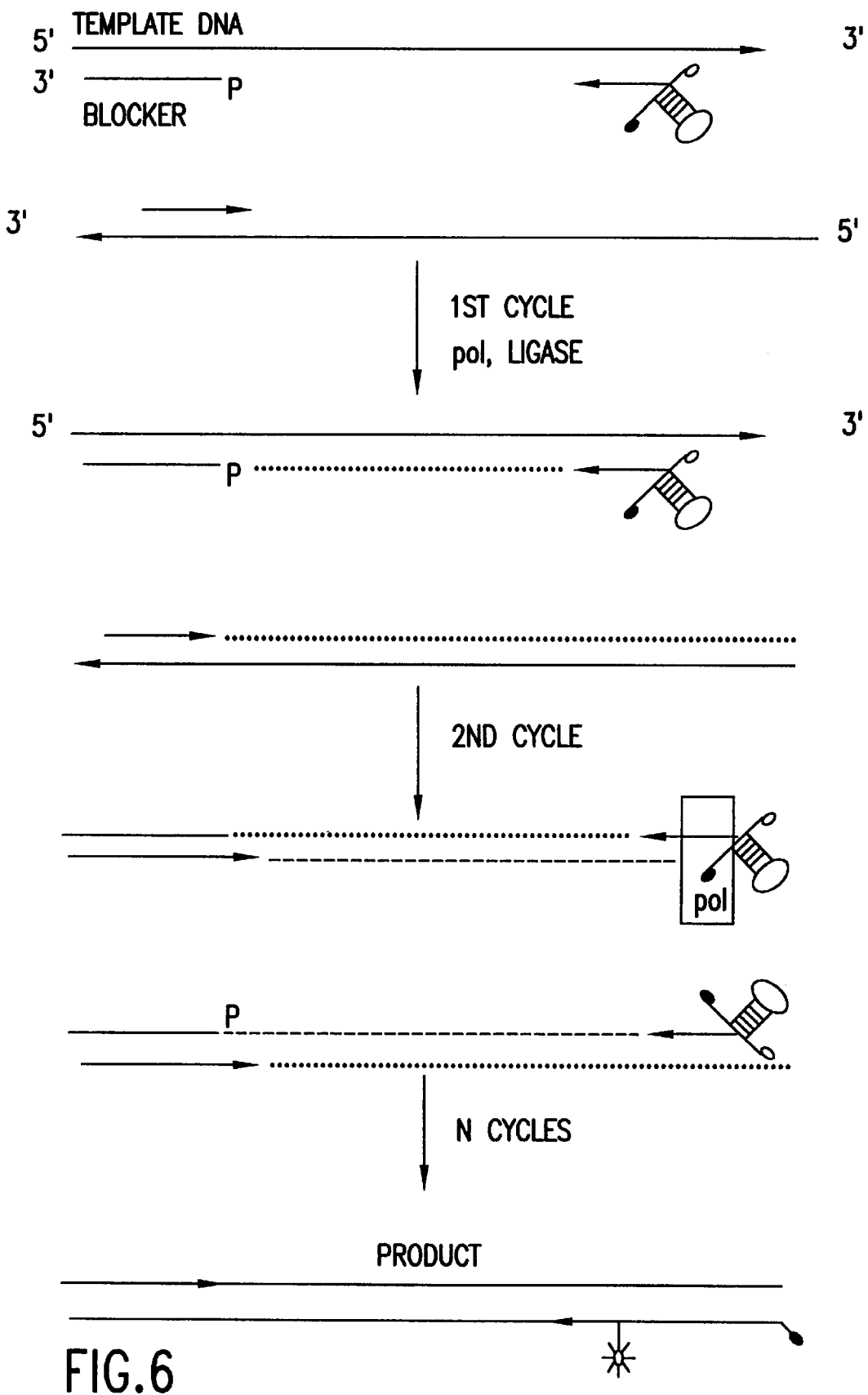

A triamplification reaction is based on three oligonucleotides: two primers and a blocking oligonucleotide (blocker). An example is shown in FIG. 6. The two primers, a forward and a reverse "extending" primers, are complementary to the two strands of a selected target (template) DNA. A third oligonucleotide, a blocker, is partially complementary to one of the two extending primers. Triamplification utilizes two thermostable enzymes: DNA polymerase and DNA ligase. During the repeated steps of polymerization and ligation, one of the extended primers is ligated to the blocker.

In one version of triamplification (the "gap" version), the forward oligonucleotide is a primer substantially complementary to a first segment at a first end of the target sequence to be amplified. The reverse oligonucleotide is a primer substantially complementary to a second segment at a second end of the target nucleic acid sequence on a different strand of the target nucleic acid. The third oligonucleotide (the "blocker" or "blocking oligonucleotide") is substantially complementary to at least a portion of the forward or reverse primer.

Figure 7:
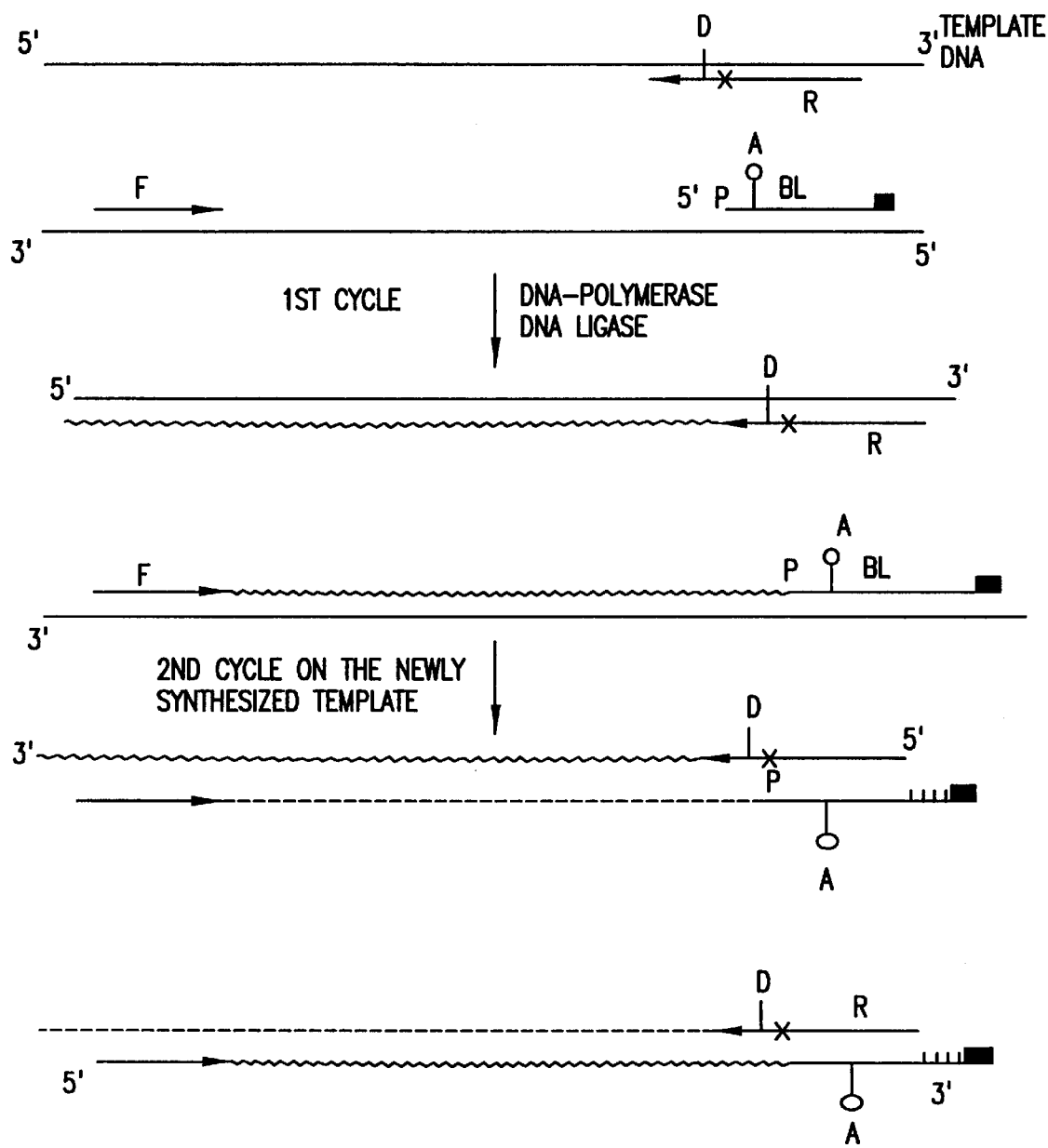

A schematic illustration of gap triamplification, which consists of repeated elongation and ligation of the amplification product, is shown in FIG. 7. Blocker may be used at the same or higher concentration than the concentration of forward and reverse primers. Preferably, blocker is used at a 1.2 to 2-fold higher concentration than the concentration of forward and reverse primers. The primer complementary to the blocker preferably is modified to prevent strand displacement during amplification; in a preferred embodiment, this primer contains 2'-O-methyl at the position complementary to the 5' end of the blocker in order to prevent strand displacement.

In the case where linear primers of the invention are used (Section 5.4), the blocker is preferably modified in order to protect it from exonuclease hydrolysis (which is used with amplification methods using linear, but not hairpin primers) and from undesirable extension during amplification. In a preferred embodiment, the blocker has biotin on its 3' end in order to protect it from exonuclease hydrolysis and from undesirable extension during amplification.

An alternate version of triamplification, the "non-gap version," is substantially similar to the gap version described above, with the difference that the 5' end of the forward primer is adjacent to the 3' end of the reverse primer.

5.2.2.2. USE OF HAIRPIN PRIMERS IN TRIAMPLIFICATION REACTIONS

In one embodiment of the invention, hairpin primers are used to prime a triamplification reaction, thereby becoming incorporated into the amplification product. When using hairpin primers in triamplification, the hairpin structure is part of whichever primer, either the forward or the reverse primer, that is not complementary to the blocker (FIG. 6). It cannot be used on the primer complementary to the blocker, because, in this case, the blocker will interfere with the formation of the hairpin on the primer that is not incorporated into the amplification product.

The hairpin primer is preferably labeled with a FRET donor-acceptor pair on its stem. During the first cycle of triamplification, the hairpin primer will be extended and ligated to the blocker. During the second cycle, the extended hairpin primer will become a template for the second primer. In the course of extension of the second primer, the hairpin will open, the quencher will be separated from the fluorophore and the donor will emit a fluorescence signal.

5.2.3. METHODS OF USE OF HAIRPIN PRIMERS IN NUCLEIC ACID SEQUENCE-BASED AMPLIFICATION (NASBA)

Figure 9:
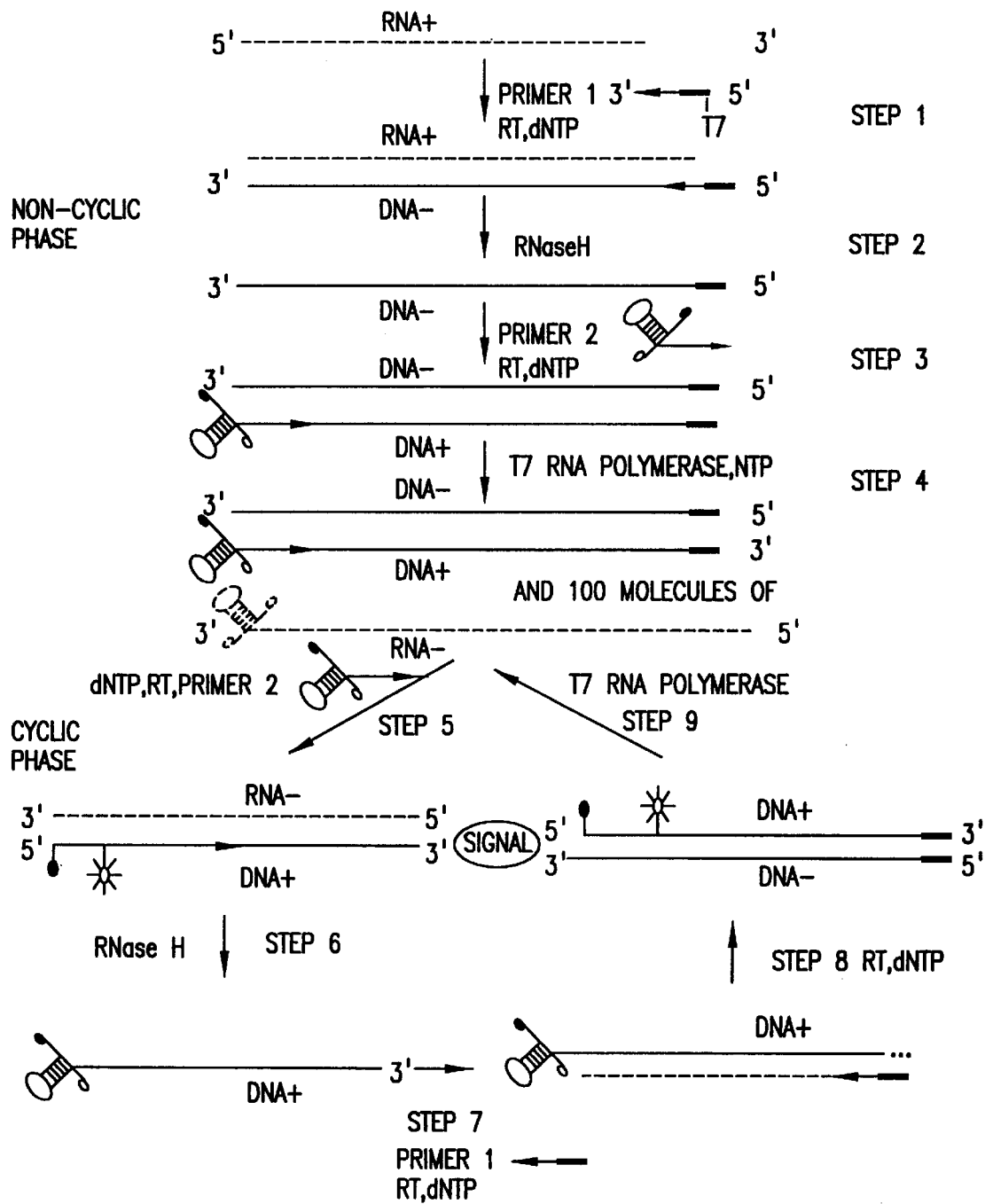

The primers of the invention may be used to prime nucleic acid sequence-based amplification (NASBA), an example of which is shown in FIG. 9. NASBA uses continuous cycling of reverse transcription and RNA transcription reactions and is conducted at one temperature. It uses three enzymes (reverse transcriptase, RNase H, and T7 RNA polymerase). In one embodiment, the method uses two primers, one of which is a hairpin primer of the invention that is labeled with FRET donor and acceptor (e.g., quencher) moieties. In an alternative embodiment, both primers are hairpin primers of the invention.

Primer 1 has preferably about 20 bases on its 3' end that are complementary to a target RNA and a promoter sequence 5' to the target-complementary sequence that is recognized by T7 RNA polymerase. Primer 2 is a hairpin primer of the invention that is complementary to the RNA (−) sequence and has a hairpin structure on its 5' end that is labeled with energy transfer moieties such as is illustrated by way of example in FIG. 9.

The non-cycling NASBA phase proceeds as follows (FIG. 9). In Step 1, Primer 1 anneals to the RNA target sequence. Reverse transcriptase uses dNTPs to extend the 3' end of the Primer 1, forming a RNA/DNA hybrid. In Step 2, RNase H hydrolyzes the RNA strand of the hybrid. In Step 3, hairpin Primer 2 anneals to the single DNA strand remaining from the hybrid. Reverse transcriptase synthesizes the second DNA strand, rendering the promoter region double-stranded. In Step 4, the third enzyme in the mixture, T7 RNA polymerase, binds to the promoter sequence and generates up to 100 RNA copies from each template molecule.

The cycling NASBA phase then proceeds as follows. In Step 5, hairpin Primer 2 binds to the RNA template through its 3' end priming sequence, and reverse transcriptase extends it and generates a RNA/DNA hybrid. The 5' end of the hairpin is displaced and copied as a result of replication. The quencher and the fluorophore are now spaced far enough apart that the fluorophore is no longer quenched and its fluorescence will be detectable. In Step 6, RNase H hydrolyzes the RNA strand. The resulting single-stranded DNA is now "silent" (fluorescence is quenched) because the hairpin structure is formed again. In Step 7, Primer 1 binds to the single-stranded DNA. Reverse transcriptase binds to the 3' ends of both the primer and the DNA template. In Step 8, the 3' end of the single-stranded DNA is extended, yielding a double-stranded, transcriptionally active promoter. Simultaneously, the 3' end of Primer 1 is extended. The 5' end of the hairpin is displaced and copied as a result of replication. The quencher and the fluorophore are now spaced far enough apart that the fluorophore is no longer quenched and its fluorescence will be detectable. In Step 9, T7 RNA polymerase generates multiple RNA copies from each template molecule.

Hence in this embodiment, the amplification products of steps 5 and 8 will have incorporated the FRET-labeled hairpin primer and will give a fluorescent signal during the cyclic phase.

In the above example, a hairpin primer is employed in the NASBA process as described by Compton (1991, Nature 350:91–92). However, if polymerase-specific 5'-3' exonuclease activity is present in addition to reverse transcriptase, T7 RNA polymerase and RNase H, the 5' end of the hairpin-primer will be hydrolyzed during replication. A fluorescence signal will be generated not only at steps 5 and 8, but also at steps 6 and 7, since there will be no quencher attached to the DNA template.

5.2.4. METHODS OF USE OF HAIRPIN PRIMERS IN STRAND DISPLACEMENT AMPLIFICATION (SDA)

The hairpin primers of the invention may be used in strand displacement amplification (SDA) of a double-stranded DNA target. The forward and/or reverse primers can be hairpin primers. SDA depends on the continuous cycling of nicking and polymerization/displacement steps and is conducted at one temperature.

Figure 10:
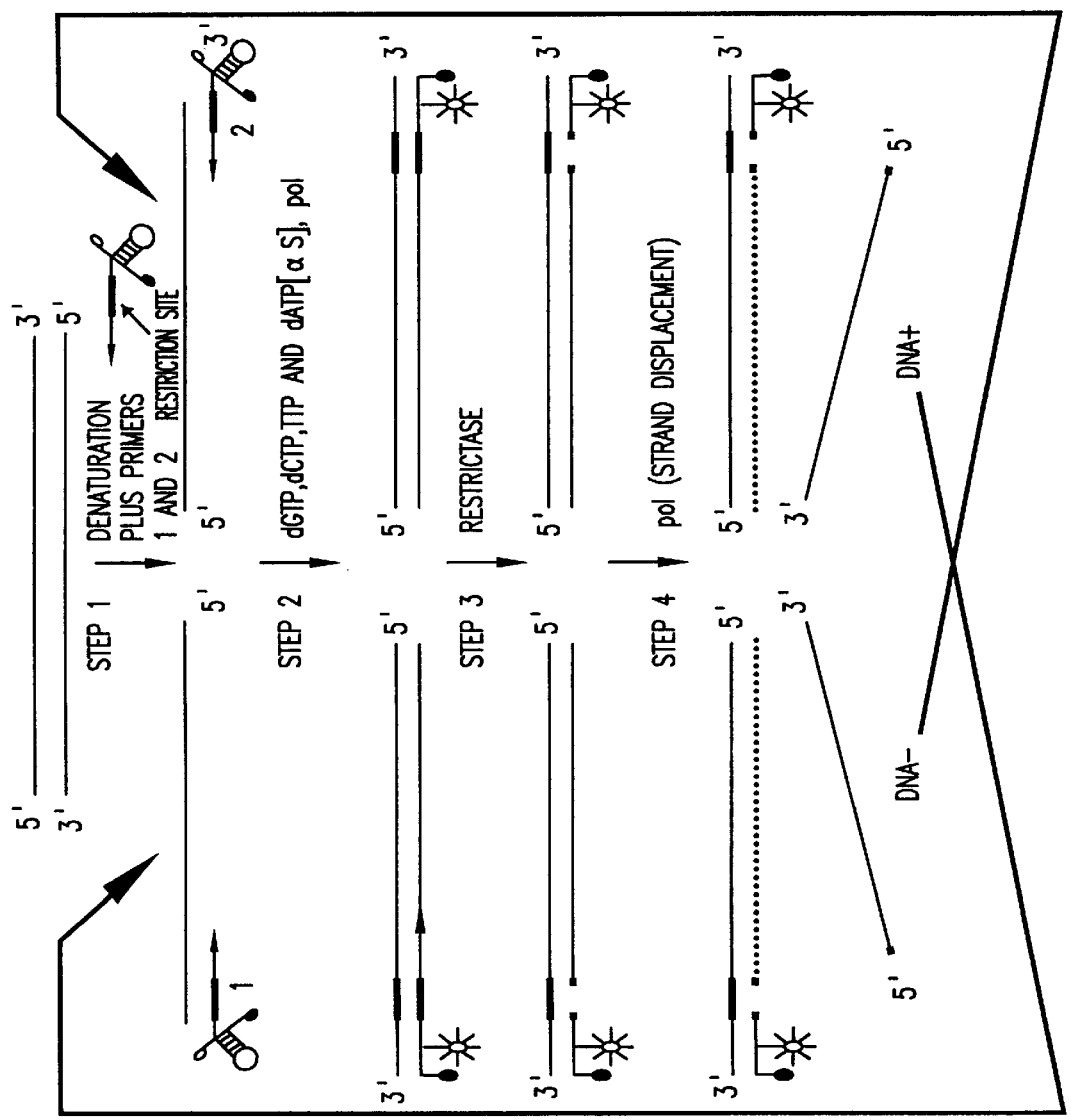

In a specific embodiment (FIG. 10), Primer 1 and Primer 2 are both hairpin primers of the invention. Each has a single-stranded priming sequence on the 3' end, a recognition site for the restriction endonuclease, and a FRET-labeled hairpin structure on the 5' end.

SDA proceeds as follows. In Step 1, the target DNA is denatured and Primer 1 and Primer 2 anneal through their 3' sequences. In Step 2: The 3' ends of the primers are extended using dNTPs, one of which is a 5'-[α-thio]triphosphate. A double stranded restriction site is formed with one modified strand (the thio-modified strand is resistant to endonuclease hydrolysis). At the same time, the 5' end of the hairpin primer is displaced and copied as a result of replication. The quencher and the fluorophore are now spaced far enough apart that the fluorophore is no longer quenched and its fluorescence will be detectable. In Step 3, the non-modified strand of the double-stranded DNA is nicked by the restriction endonuclease. In Step 4, DNA polymerase that lacks 5'-3' exonuclease activity, preferably Bst DNA polymerase Large Fragment ("Bst LF polymerase"), extends the 3' end of the nick, displacing the single-stranded DNA target, which will go through the same cycle again.

Hence in this embodiment, the amplification products of Steps 2, 3 and 4 will have incorporated the FRET-labeled hairpin primer and will give a fluorescent signal.

5.2.5. METHODS OF USE OF HAIRPIN PRIMERS IN TELOMERIC REPEAT AMPLIFICATION PROTOCOLs (TRAPs)

Telomeres are specific structures found at the ends of chromosomes in eukaryotes. In human chromosomes, the telomeres consist of thousands of copies of 6 base repeats (TTAGGG) (Blackburn and Szostak, 1984, Ann. Rev. Biochem. 53:163); Blackburn, 1991, Nature 350: 569; Zakitan, 1989, Ann. Rev. Genet. 23:579). Telomeres stabilize chromosome ends. Broken chromosomes lacking telomeres undergo fusion, rearrangement, and translocation (Blackburn, 1991, Nature 350:569). In somatic cells, telomere length is progressively shortened with each cell division both in vivo and in vitro (Harley, et al., Nature 345:458; Hastie, et al., 1990, Nature 346:866, Lindsey, et al., 1991, Mutat. Res. 256:45; Counter, et al., EMBO J. 11:1921) due to the inability of the DNA polymerase complex to replicate the very 5' end of the lagging strand.

Telomerase is a riboprotein that synthesizes and directs the telomeric repeats onto the 3' end of existing telomeres using its RNA component as a template. Telomerase activity has been shown to be specifically expressed in immortal cells, cancer and germ cells (Kim, et al., 1994, Science 266:2011; Shay and Wright, 1996, Current Opinion in Cancer 8:66–71), where it compensates for telomere shortening during DNA replication and thus stabilizes telomere length. These observations have led to a hypothesis that telomere length may function as a "mitotic clock" to sense cell aging and eventually signal replicative senescence or programmed cell death (Shay and Wright, 1996, Current Opinion in Cancer 8:66–71; Harley, 1991, Mutat. Res 256:271; Greider, 1990, BioEssays 12:363; Piatyszek, et al., Methods in Cell Science 17:1).

The TRAP (telomeric repeat amplification protocol) assay is a highly sensitive in vitro system that utilizes PCR and is used for the detection of telomerase activity. Telomerase-positive cells may be detected by employing the hairpin primers of the invention with a TRAP assay, e.g., a TRAP-eze™ (Oncor, Inc., Gaithersburg, Md.) assay.

Figure 31:
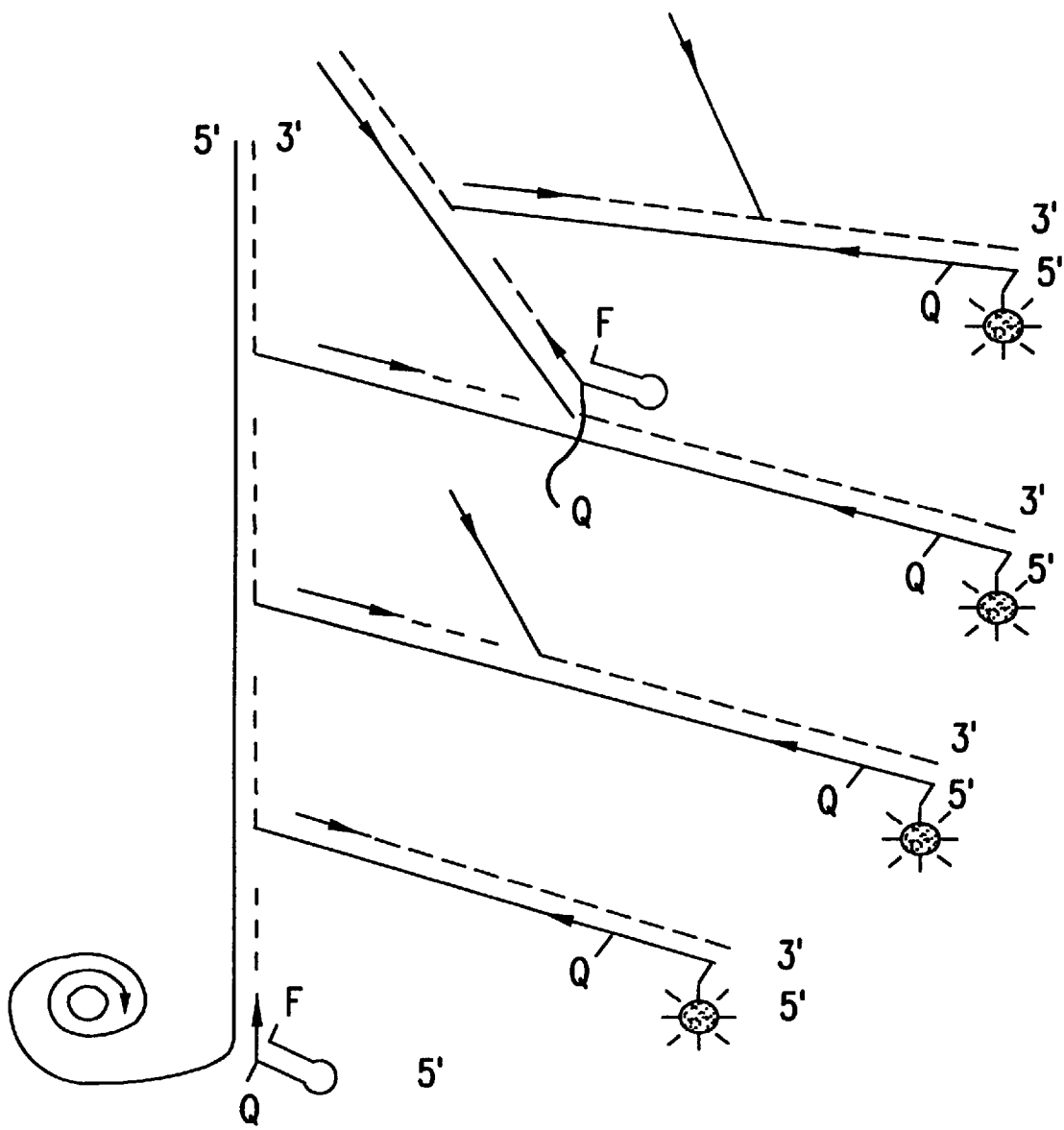

A TRAP assay is preferably carried out following the instructions provided with the TRAP-eze™ kit (Oncor, Inc., Gaithersburg, Md.). The TRAP-eze™ assay is a one buffer, two enzyme system utilizing PCR. As will be apparent, however, telomerase assays can also be carried out using amplification methods other than PCR, although described in terms below of PCR. In the first step of a TRAP-eze™ reaction, telomerase adds a number of telomeric repeats (GGTTAG) on the 3' end of a substrate oligonucleotide (TS, telomerase substrate) (FIG. 31).

A specific sequence, e.g., AGAGTT or TTAGGG, at the 3' end of an oligomer is critical in order for the oligomer to serve as a TS (see Morin, 1991, Nature 353:454–456). Preferably, the sequence is 5–6 nucleotides long, although shorter sequences, e.g., 4 nucleotides, may also be employed.

In the second step, the extended products are amplified by PCR using the TS and a reverse primer (RP) which comprises a sequence complementary to the telomeric repeats' sequence of the TS-telomerase extension product, generating a ladder of products with 6 base increments starting at 50 nucleotides: 50, 56, 62, 68, etc. Thus PCR amplification of these ladder bands takes place only when telomerase is present in the samples, since the reaction products of active telomerase serve as templates for the PCR amplification. The level of telomerase activity is assessed by measuring the amount of PCR products.

In a preferred aspect, the RP is a hairpin primer of the invention. In one specific embodiment, a 17 bp-long nucleotide, labelled with a MET pair, 5'-ACGCAATGTATGCGT*GG-3' (SEQ ID NO:29), is added to the 5' end of a linear RP primer, forming a hairpin primer of the invention for use as an RP (See Example 15, FIG. 30A). By way of example, a donor moiety can be attached to the 5' end of the oligomer, and an acceptor moiety attached to the T residue.

Figure 30A:
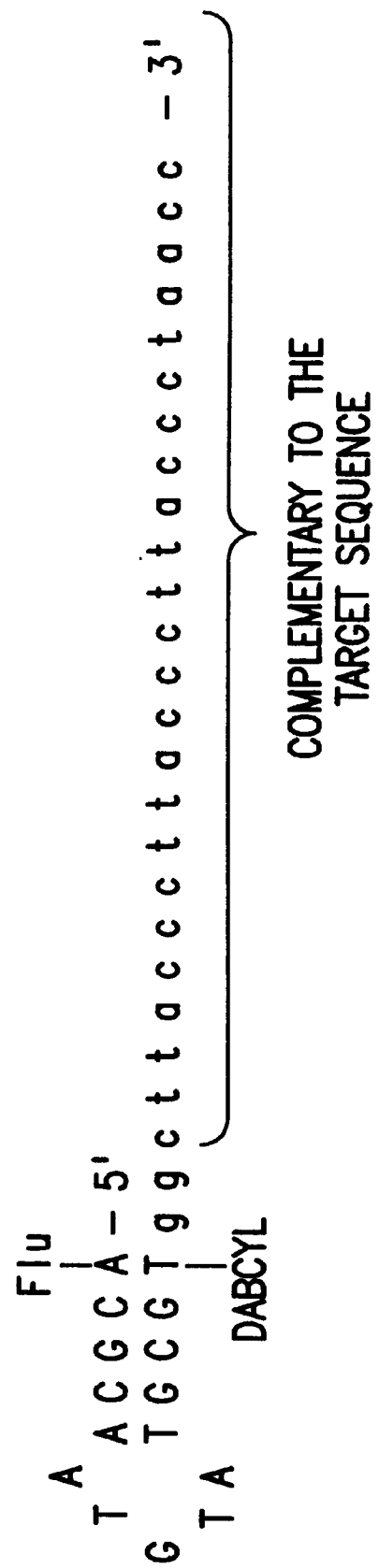
Figure 30B:
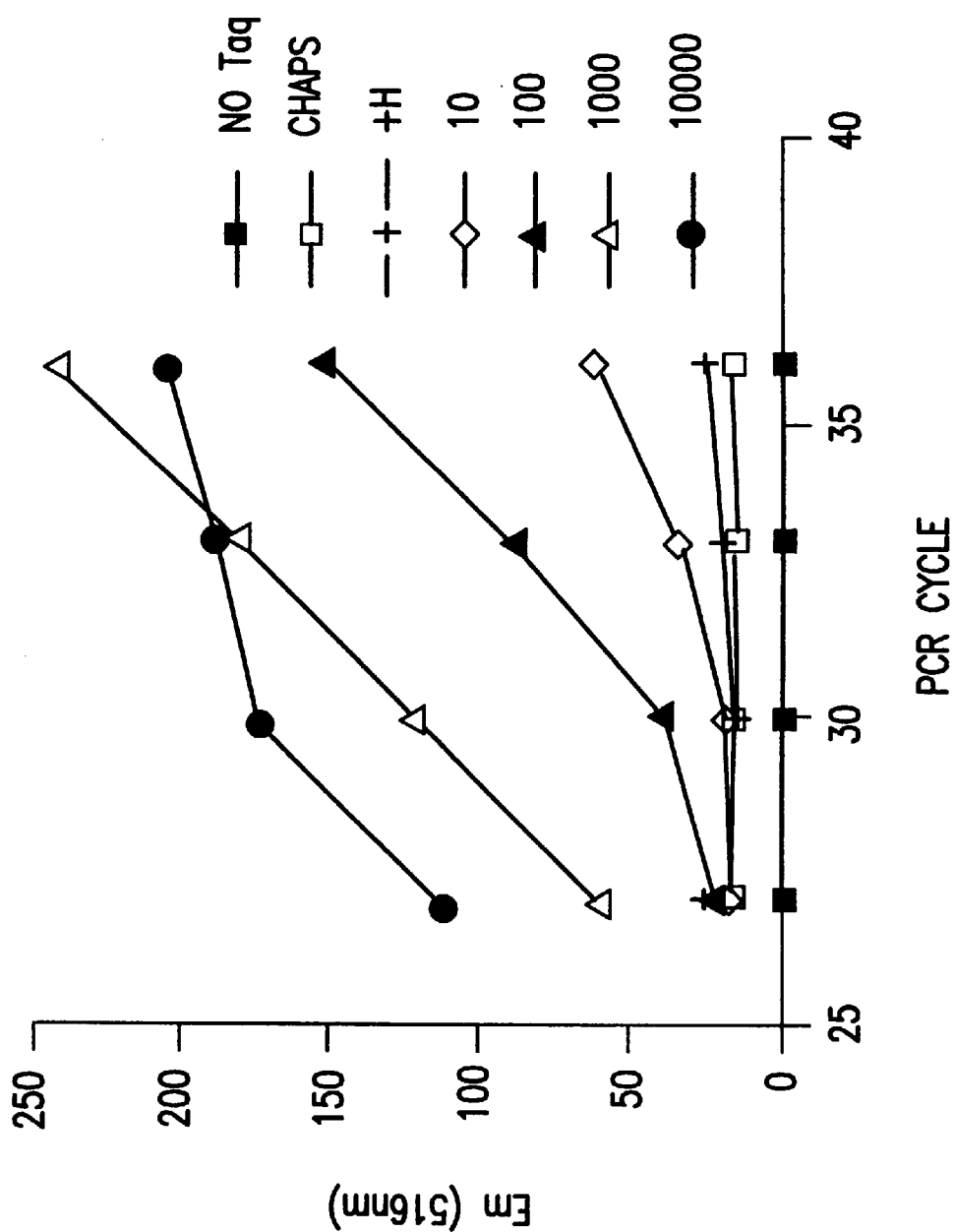

By optimizing the reaction conditions, a very low level of telomerase activity can be detected; the sensitivity of the assay is comparable to those of conventional assays that utilize polyacrylamide gel electrophoresis of PR products (FIG. 30B).

In another embodiment, the stem-loop hairpin structure may be attached to the 5' end of the TS primer. The modified TS oligomer therefore serves not only as a primer for PCR amplification but also as a substrate for the telomerase. It does so because the substrate specificity of the telomerase appears to be determined by the nucleotide sequences at the 3' end of the TS oligomer.

In yet another embodiment, telomerase-positive cells can be detected in tissue sections by using TRAP in situ in tissue sections, and by using a hairpin primer of the invention, e.g., the primer shown in FIG. 30A, as a primer for the TRAP. The method described herein can be used for the detection of single cells with telomerase activity. Such a sensitive level of detection is difficult to obtain by conventional in-tube TRAP assays of tissue samples.

While the PCR-based TRAP assay is sensitive enough to detect small amounts of telomerase activity in cell/tissue extract (i.e., telomerase activity present in 1% of the cell population will be detected) it is impossible to identify individual telomerase-positive cells in the heterogeneous population, and to correlate cell/tissue morphology with telomerase expression. In contrast, identification of telomerase-positive cells using conventional fluorescence microscopy in an in situ TRAP assay permits the study of both the telomerase expression and the pathophysiological condition of a single cell.

Like an in-tube TRAP assay, an in situ TRAP assay (see Section 15.1, Experiment 2) requires enzymatically active telomerase. The in situ TRAP assay detects telomerase activity by means of amplifying the telomerase-extended products, which serve as the DNA templates for the amplification reaction, preferably PCR.

To detect PCR products in a standard in-tube TRAP assay, several procedures are possible. For example, in one embodiment, labeled probe for a gene target of interest can be hybridized to the PCR products, followed by antibody detection of the bound probe. Alternatively, incorporation of a label into the PCR product may be detected by an antibody.

In contrast, utilization of the hairpin primers of the invention for in situ TRAP assay eliminates the detection step described above. As in an in-tube TRAP assay, an in situ TRAP assay can use a hairpin primer for either the TS or RP primer. Since only hairpin primers that are incorporated into the resulting PCR products fluoresce, after amplification, the slides can be viewed directly under a fluorescence microscope without detection/washing steps after PCR amplification. Cells will only fluoresce if the gene target of interest is amplified.

The utilization of hairpin primers in in situ TRAP assays has great advantages over other methods. First, it eliminates the detection step. One of the technical problems of in situ PCR methodology is the diffusion of the PCR products, making the identification of the native site of the amplified products extremely difficult. Elimination of the detection step minimizes this problem. Further, elimination of both the detection and washing steps allows the morphology of the tissues to be maintained.

Second, an internal control can be incorporated. Heterogeneity of the slide preparations and possible presence of PCR amplification inhibitors may lead to false-negative results. Incorporation of an internal positive control for PCR amplification will obviate the problem. The internal control consists of a pair of primers and a DNA template, and is added into the TRAP reaction mixture. One of the two primers of the internal control is a MET pair-labeled hairpin primer of the invention, e.g., a rhodamine/DABCYL labeled hairpin primer that performs FRET. Utilization of this second fluorescent label (e.g., rhodamine) with an emission profile that is distinct from the fluorescent label on the non-control hairpin primer allows simultaneous identification of two different amplification products: e.g., the telomerase product labeled with FAM and the internal control labeled with rhodamine. By viewing the sample in a fluorescence microscope through separate filters appropriate for FAM and for rhodamine, respectively, one can assess whether amplification of the control has occurred.

The amplification of the internal control is independent of the presence or absence of telomerase activity in the specimen. The presence of PCR inhibition can be assessed by the failure or marked decrease of the amplification of the internal control on the sample slides. Therefore, when a sample shows no telomerase products but does show amplification of the internal control, the result can be interpreted as indicating that the sample is truly telomerase-negative, and that it is not a false-negative result caused by PCR inhibition. Thus, the reliability of the methodology is greatly enhanced.

Finally, one of the biggest obstacles in setting up TRAP assays in a clinical laboratory setting is that the assay is extremely prone to PCR carry-over contamination. The closed-tube format of the TRAP assay described above, which uses the hairpin primers of the invention rather than conventional PCR primers, will have great utility in clinical laboratories.

5.2.6. METHODS OF USE OF HAIRPIN PRIMERS IN CASCADE ROLLING CIRCLE AMPLIFICATION (CRCA)

Hairpin primers of the invention may be used in Cascade Rolling Circle Amplification (CRCA) (Lizardi and Caplan, PCT International Publication No. WO 97/19193, published May 29, 1997) (FIG. 31). As in PCR, CRCA is driven by two primers. In an embodiment of the invention using CRCA, one or both of the primers is a hairpin primer labeled with a MET pair, and preferably, only one hairpin primer is labeled with a MET pair. The hairpin primer will only generate a MET signal when it is incorporated into the cascade reaction products. However, unlike PCR, the reaction does not require repeated cycles of heat denaturation, and thus is isothermal. In this process, a first, forward primer hybridizes to a circularized probe template, and is extended by a DNA polymerase, e.g., Bst DNA polymerase Large Fragment ("Bst LF polymerase"), around the circle and eventually displaces the primer end to form a long 5' tail. A second, reverse primer initiates strand displacement synthesis on the tail that is displaced from the first-primer synthesis.

A CRCA results, wherein both primers are continually cycled to initiate synthesis on the displaced strand from the previous round of synthesis. The use of a hairpin primer of the invention, either as the forward or the reverse primer, makes possible direct detection of CRCA products in a closed system. When it is coupled with an initial, highly discriminatory ligation reaction (see below) to circularize a divalent linear probe at a target site, a CRCA reaction using the hairpin primers of the invention can serve as an extremely sensitive and simple system for detection of infectious agents, allotyping, and rare event detection such as in cancer diagnostics.

In order for CRCA to begin, ligation of a linear probe (preferably approximately 90 bases in length) to a target sequence must take place. This is catalyzed by a thermophilic ligase, e.g., Ampligase (Epicentre Technologies, Madison, Wis.). The forward primer is added and anneals to the circularized probe. CRCA is initiated upon addition of a polymerase with strong strand-displacement activity, preferably Bst DNA polymerase, Large Fragment (8 units). This thermophilic enzyme generates a tailed product several kilobases in length and produces many tandem repeats of the target sequence, and hence, many binding sites for the reverse primer.

Both the forward and reverse primers, one or both of which can be a hairpin primer labeled with a MET pair, but preferably only one labeled with a MET pair, are preferably present in excess (1 µM) to ensure rapid binding to template DNA. As each primer is extended, the polymerase displaces the growing strand ahead of it, creating a new set of single-stranded tails with binding sites for the other primer (FIG. 31).

This process continues through many cycles and can generate, from a few hundred copies of the original circle, several micrograms of double-stranded amplification product containing incorporated hairpin primers. Upon lowering the temperature for measurement of a MET emission, any unincorporated hairpin primers will return to a hairpin configuration. When the MET pair is a donor-quencher FRET pair, this return to hairpin configuration will quench the fluorescent signal. Thus, when used with hairpin primers labeled with donor-quencher FRET pairs, no signal above background should be obtained in samples in which no ligation or cascade reaction occurred.

Figure 32B:
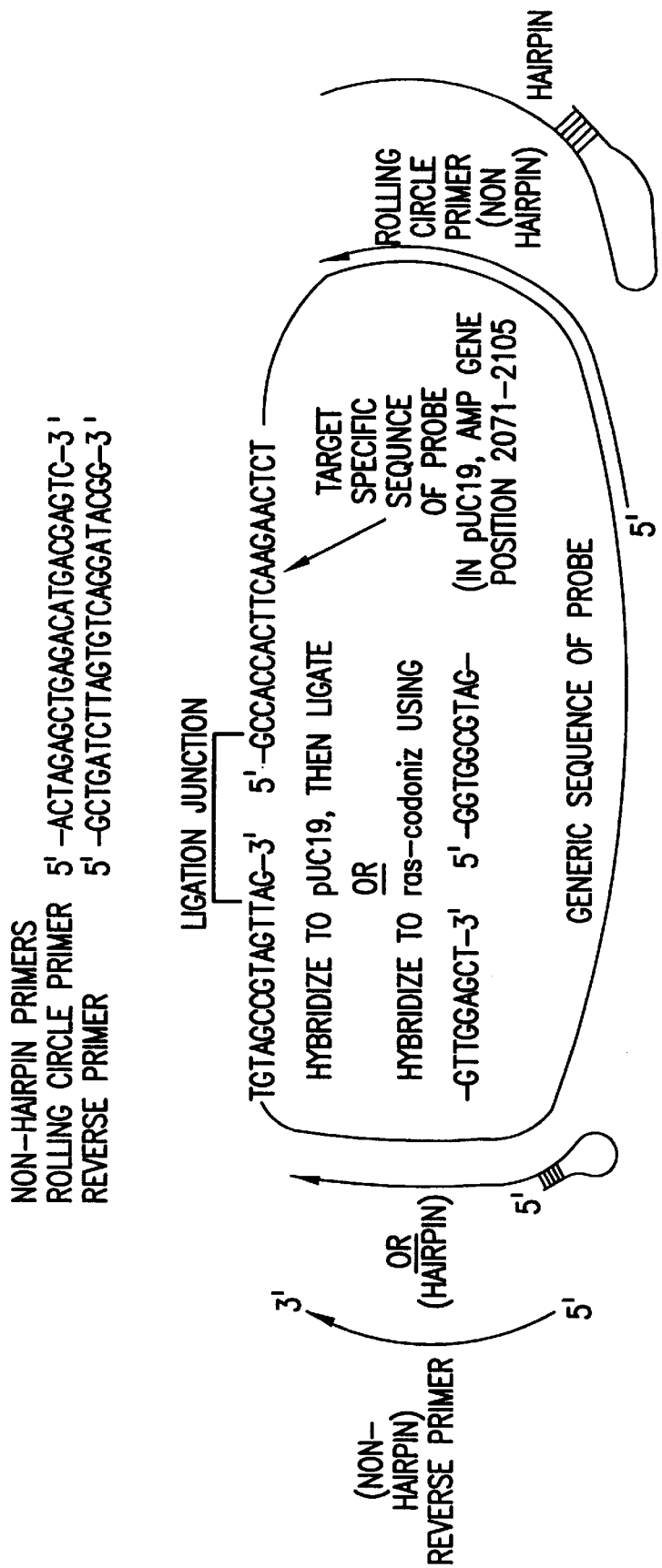

Since CRCA takes place at one temperature, generally around 60–65° C., the primers need to be long enough (18 mers or longer) to bind effectively at these temperatures. Hairpin primers are preferably chosen that can form a strong hairpin at ambient temperatures yet be relatively unstable at 60–65° C. such that the hairpin does not inhibit strand displacement synthesis (FIG. 32). The hairpin can partially overlap the primer binding sequences, which will further destabilize the hairpin during synthesis, or may be separated by a spacer region from the primer binding site.

In a preferred embodiment of a CRCA using the hairpin primers of the invention, other reaction components include 200 µM dNTPs, 2 mM MgSO$_4$, 20 mM Tris-HCl, pH 8.8, 10 mM KCl, 10 mM (NH$_4$)$_2$SO$_4$, and 0.1% Triton X-100. The ligation and cascade reactions can take place in the same tube and at the same temperature, with the ligase being added first in the presence of NAD+ (0.5 mM) and incubated for 10 minutes before addition of the polymerase.

5.3. METHODS OF DETECTION OF AMPLIFICATION PRODUCTS USING 3'-5' EXONUCLEASE AND/OR ELEVATED TEMPERATURE

The methods of the invention described in the subsections below may be also combined with those methods described in Section 5.4 (employing linear primers) for use during nucleic acid amplification reactions including PCR, triamplification, NASBA and SDA. Since the use of 3'-5' exonuclease or elevated temperature allows detection of amplified product without the need for separation of unincorporated primers (thus allowing a "closed tube" format), such procedures are preferred for use with linear primers. Since the use of hairpin primers allows one to distinguish between amplified produce and unincorporated primers based on type of signal detected, exonuclease treatment or heat is not necessary for use in procedures employing the hairpin primers of the invention.

5.3.1. USE OF 3'-5' EXONUCLEASE IN AMPLIFICATION REACTIONS

As described in certain of the embodiments in Section 5.4 relating to PCR and triamplification, and also for use with NASBA and SDA, after an amplification reaction is complete, 3'-5' exonuclease can be introduced into the reaction vessel to cleave all free primer. Then, the donor label is stimulated with light of the appropriate wavelength. When the acceptor moiety is a fluorophore, the only acceptor label that will emit is that which remains on uncleaved primer that has been incorporated into the amplified product, thus giving an indication of the extent of amplification. The further amplification has proceeded, the greater the signal will be. When the acceptor moiety does not fluoresce and dissipates transfer energy as heat (i.e., quenches), the progress of the amplification reaction may be measured as a decrease in the emissions of the donor.

Figure 8A:
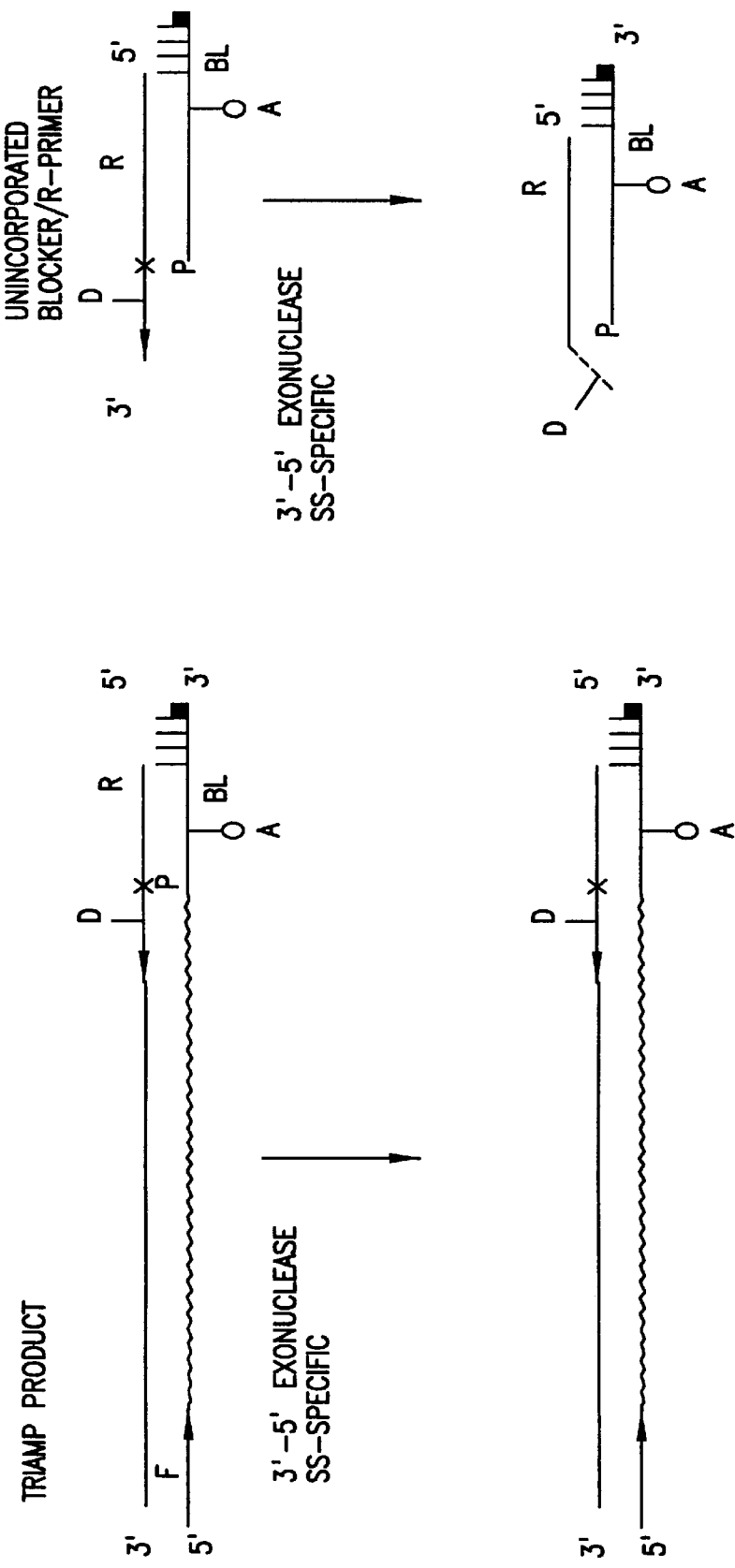

In one embodiment, wherein triamplification is employed (Section 5.4.2), single-strand-specific 3'-5' exonuclease is added to the amplification vessel after the amplification is complete. As shown in FIG. 8, 3'-5' exonuclease treatment hydrolyzes the non-base-paired end of the reverse primer. The 3'-end of the blocker is protected and remains intact.

The interaction of the FRET fluorophores inside the amplified product will not be affected by this treatment for two reasons. First, the 3'-end of the amplified product will be base-paired and thus will not be a good substrate for the exonuclease. Second, the primer that is incorporated into the amplification product is extended on its 3' end and its labeled nucleotide residue will be relatively far from the unprotected 3'-hydroxyl. Therefore, it will take much longer for the nuclease to reach the modified residue. As a result, the only detectable FRET signal will come from the amplified product and will be free of background. Preferably the donor should be on the forward primer, and the acceptor on the blocker, but the converse is also possible.

Figure 11B:
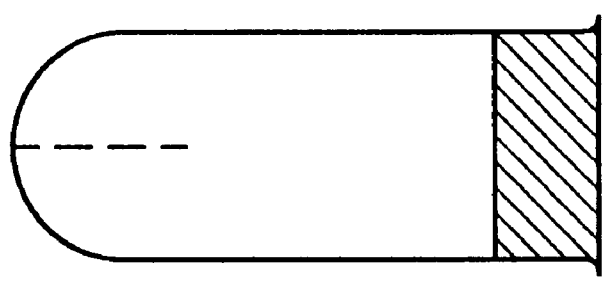
Figure 11A:
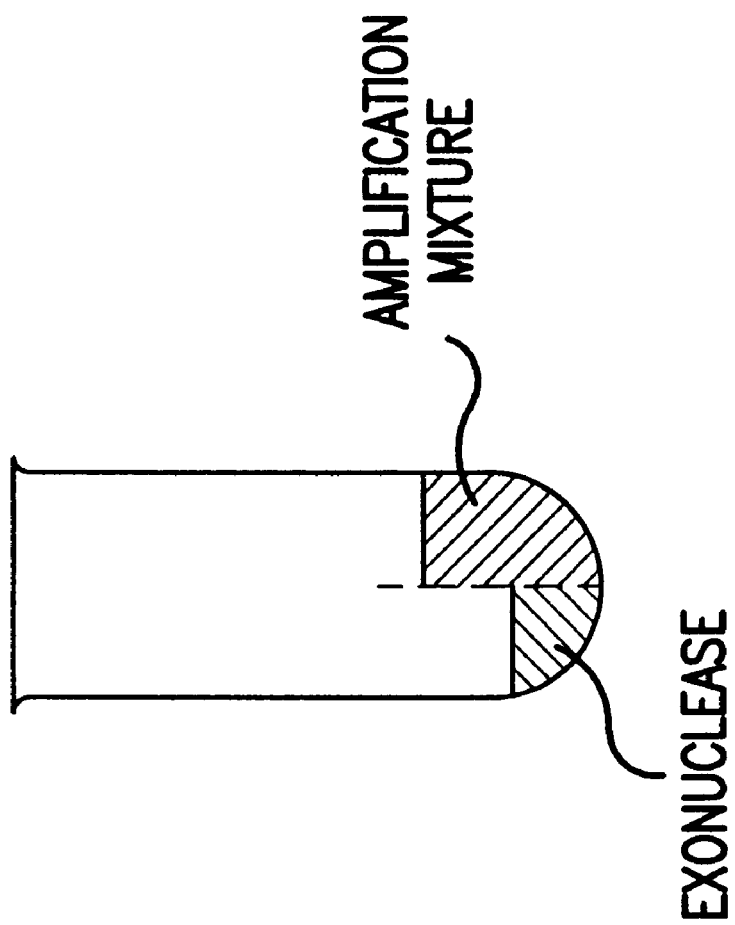

The use of 3'-5' exonuclease in nucleic acid amplifications using linear primers eliminates the necessity of separating the amplification product from the non-incorporated oligonucleotides after the reaction. In a preferred embodiment, the method of the present invention may be carried out in the vessel in which the amplification reaction proceeds, without opening the vessel in order to allow for separation of amplification product. Polymerase and exonuclease may be mechanically separated during amplification, for example, in a two-chamber reaction tube as shown in FIG. 11A. After amplification, the reaction tube is inverted, as in FIG. 11B, allowing exonuclease to mix with the amplification mixture, resulting in hydrolysis of unreacted labeled primer. This provides for a greatly decreased chance of carryover contamination, and consequently, fewer false positive results in clinical studies. This "closed-tube" format is also readily amenable to automation.

In another embodiment, triamplification or PCR amplification can be performed as described in Sections 5.4.1, 5.4.2 and 6, with the exception that thermostable DNA polymerase is present as a combination of two enzymes, with and without 3'-5' exonuclease activity. The ratio of polymerase to exonuclease can be adjusted such that polymerization predominates during the amplification cycles. After amplification, when the cycling is over, single-stranded template will no longer be generated to which primers can bind. Hence there will be no template/primer complex for DNA polymerase to bind for dNTP incorporation. Therefore, the DNA polymerase will have a chance to bind and digest the unreacted primers using its 3'-5' exonuclease activity.

5.3.2. USE OF TEMPERATURE ELEVATION IN AMPLIFICATION REACTIONS

Background fluorescence of an amplification reaction such as a triamplification reaction can be decreased greatly by increasing the temperature of the amplification vessel, as an alternative to using exonuclease. During detection, the temperature in the vessel is raised sufficiently high enough to cause the short duplex formed between the unused blocker and the reverse primer to dissociate, preventing FRET. At the same time, the much longer amplification product remains double-stranded and generates a FRET signal (see, e.g., Example 5). In this embodiment, detection will preferably be carried out using a thermostable-cuvette or plate-reader fluorimeter. This embodiment also has the advantage that separation of the amplification product from unused primer is not required. Thus, as in the previous embodiment that uses exonuclease treatment, amplification products may be detected directly, without opening the reaction vessel.

5.4. METHODS FOR DETECTION OF AMPLIFICATION PRODUCTS USING LINEAR PRIMERS

Linear primers of the invention can be employed, for example, in PCR, NASBA, strand displacement, and triamplification in vitro or in situ. When using linear primers in closed-tube format amplification reactions, 3'-5' exonuclease treatment and/or temperature elevation (Section 5.3) is preferably used to distinguish the primers from the amplification product.

5.4.1. METHODS OF USE OF LINEAR PRIMERS IN POLYMERASE CHAIN REACTION (PCR)

Figure 25:
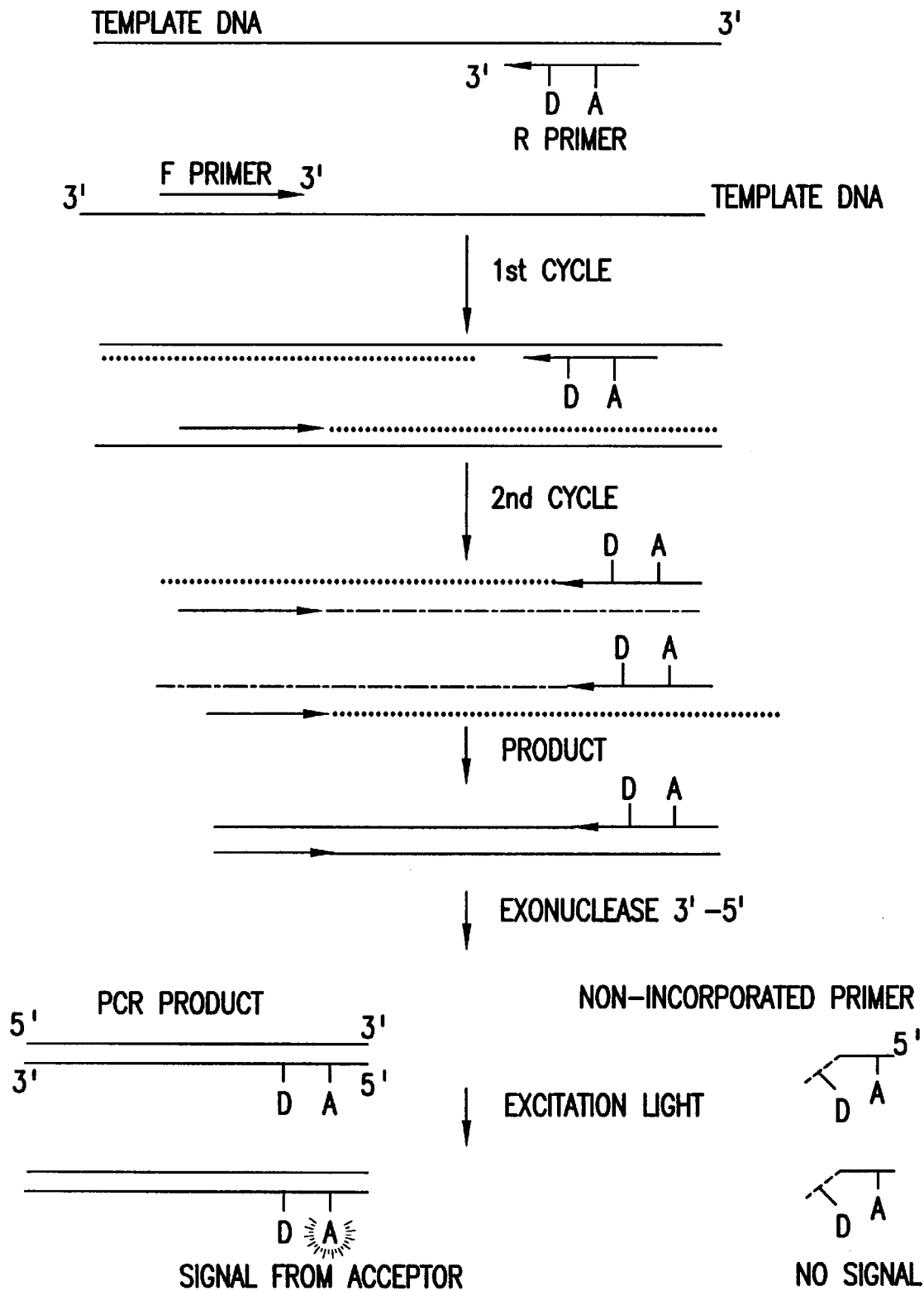

In one embodiment, the primers of the invention are used to prime a polymerase chain reaction (PCR) (an example of which is shown in FIG. 25), thereby becoming incorporated into the amplification product. A donor fluorophore moiety is attached to the primer, and an acceptor moiety that is either a fluorophore or a quencher is attached a short distance away from the donor (30 nucleotides or less) on the same primer.

After the PCR amplification is complete, 3'-5' exonuclease is introduced into the reaction vessel. The exonuclease cleaves all free primer in the reaction vessel. The reaction mixture is then exposed to light of the appropriate wavelength to excite the donor moiety.

When the acceptor moiety is a fluorophore, the only acceptor label that will emit light is that which remains on uncleaved primer that has been incorporated into the amplified product, thus giving an indication of the extent of amplification. The further amplification has proceeded, the greater the signal from the acceptor moiety will be. When the acceptor moiety does not fluoresce and dissipates transfer energy as heat (i.e., it quenches), the progress of the reaction may be measured as a decrease in the emissions of the donor.

5.4.1.1. METHODS OF USE OF LINEAR PRIMERS IN ALLELE-SPECIFIC PCR (ASP)

In another embodiment, linear primers of the invention are used to prime an allele-specific PCR (ASP) as is described in Section 5.2.1.1 supra. In this embodiment, one or both amplification primers can be linear primers.

5.4.2. METHODS OF USE OF LINEAR OLIGONUCLEOTIDES IN TRIAMPLIFICATION

In one embodiment, a pair of linear primers of the invention is used in triamplification (the general steps for which are described in Section 5.2.2.1).

As applied to the gap version of triamplification, and in an embodiment wherein the donor and acceptor moieties, respectively, of a MET pair are situated on separate linear oligonucleotides, either the forward or the reverse extending primer, and the third or blocking oligonucleotide are labeled. However, one of the pair of MET donor-acceptor labels should be on the blocker, and the other should be on a single-stranded 3' end of the primer that is complementary to the blocker (see, e.g., FIGS. 7 and 8). In such a specific embodiment employing a FRET pair consisting of donor and acceptor fluorophores, the primer and blocking oligonucleotide are labeled with the donor and acceptor fluorophores, respectively, such that when both oligonucleotides are in close proximity (hybridized to each other) and the donor label is stimulated, FRET occurs and a fluorescence signal is produced at the emission wavelength of the acceptor fluorophore. (Alternatively, the acceptor moiety may be a quencher.) In a specific embodiment, the primer that is not complementary to the blocker is unlabeled with either the donor or acceptor moieties of the FRET pair, or alternatively, is labeled with both moieties (see paragraph below). After triamplification, exonuclease treatment and/or temperature elevation are preferably used to allow detection of amplified product without the need for separation of unincorporated primers (see Sections 5.3.1 and 5.3.2).

In another embodiment using triamplification wherein it is desired to use linear oligonucleotide(s) doubly labeled with both acceptor and donor moieties of a MET pair, and wherein exonuclease treatment (but not temperature elevation) is to be used after the triamplification reaction so as to avoid the need for separation of unincorporated labeled oligonucleotides, the forward and/or the reverse primer can each be labeled with both the donor and acceptor moieties of the FRET pair (within FRET distance of each other) if one of the moieties is on a 3' single stranded extension.

5.5. METHODS OF USE OF HAIRPIN OR LINEAR PRIMERS IN MULTIPLEX ASSAYS

Through the use of several specific sets of primers, amplification of several nucleic acid targets can be performed in the same reaction mixture. In a preferred embodiment, one or both primers for each target can be hairpin primers labeled with a fluorescent moiety and a quenching moiety that can perform FRET. Amplification of several nucleic acid targets requires that a different fluorescent acceptor moiety, with a different emission wavelength, be used to label each set of primers.

During detection and analysis after an amplification, the reaction mixture is illuminated and read at each of the specific wavelengths characteristic for each of the sets of primers used in the reaction. It can thus be determined which specific target DNAs in the mixture were amplified and labeled. In a specific embodiment, two or more primer pairs for amplification of different respective target sequences are used.

5.6. ASSAYING THE METHYLATION STATUS OF DNA USING AMPLIFICATION REACTIONS OF THE INVENTION

Methylation of cytosine located 5' to guanosine is known to have profound effects on the expression of several eukaryotic genes (Bird, 1992, Cell 70: 5–8). In normal cells, methylation occurs predominantly in CG-poor regions, while CG-rich areas, called "CpG-islands," remain unmethylated. The exception is extensive methylation of CpG islands associated with transcriptional inactivation of regulatory regions of imprinted genes (Li et al., 1993, Nature 366: 362–365) and with entire genes on the inactive X-chromosome of females (Pfeifer et al., 1989, Science 246: 810–813).

Aberrant methylation of normally unmethylated CpG islands has been documented as a relatively frequent event in immortalized and transformed cells (Antequera et al., 1990, Cell 62: 503–514], and has been associated with transcriptional inactivation of defined tumor suppressor genes in human cancers (Herman et al., 1996, Proc. Natl. Acad. Sci., USA 93: 9821–9826). Sensitive detection of CpG island methylation has the potential to define tumor suppressor gene function and provides a new strategy for early tumor detection.

Methylation specific PCR is a sensitive detection method for abnormal gene methylation in small DNA samples (Herman et al., 1996, Proc. Natl. Acad. Sci., USA 93: 9821–9826). Methylation specific PCR employs an initial bisulfite reaction to modify DNA. All unmethylated cytosines are dominated in a bisulfite reaction and converted to uracils. Methylated cytosines are unaffected by the bisulfite reaction. Consequently, a sequence of DNA that is methylated will differ in sequence, after bisulfite treatment, from an identical sequence that is unmethylated. Hence, different sets of primers may be designed to specifically amplify each of those sequences (e.g., a pair of primers to amplify unmethylated, bisulfite treated DNA will have one or more G residues replaced by an A residue (to be complementary to nucleotides that were formerly unmethylated cytosines), and one or more C residues replaced by a T residue, respectively, for the two primers of the pair, relative to the primer pair for the methylated or untreated DNA).

As in any other PCR-based technique, this method is very sensitive. Any carry-over contamination from sources external to the PCR will cause false positive results. The use of the MET-labeled hairpin primers of the present invention eliminates the risk of carry-over contamination, since the reaction may be performed and monitored (in real time, if necessary) in a closed-tube format.

The use of bisulfite treatment in the methods of the invention is not limited to those methods employing PCR; other amplification methods may alternatively be employed. The invention thus provides a method of assaying the methylation status of DNA using an amplification reaction of the invention, with hairpin or linear primers. The method comprises: prior to conducting an amplification reaction, contacting a sample containing purified nucleic acids with an amount of bisulfite sufficient to convert unmethylated cytosines in the sample to uracil; and conducting the amplification reaction in the presence of a primer pair specific for preselected target sequences, e.g., Fragile X gene, Prader-Willi syndrome region, Angelman syndrome region, p15 gene, p16 gene, E-cadherin gene, von Hippel-Lindau syndrome gene. Pairs of primers, used in separate reaction vessels, are preferably specific for bisulfite-treated methylated, bisulfite-treated unmethylated, and nonbisulfite-treated (wild type) nucleic acids, respectively. Conclusions about the methylation status of the nucleic acids in the sample can be drawn depending on which primer pair(s) give amplification product. In a preferred embodiment, the amplification reaction is PCR using one or more hairpin primers.

Kits as well as methods for determining the methylation status of DNA are also provided. In specific embodiments, such kits comprise in one or more containers one or more oligonucleotides of the invention for conducting the amplifications, and sodium bisulfite (optionally in combination with hydroquinone powder). Optionally, such kits further comprise in separate containers one or more of the following: mineral oil, DNA binding matrix, NaI solution, glycogen, amplification buffer, unmethylated control DNA, and methylated control DNA.

5.7. KITS FOR THE AMPLIFICATION AND DETECTION OF SELECTED TARGET DNA SEQUENCES

An additional aspect of the present invention relates to kits for the detection or measurement of nucleic acid amplification products. In specific embodiments, the kits comprise one or more primer oligonucleotides of the invention, such as a hairpin primer, including but not limited to a universal hairpin primer, and/or linear primers, in one or more containers. The kit can further comprise additional components for carrying out the amplification reactions of the invention. Where the target nucleic acid sequence being amplified is one implicated in disease or disorder, the kits can be used for diagnosis or prognosis. In a specific embodiment, a kit is provided that comprises, in one or more containers, forward and reverse primers of the invention for carrying out amplification, and optionally, a DNA polymerase or two DNA polymerases respectively with and without exonuclease activity. A kit for triamplification can further comprise, in one or more containers, a blocking oligonucleotide, and optionally DNA ligase.

Oligonucleotides in containers can be in any form, e.g., lyophilized, or in solution (e.g., a distilled water or buffered solution), etc. Oligonucleotides ready for use in the same amplification reaction can be combined in a single container or can be in separate containers. Multiplex kits are also provided, containing more than one pair of amplification (forward and reverse) primers, wherein the signal being detected from each amplified product is of a different wavelength, e.g., wherein the donor moiety of each primer pair fluoresces at a different wavelength. Such multiplex kits contain at least two such pairs of primers.

In a specific embodiment, a kit comprises, in one or more containers, a pair of primers preferably in the range of 10–100 or 10–80 nucleotides, and more preferably, in the range of 20–40 nucleotides, that are capable of priming amplification [e.g., by polymerase chain reaction (see e.g., Innis et al., 1990, PCR Protocols, Academic Press, Inc., San Diego, Calif.), for example, competitive PCR and competitive reverse-transcriptase PCR (Clementi et al., 1994, Genet. Anal. Tech. Appl. 11(1):1–6; Siebert et al., 1992, Nature 359:557–558); triamplification, NASBA, strand displacement, or other methods known in the art, under appropriate reaction conditions, of at least a portion of a selected target nucleic acid.

In another embodiment, a kit for the detection of a selected target DNA target sequence comprises in one or more containers (a) PCR primers, one or both of which are hairpin primers labeled with fluorescent and quenching moieties that can perform MET; and optionally: (b) a control DNA target sequence; (c) an optimized buffer for amplification; (d) appropriate enzymes for the method of amplification contemplated, e.g., a DNA polymerase for PCR or triamplification or SDA, a reverse transcriptase for NASBA; (d) a set of directions for carrying out amplification, e.g., describing the optimal conditions, e.g., temperature, number of cycles for amplification. Optionally, the kit provides (e) means for stimulating and detecting fluorescent light emissions, e.g., a fluorescence plate reader or a combination thermocycler-plate-reader to perform the analysis.

In yet another embodiment, a kit for triamplification is provided. The kit comprises forward and reverse extending primers, and a blocking oligonucleotide. Either the forward or reverse primer is labeled with one moiety of a pair of MET moieties, and the blocking oligonucleotide is labeled with the other MET moiety of the pair. One embodiment of such a kit comprises, in one or more containers: (a) a first oligonucleotide; (b) a second oligonucleotide, wherein said first and second oligonucleotides are linear primers for use in a triamplification reaction; (c) a third oligonucleotide that is a blocking oligonucleotide that comprises a sequence complementary and hybridizable to a sequence of said first oligonucleotide, said first and third oligonucleotides being labeled with a first and second moiety, respectively, that are members of a molecular energy transfer pair consisting of a donor moiety and an acceptor moiety, such that when said first and third oligonucleotides are hybridized to each other and the donor moiety is excited and emits energy, the acceptor moiety absorbs energy emitted by the donor moiety; and (d) in a separate container, a nucleic acid ligase.

Another embodiment of a kit comprises in a container a universal hairpin optionally also comprising a second container containing cyanogen bromide or a nucleic acid ligase (e.g., DNA ligase, for example, T4 DNA ligase).

Figure 5:
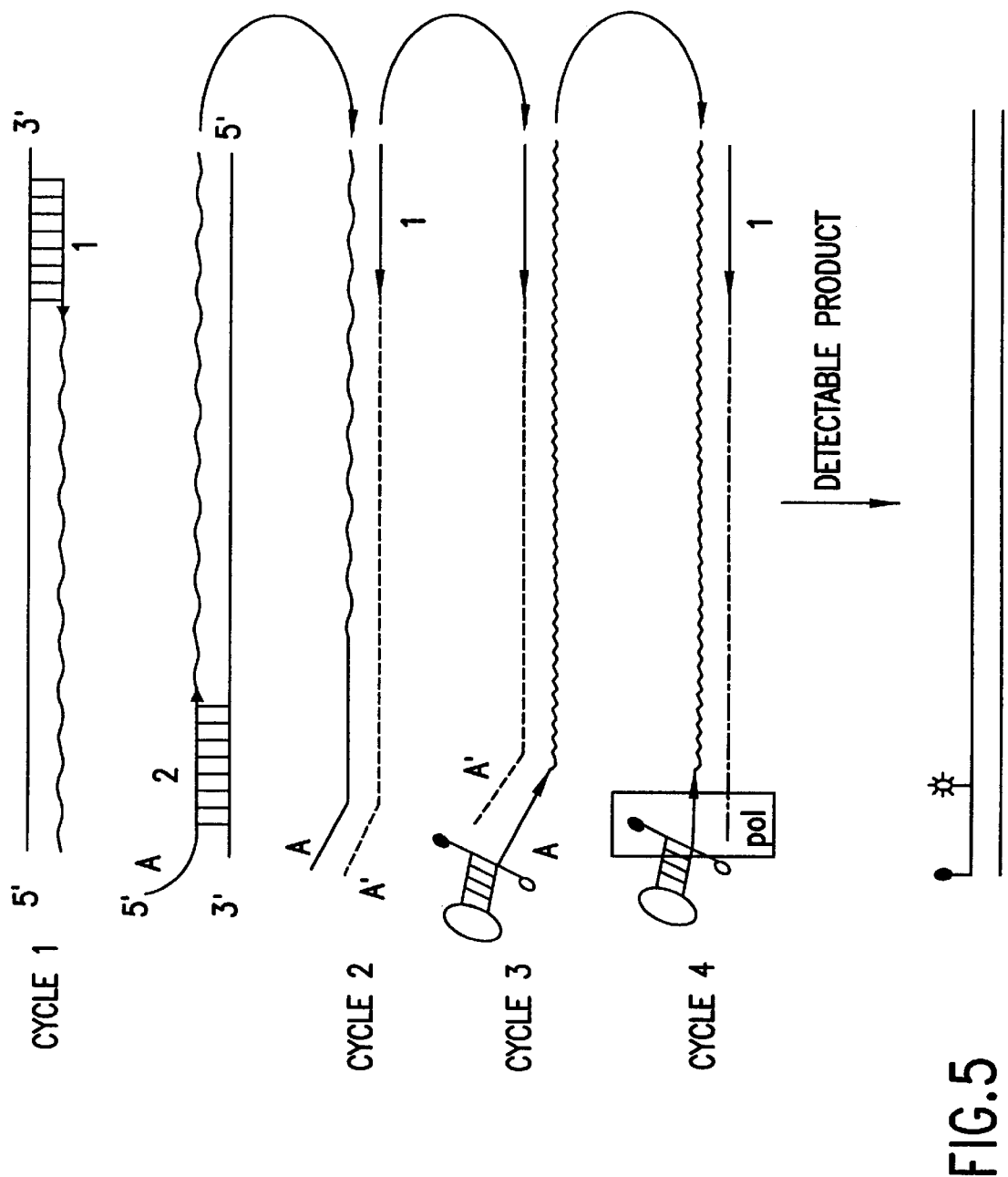

A kit for carrying out a reaction such as that shown in FIG. 5 comprises in one or more containers: (a) a first oligonucleotide primer; (b) a second oligonucleotide primer, wherein the first and second oligonucleotide primers are forward and reverse primers for DNA synthesis in an amplification reaction to amplify a nucleic acid sequence, and wherein said second oligonucleotide primer comprises (i) a 5' sequence that is not complementary to a preselected target sequence in said nucleic acid sequence, and (ii) a 3' sequence that is complementary to said preselected target sequence; and (c) a third oligonucleotide primer that comprises in 5' to 3' order (i) a first nucleotide sequence of 6–30 nucleotides, wherein a nucleotide within said first nucleotide sequence is labeled with a first moiety selected from the group consisting of a donor moiety and an acceptor moiety of a molecular energy transfer pair, wherein the donor moiety emits energy of one or more particular wavelengths when excited, and the acceptor moiety absorbs energy at one or more particular wavelengths emitted by the donor moiety; (ii) a second, single-stranded nucleotide sequence of 3–20 nucleotides; (iii) a third nucleotide sequence of 6–30 nucleotides, wherein a nucleotide within said third nucleotide sequence is labeled with a second moiety selected from the group consisting of said donor moiety and said acceptor moiety, and said second moiety is the member of said group not labeling said first nucleotide sequence, wherein said third nucleotide sequence is sufficiently complementary in reverse order to said first nucleotide sequence for a duplex to form between said first nucleotide sequence and said third nucleotide sequence such that said first moiety and second moiety are in sufficient proximity such that, when the donor moiety is excited and emits energy, the acceptor moiety absorbs energy emitted by the donor moiety; (iv) at the 3' end of said third oligonucleotide primer, a fourth nucleotide sequence of 10–25 nucleotides that comprises at its 3' end a sequence identical to said 5' sequence of said second oligo- nucleotide primer. Where such kit is used for triamplification, a blocking oligonucleotide can also provided.

Another kit of the invention comprises in one or more containers: (a) a first oligonucleotide; (b) a second oligonucleotide, said first and second oligonucleotide being hybridizable to each other; said first oligonucleotide being labeled with a donor moiety said second oligonucleotide being labeled with an acceptor moiety, said donor and acceptor moieties being a molecular energy transfer pair, wherein the donor moiety emits energy of one or more particular wavelengths when excited, and the acceptor moiety absorbs energy at one or more particular wavelengths emitted by the donor moiety; and (c) in a separate container, a nucleic acid ligase.

6. EXAMPLES

GENERAL EXPERIMENTAL METHODS

The following experimental methods were used for all of the experiments detailed below in the Examples, Sections 7–13, except as otherwise noted. In all of the Examples, the experiments were carried out using either triamplification or PCR.

6.1. OLIGONUCLEOTIDE SEQUENCES: SYNTHESIS AND MODIFICATION

Three oligodeoxynucleotides complementary to segments of human prostate specific antigen (PSA) DNA were synthesized (FIG. 12). Reverse primer contained a 2'-O-methyl moiety at a position complementary to the 5'-end of the blocker. This modification was essential for prevention of strand displacement during the amplification process (see Section 5.2.2.1) The blocker had biotin on its 3' end, in order to protect it from 3'-5' exonuclease hydrolysis and from undesirable extension during amplification. During the synthesis of blocker and forward primer, the primary amino group was incorporated on the modified T-base (Amino-Modifier C6 dT) as described by Ju et al. (1995, Proc. Natl. Acad. Sci. USA 92:4347–4351). These modifications were used for subsequent incorporation of fluorescent dyes into designated positions of the oligonucleotides. Synthesized oligonucleotides were desalted and FAM (as a donor) and rhodamine (as an acceptor) were attached to a modified thymidine residue of the reverse primer and blocker, respectively, by the method published by Ju et al. (1995, Proc. Natl. Acad. Sci. USA 92:4347–4351). Labeled oligo- nucleotides were purified on a 15% denaturing polyacryla- mide gel.

The absorption spectra of the primers were measured on a Hewlett Packard 8452A diode array spectrophotometer and fluorescence emission spectra were taken on a Shimadzu RF-5000 spectrofluorophotometer (Columbia, Md.).

6.2. AMPLIFICATION OF PROSTATE SPECIFIC ANTIGEN (PSA) TARGET DNA

Triamplification was performed in 120 $\mu$l of 20 mM Tris-HCl (pH 8.5), 10 mM $(NH_4)_2SO_4$, 0.1 mg/ml BSA, 2 mM NAD 0.1% Triton X100, 2 MM $MgCl_2$, 200 $\mu$M each dNTP, $10^{-11}$ M template, 250 nM forward primer, 250 nM reverse primer labeled with FAM, 500 nM blocker labeled with Rhod, 6 units of Pfu-exo$^-$ DNA polymerase (polymerase without 3'-5' exonuclease activity; Stratagene) and 30 units of Ampligase™ DNA ligase (Epicentre Technologies, Madison, Wis.). PCR amplification was performed using the same conditions, except that blocker and ligase omitted from the PCR reaction mixture.

Thermal cycling was performed using denaturation for 5 min at 94° C., followed by 35 cycles of 30 sec at 95° C. and 2 min 60° C. The PCR was completed with a final 6 min extension at 60° C.

As a first control, a similar triamplification reaction was performed in the absence of DNA template. As a second control, the reaction mixture was not incubated in the thermocycler.

6.3. 3'-5' EXONUCLEASE TREATMENT

Four units of T4 DNA polymerase that had 3'-5' exonuclease activity were added to the amplified DNA or control probe in 120 µl of the amplification buffer and incubated at 37° C. for 15 min, unless otherwise indicated.

6.4. ENERGY TRANSFER MEASUREMENTS

Energy transfer measurements were made on a Shimadzu RF-5000 spectrofluorophotometer. The excitation wavelength was 488 nm and the emission spectra were taken between 500 and 650 nm.

7. EXAMPLE 1

DNA POLYMERASE COPIES A DNA TEMPLATE WITH RHODAMINE MODIFICATION

Figure 13A:
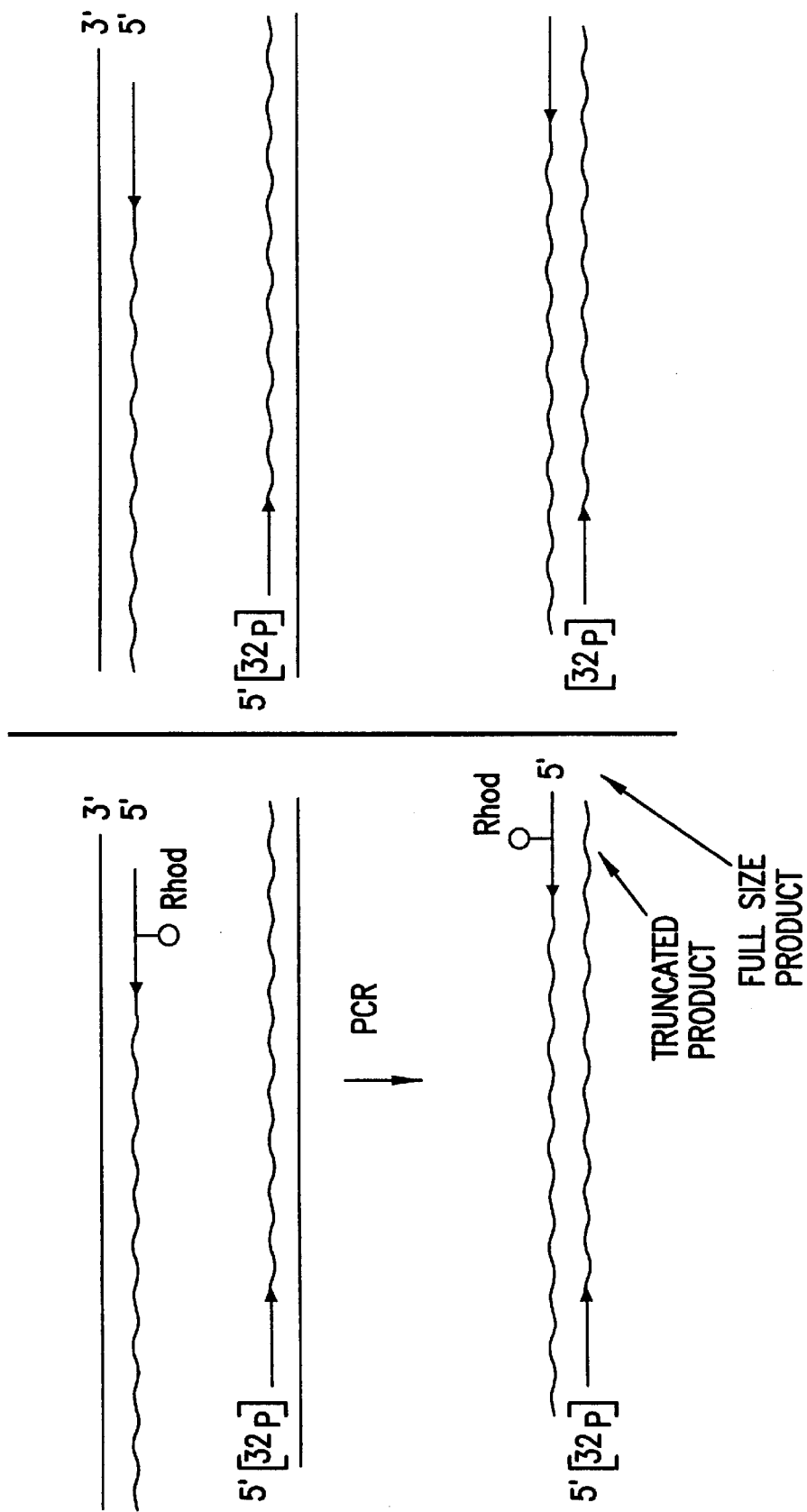

This experiment (FIG. 13A) was conducted to determine the effects of modification of a DNA template with rhodamine on the activity of DNA polymerase. If rhodamine labeling of the reverse primer were to block the incorporation of dNTP, elongation of the forward primer would stop at the base opposite the modification. In this case, the two strands of amplified product would be of different sizes: the one with incorporated forward primer would be shorter.

Figure 13B:
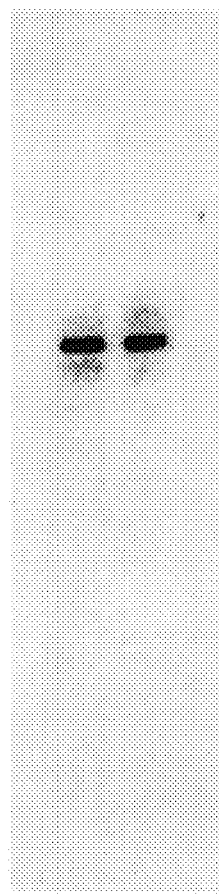

A PCR amplification (FIG. 13A) was performed using the conditions for triamplification described in Section 6, but without using blocker. As illustrated in FIG. 13B, the strands synthesized in the presence of modified and unmodified reverse primer were of the same size, indicating that rhodamine-labeling did not interfere with amplification.

Figure 13C:
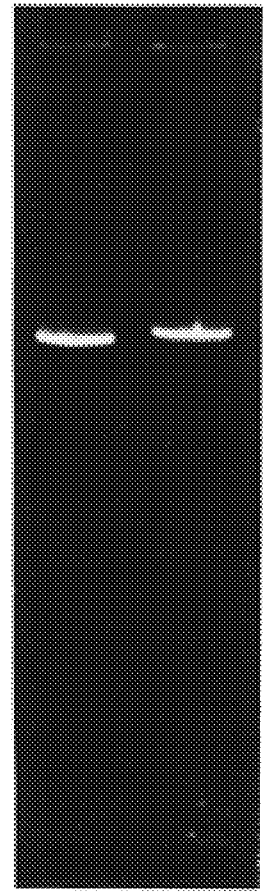

The effects of rhodamine labeling on the yield of the amplification reaction were also estimated. PCR amplification was performed and as a control, unmodified reverse primer was used. As shown on the agarose gel of FIG. 13C, the amount of product was similar when rhodamine-reverse primer or non-modified reverse primer was present.

These results lead to the conclusion that the modifications in the DNA template do not affect the elongation reaction catalyzed by DNA polymerase.

8. EXAMPLE 2

MODIFICATION OF A REVERSE PRIMER DOES NOT AFFECT THE REACTION CATALYZED BY DNA LIGASE

Figure 14A:
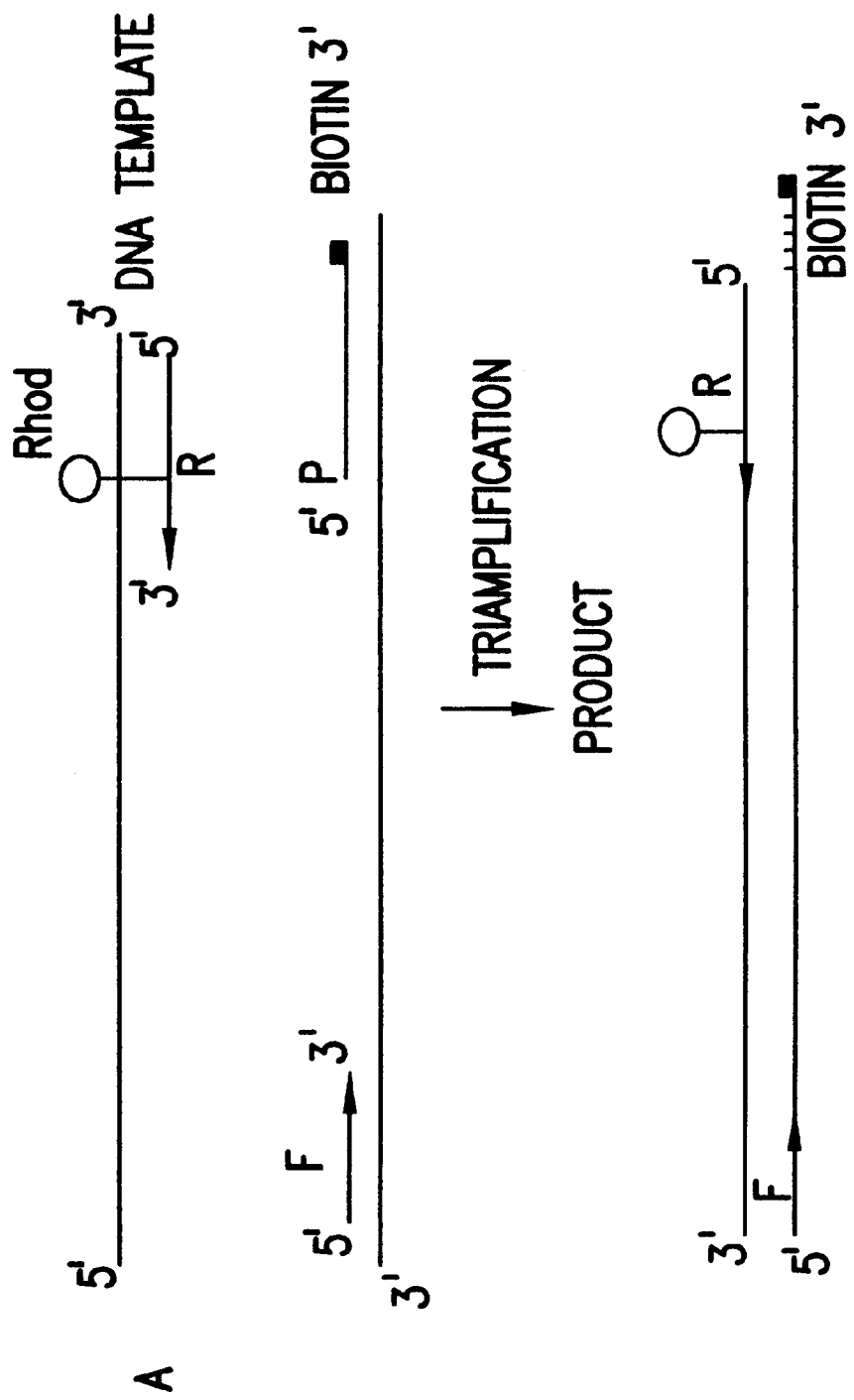

Since triamplification uses thermostable DNA-ligase for amplification, it was important to determine whether the modification of primers affects ligation efficiency. Triamplification was performed as described in Section 6 with rhodamine-labeled reverse primer. As shown in FIG. 14A, the blocker had four nucleotides plus biotin on its 3'-end that extended it beyond the reverse primer sequence.

In cases in which the extended forward primer was ligated to the blocker, the resulting strand would be expected to be approximately 4 nucleotides longer than the opposite strand, which would have incorporated the extended reverse primer. If no ligation took place and instead the blocker was displaced, then both strands would be expected to be of the same length. By using [$^{32}$P]-labeled forward or reverse primer in parallel experiments, the efficiency of ligation was estimated.

Figure 14B:
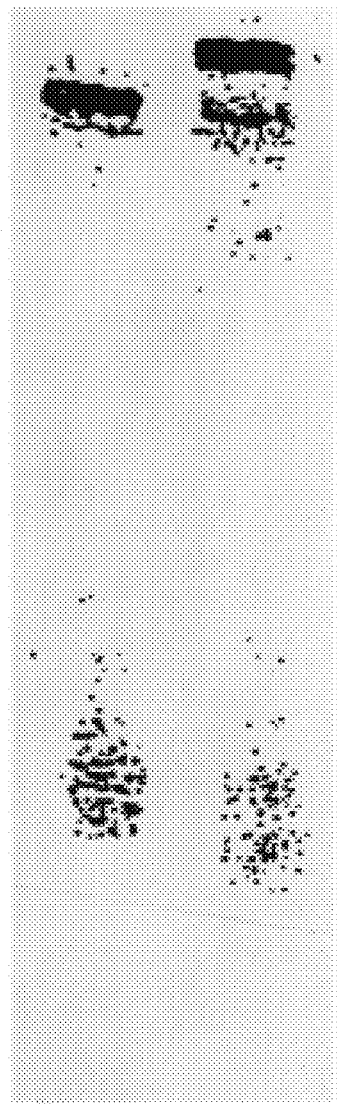

As shown in FIG. 14B, most of the product with labeled forward primer was longer than the strand with labeled reverse primer, indicating that there was no significant effect of modification on the ligation reaction.

9. EXAMPLE 3

EXONUCLEASE CAN REMOVE A NUCLEOTIDE RESIDUE LABELED WITH RHODAMINE

Figure 15A:
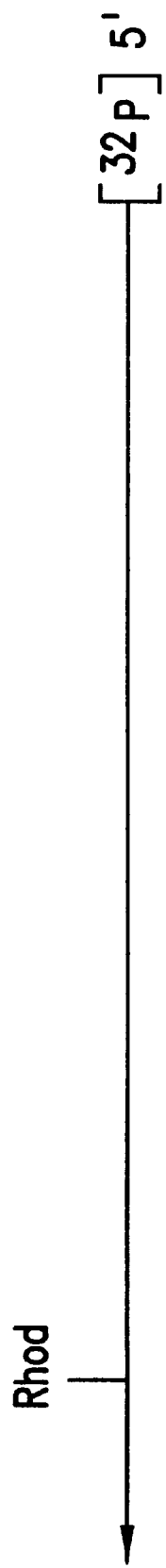
Figure 15B:
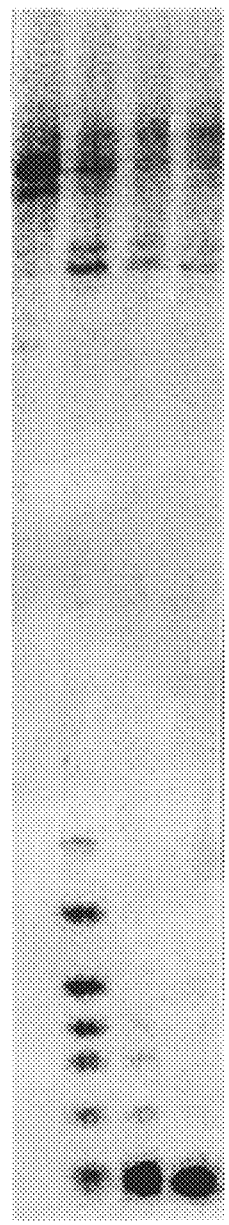

Exonuclease hydrolysis of a [$^{32}$P]-labeled reverse primer labeled with rhodamine (FIG. 15A) was performed in an amplification reaction mixture in a PCR amplification using the methods described in Section 6. T4 DNA polymerase with 3'-5' exonuclease activity was used. Products of hydrolysis were analyzed on a 15% denaturing polyacrylamide gel. The results presented in FIG. 15B demonstrate nearly quantitative hydrolysis of the modified oligonucleotide after 5 minutes. Similar results were obtained when a [$^{32}$P]-labeled reverse primer labeled with rhodamine was in complex with blocker.

10. EXAMPLE 4

DETECTION OF AMPLIFICATION PRODUCT BY ENERGY TRANSFER AFTER NUCLEASE TREATMENT

To detect the triamplification product by FRET between the reverse primer labeled with FAM and the blocker labeled with rhodamine, the triamplification and the subsequent exonuclease treatment were performed as described in Section 6. As a control, the triamplification reaction was also performed in the absence of DNA template.

Figure 16:
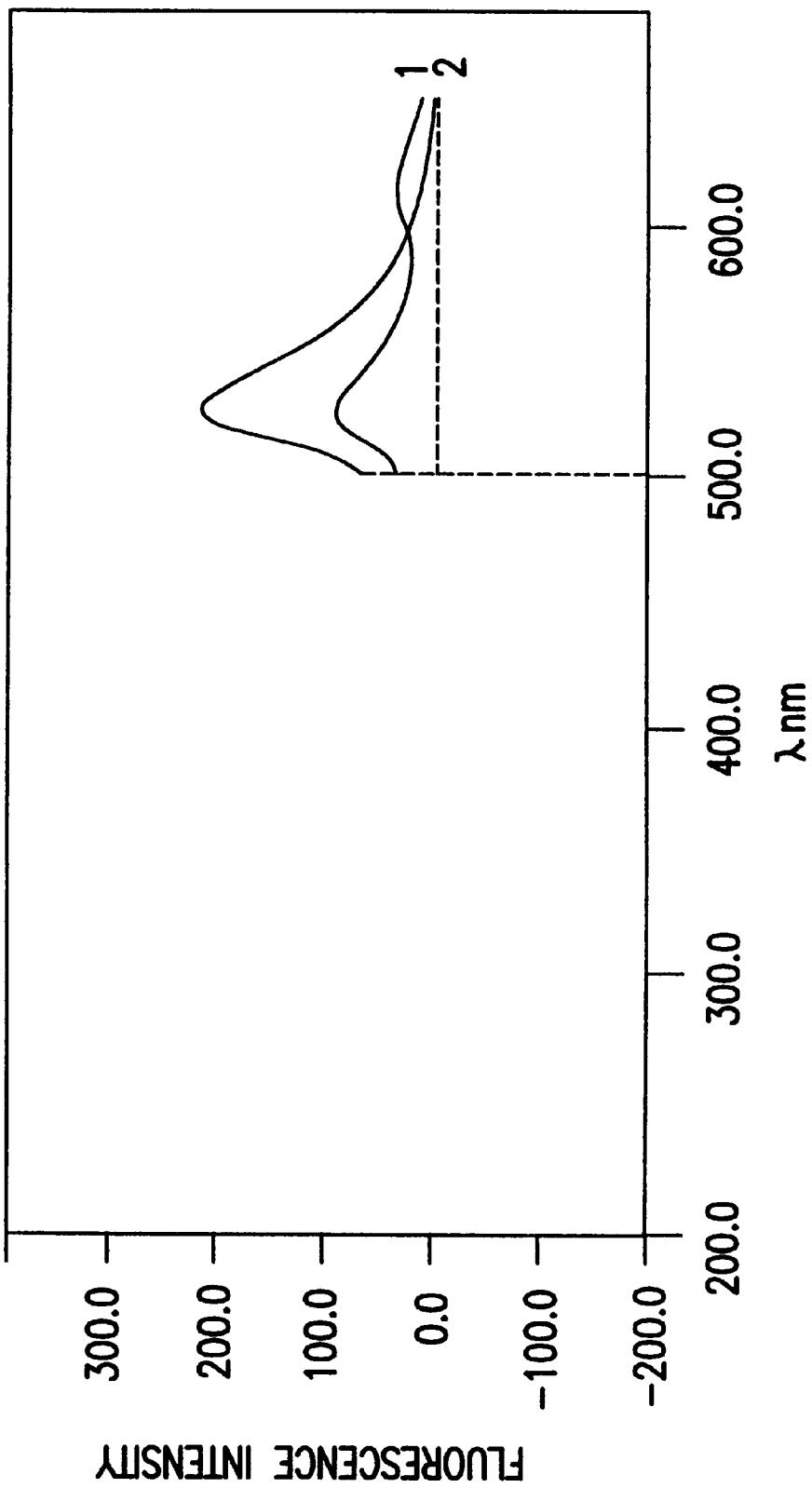

Emission spectra are presented in FIG. 16. The FRET signal at 605 nm was emitted by the double-stranded amplification product (FIG. 16, Spectrum 1) whereas no FRET signal was emitted from the control reaction run without DNA template (FIG. 16, Spectrum 2).

11. EXAMPLE 5

DETECTION OF AMPLIFICATION PRODUCT BASED ON DIFFERENT THERMOSTABILITY OF AMPLIFIED PRODUCT AND BLOCKER/REVERSE PRIMER COMPLEX

The goal of this experiment was to determine whether a specific temperature could be found at which free blocker and reverse primer were no longer in duplex, so that no energy transfer could occur between them. At this temperature, however, the double-stranded triamplification product would still remain in duplex, so that the primers incorporated into it would generate a FRET signal.

Figure 17A:
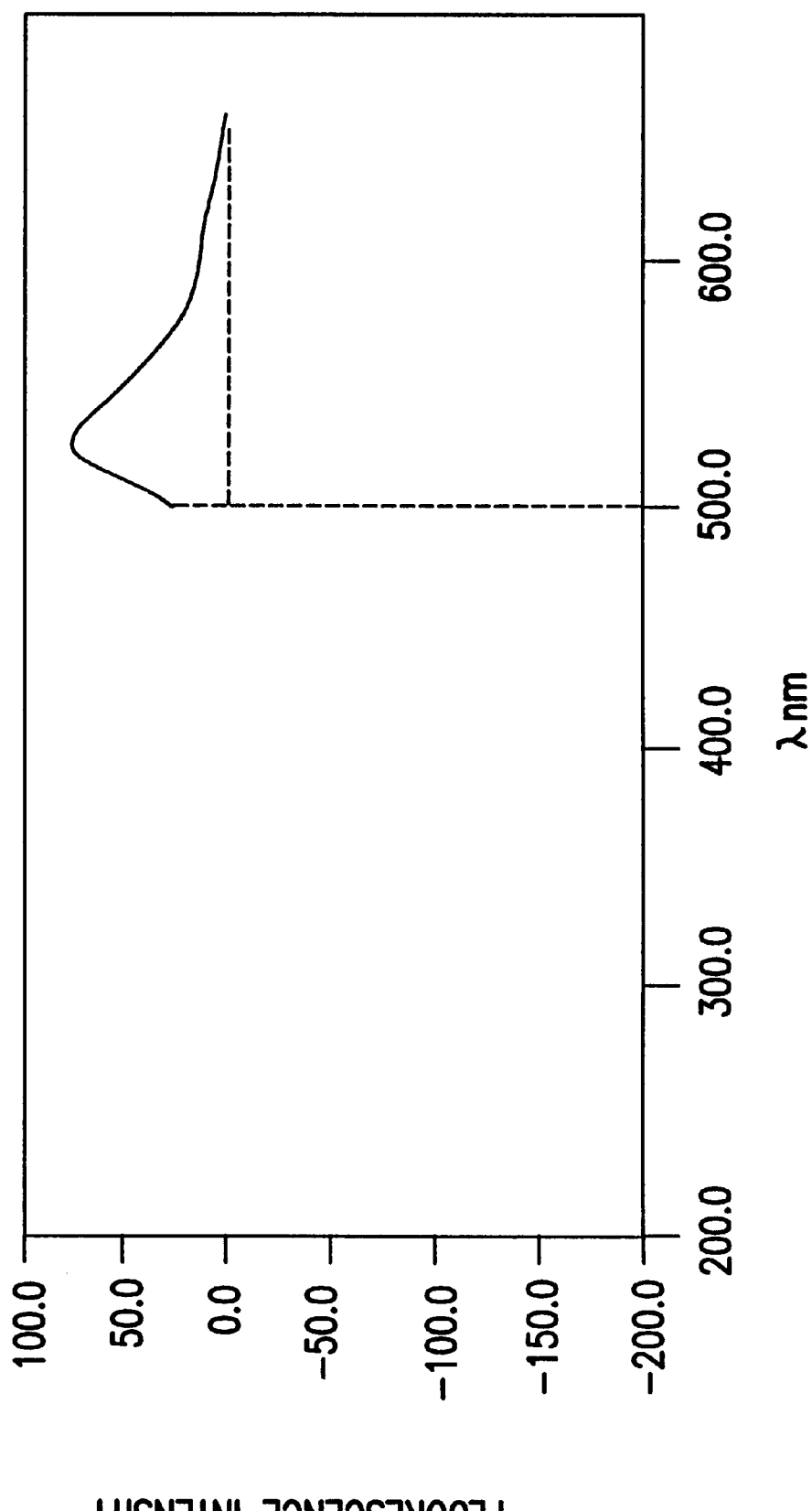
Figure 17B:
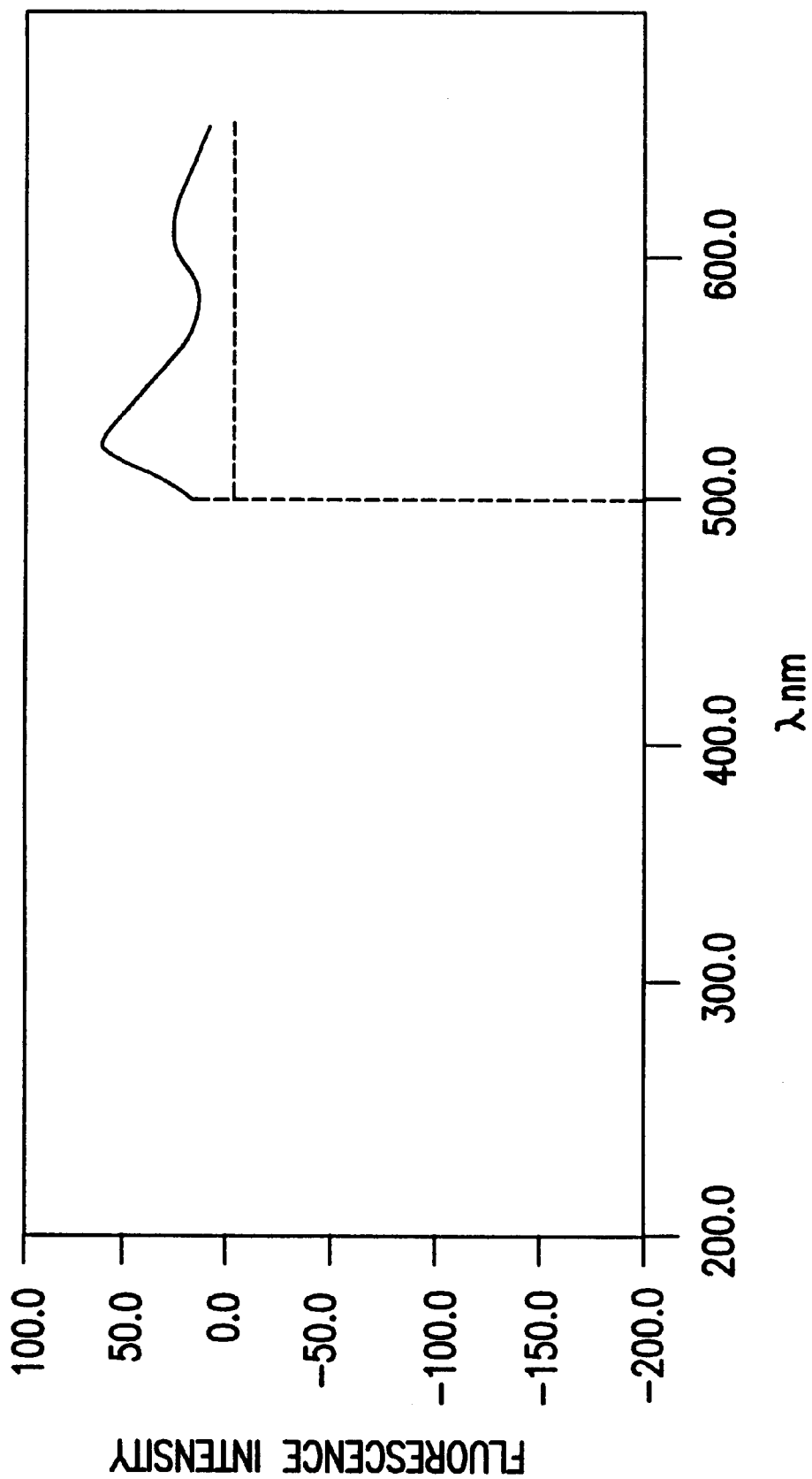

Triamplification was performed as described in Section 6. A control reaction was run in the absence of DNA template. After amplification, reaction mixtures were heated to 75° C. and emission spectra were taken. The results indicate that at this temperature, there was no signal from non-amplified primers (FIGS. 17A–B). However, emission of rhodamine at 605 nm (i.e., a FRET signal) from the amplified product could be clearly detected.

12. EXAMPLE 6

CLOSED-TUBE FORMAT USING HAIRPIN PRIMERS FOR AMPLIFICATION AND DETECTION OF DNA BASED ON ENERGY TRANSFER

12.1. SUMMARY

A new method for the direct detection of PCR-amplified DNA in a closed system is described. The method is based on the incorporation of fluorescence resonance energy transfer-labeled primers into the amplification product. The PCR primers contain hairpin structures on their 5' ends with donor and acceptor moieties located in close proximity on the hairpin stem. The primers are designed in such a way that a fluorescent signal is generated only when the primers are incorporated into an amplification product. A signal to background ratio of 35:1 was obtained using the hairpin primers labeled with FAM as a donor and DABCYL as a quencher. The modified hairpin primers do not interfere with the activity of DNA polymerase, and both thermostable Pfu and Taq polymerase can be used. This method was applied to the detection of cDNA for prostate specific antigen. The results demonstrate that the fluorescent intensity of the amplified product correlates with the amount of incorporated primers, and as little as ten molecules of the initial template can be detected. This technology eliminates the risk of carry-over contamination, simplifies the amplification assay, and opens up new possibilities for the real-time quantification of the amplified DNA over an extremely wide dynamic range.

12.2. INTRODUCTION

Polymerase chain reaction (PCR) and other nucleic acid amplification techniques provide a tool for the geometric amplification of minute amounts of initial target sequences (reviewed in Mullis and Faloona, 1987, Methods in Enzymology 155: 335–350; Landegren, 1993, Trends Genet. 9: 199–204). The extreme sensitivity of DNA/RNA amplification methods has encouraged the development of diagnostics for the early detection of cancer and infectious agents. However, drawbacks to the clinical use of nucleic acid amplification include the possibility of false-positive results due to carry-over contamination, and false-negative results caused by unsuccessful reactions and/or nonstandardized reaction conditions (Orrego, 1990, in Innis et al. (eds.), PCR Protocols, A guide to methods and applications, Academic Press, San Diego, Calif., pp. 447–454).

A major source of carry-over contamination are amplification products from previous amplification reactions. Due to the extreme sensitivity of PCR, even minimal contamination can generate a false positive result, and accordingly, several approaches have been devised to deal with this problem. These include incorporation of dUTP with subsequent treatment with uracil N-glycosylase (Longo et al., 1990, Gene 93: 125–128), incorporation of ribonucleotides into the PCR primers followed by base treatment (Walder et al., 1993, Nucleic Acids Res. 21: 4339–4343) or the use of isopsoralen derivatives which undergo a cycloaddition reaction with thymidine residues upon exposure to UV light (Cimino et al., 1991, Nucleic Acids Res. 19: 88–107). However, a simpler and more certain solution to the problem would be a closed system, where both the amplification reaction and the detection step take place in the same vessel, so that the reaction tube is never opened after amplification. In addition, the "closed tube" format significantly simplifies the detection process, eliminating the need for post-amplification analysis by such methods as gel electrophoresis or dot blot analysis.

The method described infra is designed to measure directly amplified DNA by incorporation of labeled oligonucleotide primers into the reaction product. The conformational transitions that the primers undergo serve as switches for energy transfer between two labels. In this method, the donor and acceptor (quencher) moieties are both attached to a hairpin structure on the 5' end of the amplification primer. The primers are designed in such a way that the fluorescent signal is generated only when the labeled oligonucleotides are incorporated into the double-stranded amplification product. This highly sensitive method may be used to obtain quantitative or qualitative results. Applications for this system to the detection of a specific DNA sequence include, in addition to PCR, triamplification, nucleic acid sequence-based amplification (NASBA), and strand displacement amplification.

12.3. MATERIALS AND METHODS

Oligonucleotide Primers

The following oligodeoxynucleotides complementary to the 172 bp segment of human prostate specific antigen (PSA) cDNA were chemically synthesized: 5'-CCCTCAGAAGGTGACCAAGTTCAT (SEQ ID NO:11), as an upstream primer, and 5'-GGTGTACAGGGAAGGCCTTTCGGGAC (SEQ ID NO:12), as a downstream primer. The structures of the upstream hairpin primers with energy transfer labels are shown in FIGS. 24A–G. FAM was incorporated into the 5' end of hairpin primers by using FAM phosphoramidite in the last step of the chemical synthesis. A modified T-base was introduced into a designated position by the use of Amino-Modifier C6 dT (Glen Research), and the DABCYL was attached to the primary amino group as described by Ju et al. (1995, Proc. Natl. Acad. Sci. USA 92: 4347–4351). Labeled oligonucleotides were purified by HPLC.

Preparation of PSA cDNA

The human PSA-expressing LNCaP cell line (American Type Culture Collection) was used in the experiments. LNCaP cells were diluted with lymphocytes isolated from whole blood at ratios ranging from 1 LNCaP cell to $10^2$ lymphocytes to 1 LNCaP cell to $10^6$ lymphocytes. Messenger RNA was isolated using the Dynal purification kit. cDNA was synthesized from the isolated mRNA using reverse transcriptase (Appligene) and oligodT$_{12\text{-}18}$ primers (Pharmacia) according to the recommended protocol.

PCR Conditions

Amplification of the PSA cDNA was performed in 100 μl of 20 mM Tris-HCl (pH 8.5), 50 mM KCl, 2 mM MgCl$_2$, 200 μM each dNTP, 500 nM each of the upstream and the downstream primers, and 5 units of the Pfu$^{exo-}$ DNA polymerase (which lacks 3'-5' exonuclease activity; Stratagene). Thermal cycling was performed with a 5 min denaturation at 94° C., followed by 20–40 cycles of 30 sec at 95° C., 45 sec at 60° C. and 1.5 min at 72° C., and completed with a final 5 min extension at 72° C.

The PCR product was purified using QIAquick Spin PCR Purification Kit (Qiagen) and cloned into pUC19 plasmid. MDE™ gels (FMC BioProducts) were used for the gel-based detection of the PCR products. Electrophoresis in a 6% polyacrylamide gel with 7M urea, and subsequent quantification on a PhosphorImager-SP (Molecular Dynamics) was used to estimate the amount of primer incorporated into the amplification product.

Fluorescence Detection

A Shimadzu RF-5000 spectrofluorophotometer was used to measure the fluorescence spectra of the individual samples. The 100 μl reaction mixture was diluted to 500 μl with 20 mM Tris-HCl, pH 8.5, 50 mM NaCl, and 2 mM MgCl$_2$, and placed into a 10×3 cuvette (NSG Precision Cells, Inc.) at room-temperature. For the FAM/DABCYL (4-(4'-dimethylaminophenylazo) benzoic acid) FRET pair, a 488 nm excitation wavelength was used and a spectrum was taken between 500 and 650 nm. The fluorescent PCR product was also visualized by placing the tube directly against a UV transilluminator image analysis system (Appligene), and photographed with a mounted camera using a D540/40 filter (Chroma Technology).

12.4. RESULTS

Experimental Design of PCR with Hairpin Primers

In this method, a hairpin structure is present on the 5' end of one (or both) of the PCR primers (FIG. 1). The sequence of the hairpin stem and loop may be partially complementary to the target DNA sequence, but this is not necessary. There are two moieties attached to the stem sequence of the hairpin: a quencher on the 5' end of the hairpin and a fluorophore on the opposite side of the hairpin stem. The positions of the fluorophore and the quencher may be switched, depending on the availability of the commercial precursors of these moieties. DABCYL is a nonfluorescent chromophore whose absorption spectrum overlaps with the emission spectrum of FAM. When stimulated by light of peak wavelength of 488 nm, FAM emits fluorescence of peak wavelength 516 nm. However, when DABCYL is located sufficiently close to the donor fluorophore, the energy can be transferred to DABCYL and dissipated as heat. Therefore, when the modified primer is in a "closed" configuration (hairpin), the FAM and DABCYL are in close proximity, and the emission of the fluorescein is quenched by DABCYL.

During the first cycle of PCR (FIG. 2), the primers are extended and become templates during the second cycle. Since the hairpin structures are very stable (Varani, 1995, Annu. Rev. Biophys. Biomol. Struct. 24: 379–404), the stems are unlikely to be melted during the annealing step of the PCR on every target molecule. In this case, when the DNA polymerase lacking 5'-3' exonuclease activity reaches the 5' end of the hairpin stem, it will displace it and copy the sequence. Thus, the hairpin primer will be linearized by incorporation into the double-stranded helical structure during PCR, the donor and acceptor will be about 20 nucleotides (~70 Å) apart, resulting in no significant energy transfer between them (Selvin, 1995, Methods Enzymol. 246: 300–334), and the fluorescence from the FAM will be markedly enhanced.

Sequence and Spectroscopic Properties of the Hairpin Primer

Figures 18A, 18B:
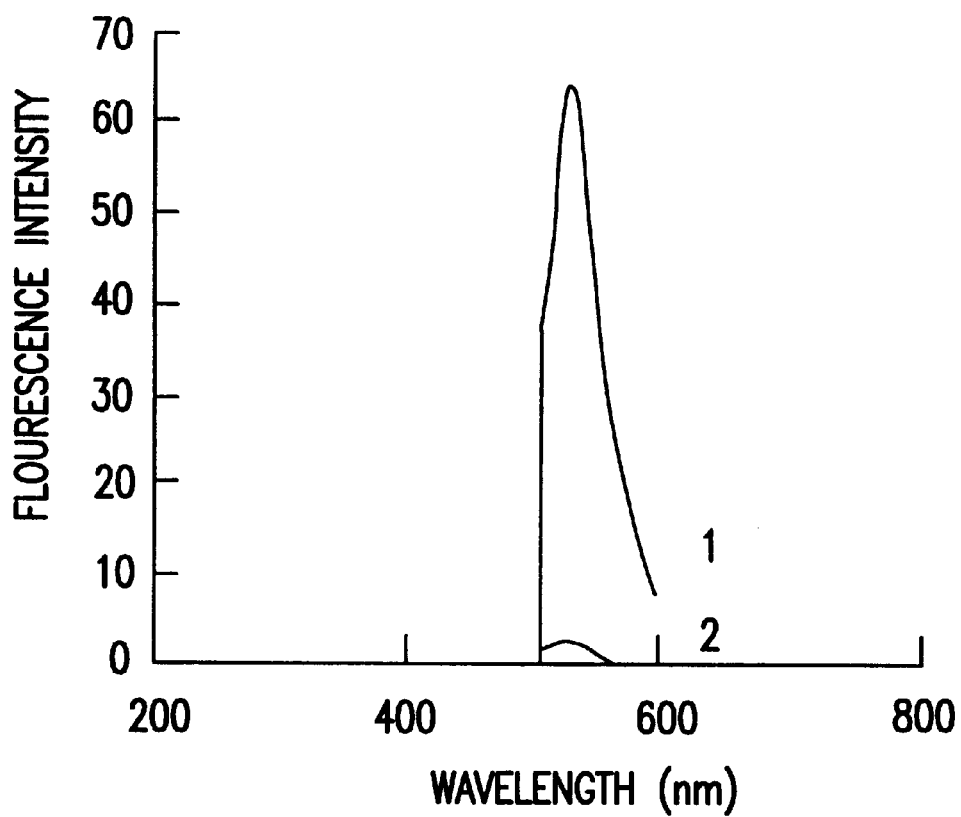

The structure of the hairpin primer for the amplification of cDNA for prostate specific antigen (PSA) is shown in FIG. 18A (SEQ ID NO:10). The primer consists of a 12 nucleotide long single-stranded priming sequence, a 7 bp stem, and a 6 nucleotide loop. The fluorescent moiety (FAM) is located on the 5' end of the primer and a quencher (DABCYL) is across from FAM on the opposite strand of the stem sequence. FIG. 18B presents the emission spectra of the FAM labeled hairpin primer before and after the incorporation of DABCYL. With no quencher present, FAM that is excited at a wavelength of 488 nm emits a peak wavelength of 516 nm. When the same oligonucleotide is also labeled with DABCYL, the fluorescence energy is transferred to the quencher and a much lower peak is detected at 516 nm. The residual fluorescence of the FAM/DABCYL-labeled oligonucleotide is partially caused by the presence of small quantities of oligonucleotides labeled with FAM alone. Therefore an extensive HPLC purification of the labeled oligonucleotides was very important for the low background in subsequent experiments.

Similar results were obtained with rhodamine as a quencher (data not presented). As a quencher, however, DABCYL has an advantage of being a non-fluorescent chromophore: it absorbs the energy of the fluorescein without emitting light itself. As a result, the emission of the fluorescein may be detected more precisely, without interference from the emission of the acceptor.

Use of Hairpin-oligonucleotides as PCR Primers

Figure 19:
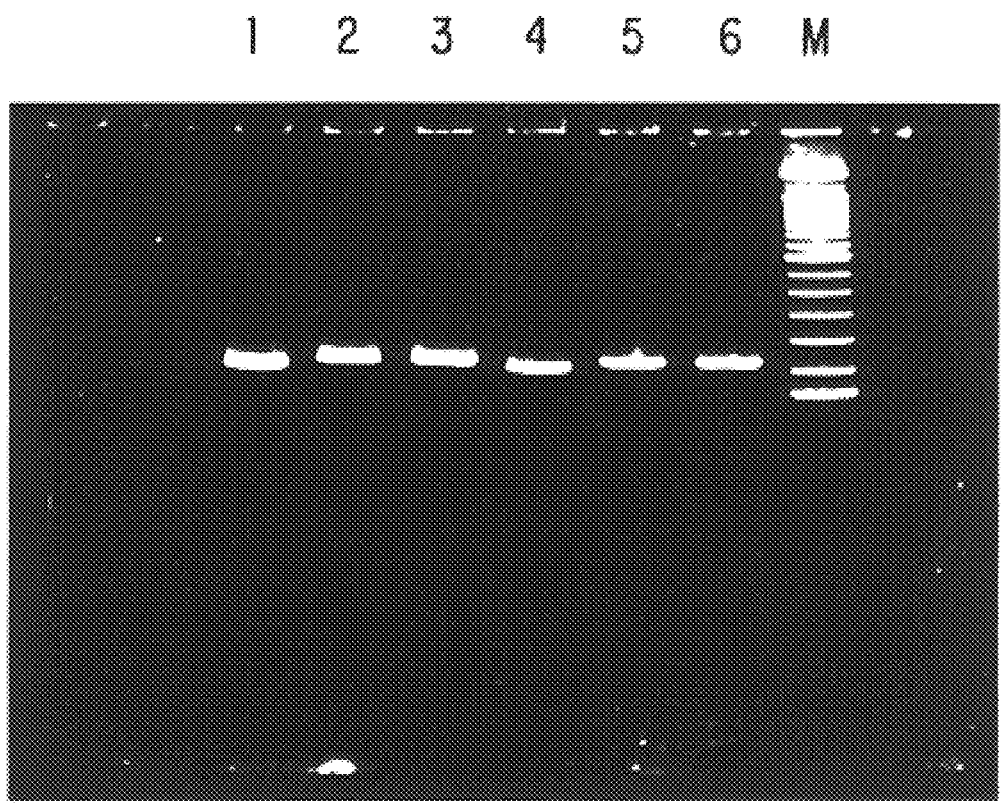

PCR of the fragment of PSA cDNA was performed using thermostable Pfu$^{exo-}$ DNA polymerase. Total cDNA from human PSA-expressing LNCaP cells mixed with lymphocytes was used for amplification. The preliminary experiments using ethidium bromide-stained gels for the assay showed that one PSA cell per $10^5$ lymphocytes could be detected. For quantification purposes, the PCR product was cloned and used to compare the efficiency of amplification in the presence of the hairpin primer with that for the control primer, which lacks the hairpin structure and modifications. FIG. 19 shows that the amount of amplified product was similar for the control primer, the hairpin primer containing FAM alone and the hairpin primer labeled with the FAM/DABCYL FRET pair.

Figure 20A:
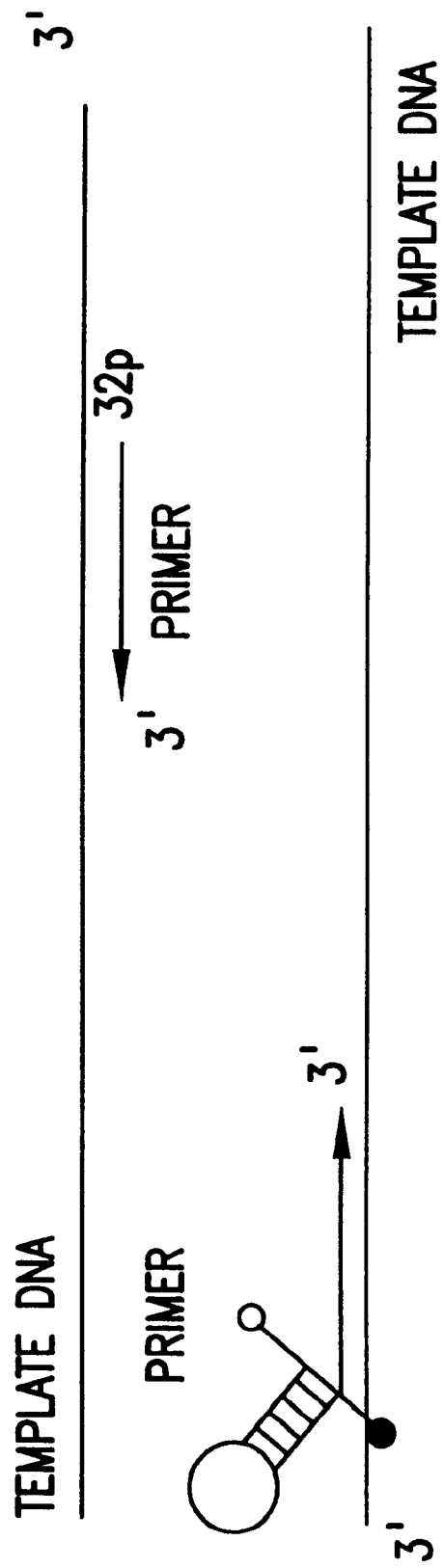

A crucial requirement for the method is the linearization of the hairpin primer during amplification. Therefore DNA polymerase must be able to synthesize the strand complementary to the hairpin primer all the way through the hairpin to its 5' end. The following experiment was conducted to determine whether modifications of the structure of the hairpin primer affect the subsequent synthesis of the full-length PCR product. PCR amplification of PSA cDNA was performed with two primers: an upstream FAM/DABCYL-labeled hairpin primer and a downstream primer labeled with $^{32}$P on its 5' end (FIG. 20A). An upstream primer without the hairpin structure was used as a control.

If the structure and/or the modifications of the hairpin primer creates an obstacle for DNA polymerase, this primer will not be copied all the way to its 5' end, and the [$^{32}$P]-labeled strand will be shorter than the corresponding strand synthesized in the presence of the control primer.

Figure 20B:
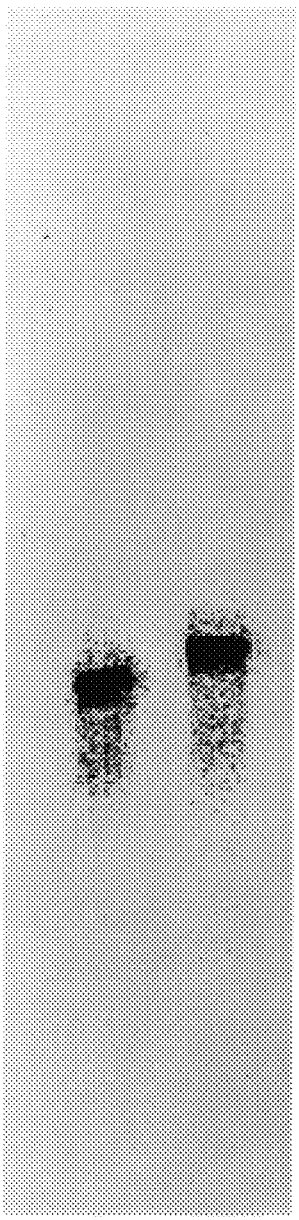

To estimate the length of the individual strands, denaturing gel electrophoresis was performed. As illustrated by the results in FIG. 20B, the [$^{32}$P]-labeled strand that was synthesized in the presence of the hairpin primer was longer than the corresponding strand made with the control primer, indicating that DNA polymerase was able to read through the hairpin structure and synthesize a full-length product.

Another important aspect of this method is the thermostability of the hairpin primer. If the oligonucleotide phosphodiester bonds or the linker arms through which donor and/or acceptor are tethered to the oligonucleotide are cleaved as a result of high temperature, the quencher will be separated from the fluorophore and the background will increase. Indeed, when 50 pmoles of the hairpin primer was incubated in a 100 μl reaction for 40 cycles, the background signal increased from 3.8 units to 12 units of fluorescence intensity. However, the observed background was still very low: it comprised only 6% of the fluorescence emitted by 50 pmoles of fluorescein-labeled oligonucleotides (200 units), which was the amount used in the assays.

Monitoring of PCR with Hairpin Primers

Figure 21A:
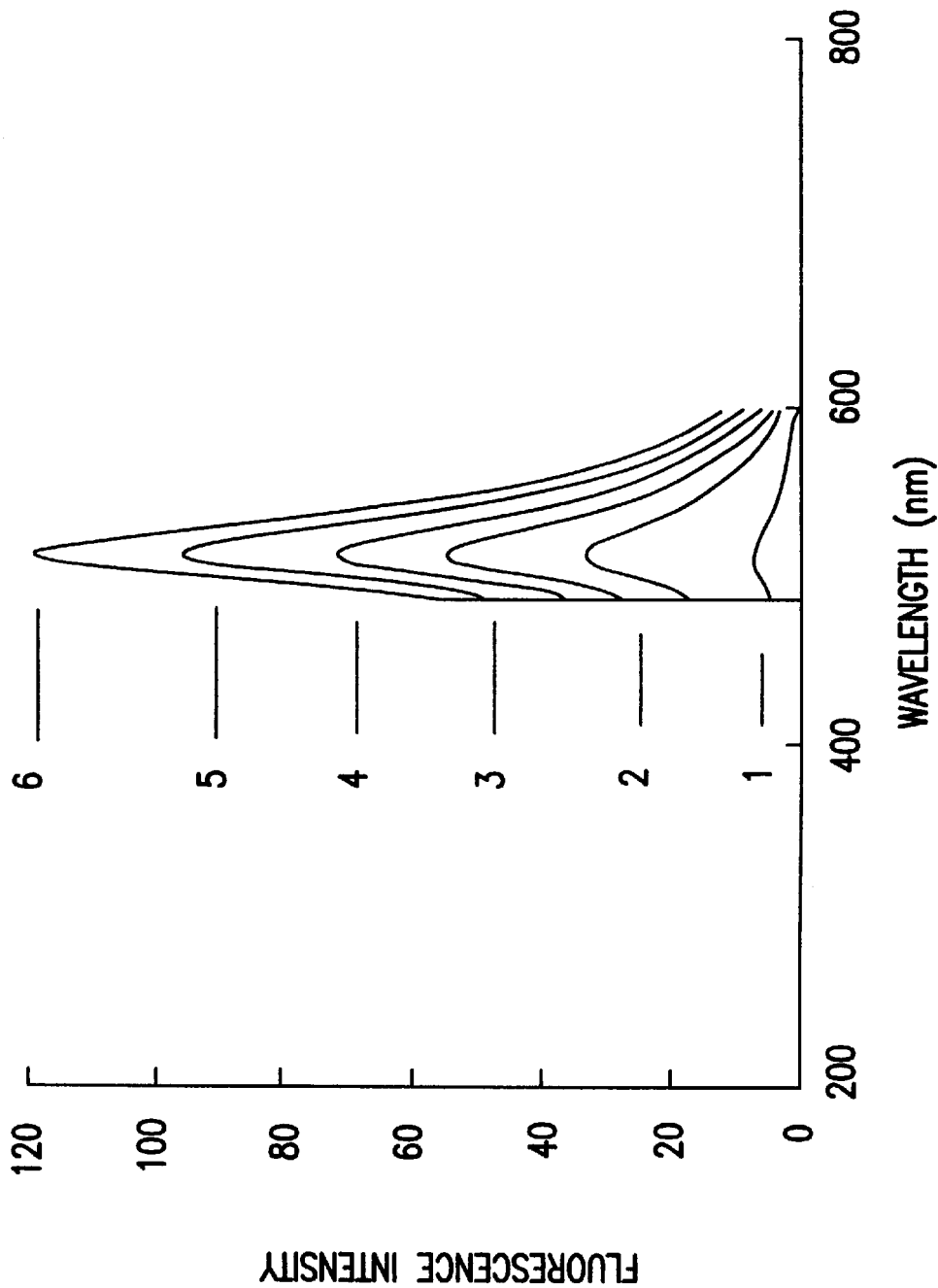

To demonstrate that the fluorescence of the PCR product could be used to monitor the reaction, total cDNA from the mixture of 1 human PSA-expressing LNCaP cell per $10^4$ lymphocytes was amplified with the FAM/DABCYL-labeled hairpin primer. After different numbers of cycles, the fluorescence intensity of the amplified product was determined using a spectrofluorophotometer (FIG. 21A). The results show that after only 20 cycles, the fluorescence intensity increased five times compared to the non-amplified reaction mixture, and a thirty-five-fold increase was detected after 40 cycles of amplification. The same samples were also analyzed by denaturing gel electrophoresis with subsequent quantification on the PhosphorImager to determine the fraction of [$^{32}$P]-labeled primers incorporated into the product.

Figure 21B:
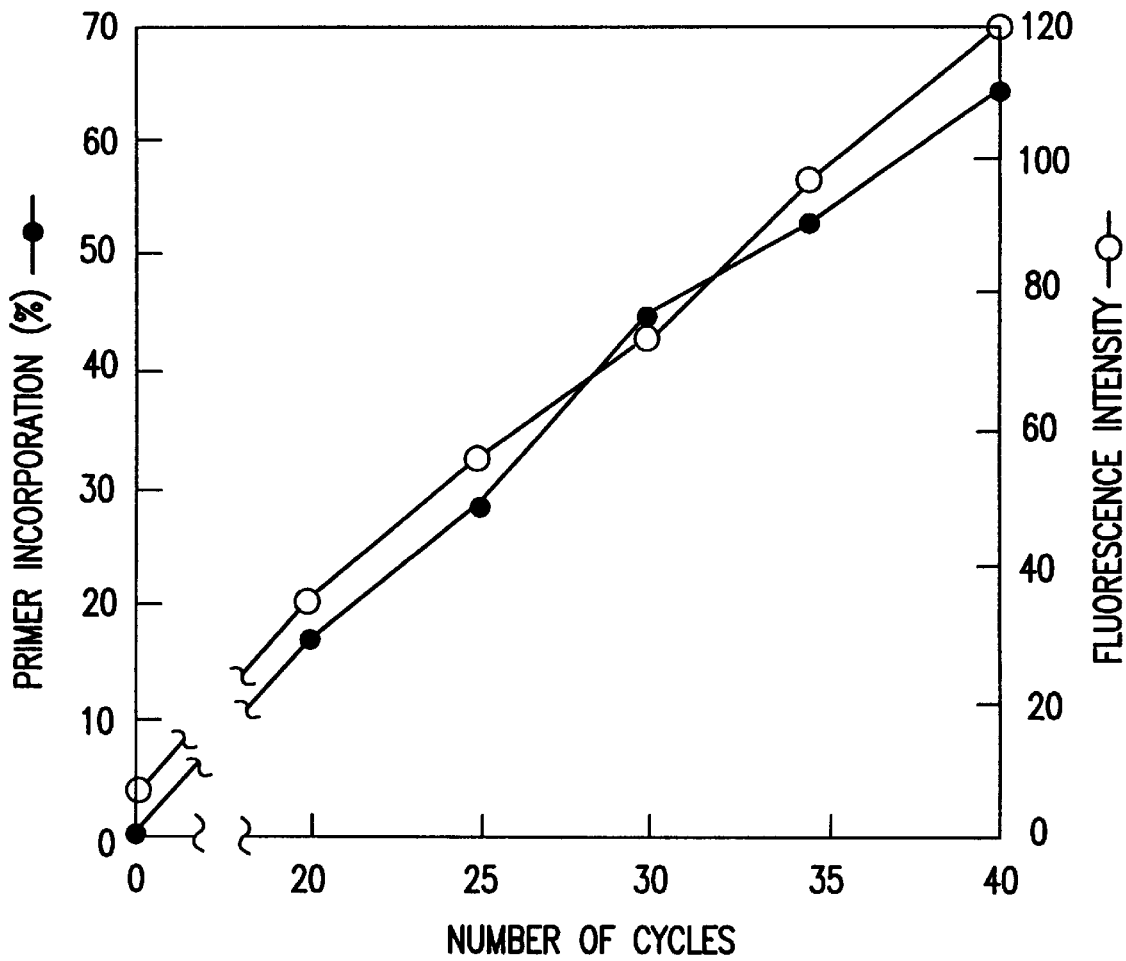

The results in FIG. 21B demonstrate that the fluorescence intensity of the reaction mixture correlates with the amount of primers incorporated into the product.

Figure 22:
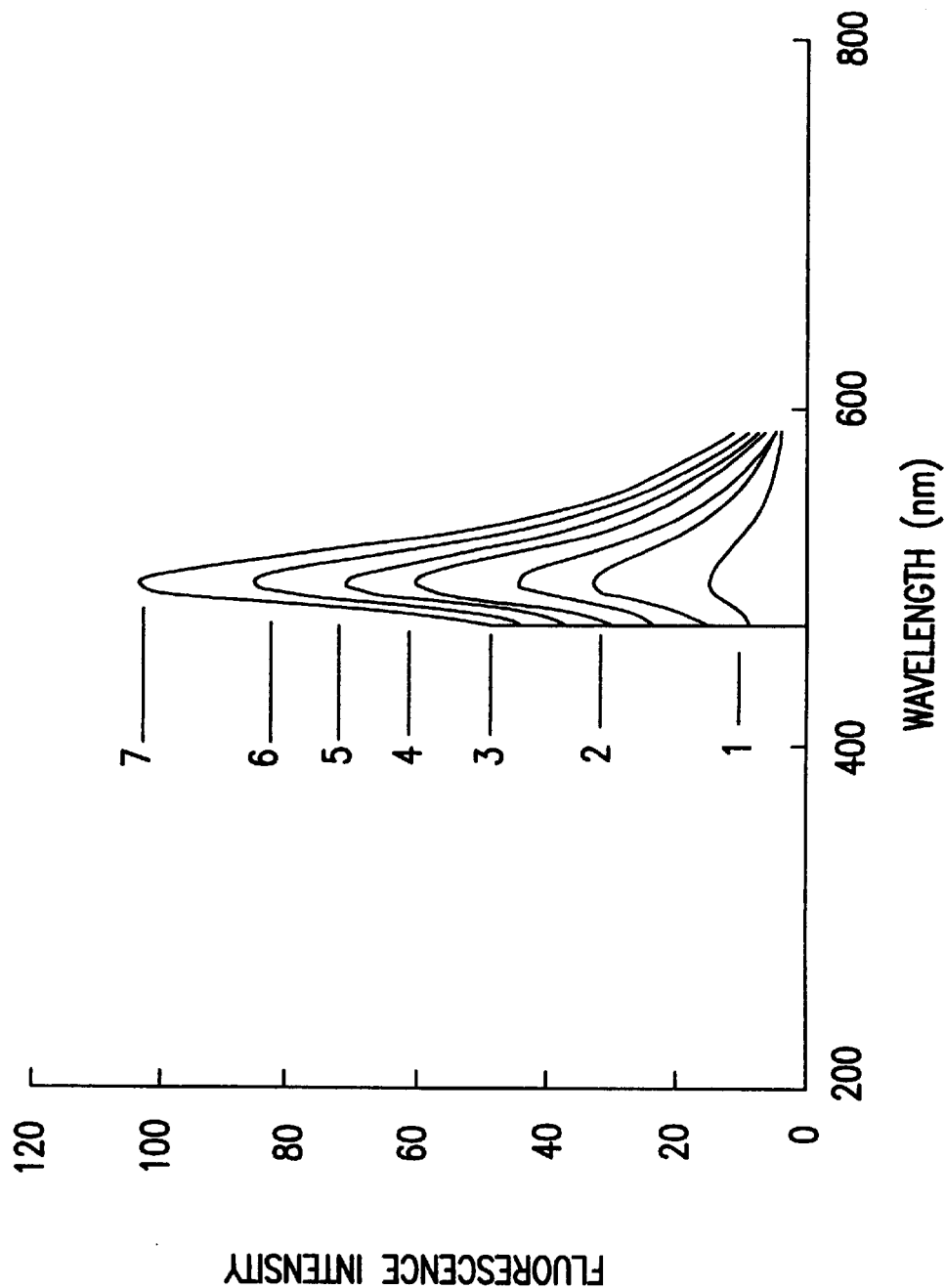
Figure 23:
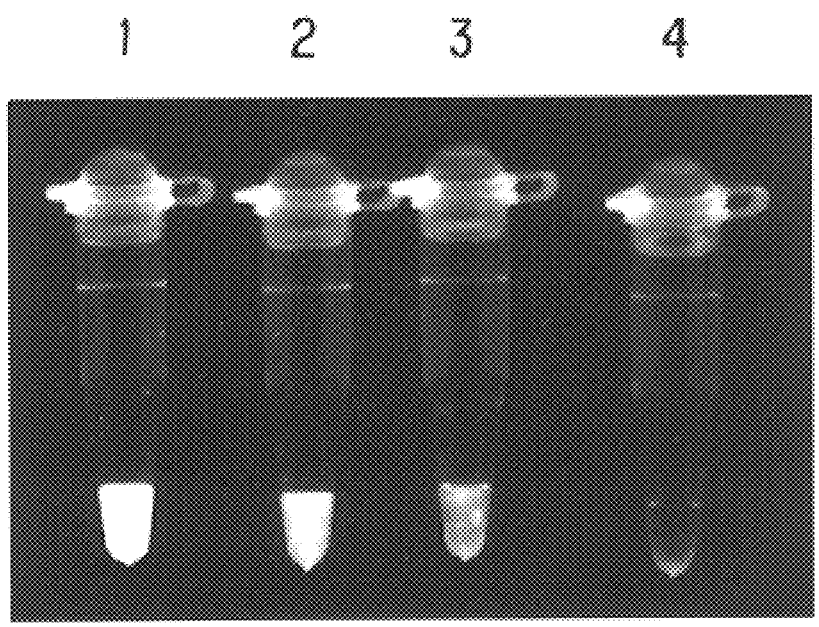
Figure 24A:
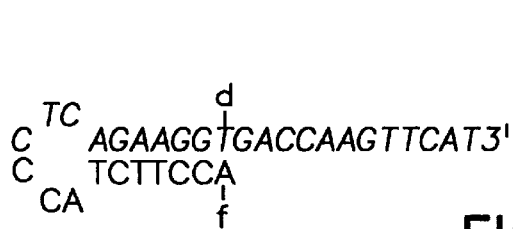
Figure 24B:
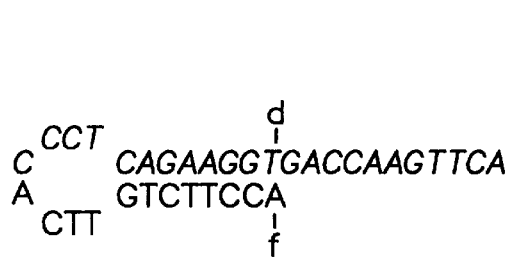
Figure 24C:
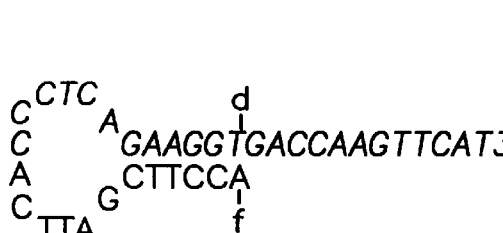
Figure 24D:
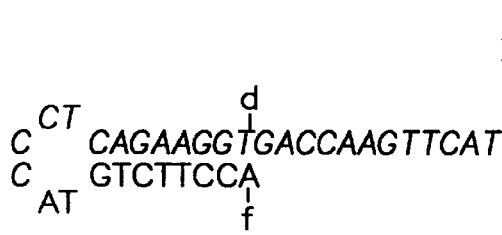

In another experiment, the sensitivity of this method was explored. For quantification purposes, cloned PSA cDNA was used as a template. 40 cycles of PCR were performed with 0, 10, $10^2$, $10^3$, $10^4$, $10^5$, or $10^6$ molecules of cloned PSA cDNA per reaction. The results in FIG. 22 demonstrate that the method is sensitive enough to detect 10 molecules of the initial DNA template with a spectrofluorophotometer. The fluorescent PCR product was also visualized by placing the tube directly on a UV transilluminator equipped with a mounted camera and D540/40 filter. This filter permits the detection of the emission in a narrow wavelength window: between 515 and 560 nm. As shown in FIG. 23, the fluorescence of the PCR reaction performed with $10^4$, $10^5$ and $10^6$ molecules of the initial template could easily be detected by visual inspection of the tubes.

Effect of the Structure of Labeled Hairpin Primer on the Amplification and Detection Several hairpin primers with varying sizes of stem, loop and 3' single-stranded sequences were synthesized to estimate how these parameters might affect the efficiency of the PCR and the signal-to-background ratio. The structures and the relative fluorescent intensities are presented in FIGS. 24A–G. All primers tested had at least an 18-nucleotide sequence complementary to the target, which comprised a 3' single-stranded priming sequence, a 3' stem sequence and part of the loop (highlighted in bold in FIGS. 24A–G).

The length of the 3' single-stranded priming sequence was found to be very important for the efficiency of the hairpin primers in the PCR reaction. Almost no product was detected when the length of the priming sequence was decreased from twelve nucleotides in Structure A to six nucleotides in Structure G (FIG. 24). A possible explanation for this result is that the hairpin structure is the preferred conformation of this oligonucleotide, even at the 60° C. annealing temperature, and that the nucleotides in the stem and loop of the hairpin are not available for hybridization to the target DNA. In this case, the only part of the molecule not involved in the secondary structure is the 3' single-stranded sequence; however, the six nucleotide sequence on the 3' end of Structure G is not long enough to be an efficient PCR primer.

Only minor variations in the amount of product generated were found when the sizes of stem and loop were changed slightly. The PCR was slightly less efficient when the length of the stem was greater than 7 bp. Stabilization of the stem by replacement of an AT-base pair at the 3' end with GC increased the signal-to-background ratio by 10%.

12.5. DISCUSSION

The method for detection of amplification products in a "closed tube" format is an important step towards a PCR-based automated diagnostic system, since it not only reduces the complexity of the reaction, but also eliminates the chances of carry-over contamination and, consequently minimizes the chances of false-positive results. The amplification primer contains a hairpin structure with two labels on its stem that can undergo fluorescence resonance energy transfer. One label is a fluorophore donor and another is a quencher that can absorb energy emitted by the fluorophore. A thirty-five-fold quenching of the fluorescence was observed when the oligonucleotide primers were in the hairpin conformation, so that less than 3% of maximum fluorescence is detected when the primers are not incorporated into the product. The switch from the hairpin to linearized conformation occurs as a result of replication: the 5' end of the stem is displaced by DNA polymerase, a complementary strand is synthesized and the hairpin can no longer be formed. In the incorporated primers, the distance between the fluorophore and the quencher is around 20 base pairs, which is close to 70 Å, the distance at which energy transfer is negligible (Selvin, 1995, Methods Enzymol. 246: 300–334) and so the quantitative emission of the fluorophore can be detected.

The main advantage of this method is the generation of the fluorescent signal by the product itself, rather than by the hybridized probe, as in previous methods (Holland, et al., 1991, Proc. Natl. Acad. Sci. USA 88: 7276–7280; Lee et al., 1993, Nucleic Acids Res. 21: 3761–3766; Tyagi and Kramer, 1996, Nature Biotechnol. 14: 303–309). This keeps background low and allows the real-time quantification of the amplified DNA over an extremely wide dynamic range. In addition, the detection does not require special buffer or temperature conditions that are necessary for methods involving hybridization. The discrimination between a long double-stranded DNA product and the short hairpin primer is so efficient that the signal-to-background ratio will be the same over a wide temperature range under a variety of reaction conditions.

This method can be applied to many amplification systems in which a single-stranded oligonucleotide is incorporated into the double-stranded product, and is compatible with any thermostable DNA polymerase. The present example used Pfu$^{exo-}$ DNA polymerase, an enzyme without 5'-3' and 3'-5' exonuclease activity. Similar results were obtained with Taq polymerase, which has 5'-3' exonuclease activity (data not shown). 5'-3' exonuclease activity is a part of the excision-repair function of some DNA polymerases, and it will not attack a free primer. However, if the extended hairpin primer still maintains its hairpin conformation when annealed to the template DNA, then DNA polymerase will hydrolyze the 5' end of the hairpin stem, and the 5' nucleotide with the tethered donor or acceptor will be released into the solution. In either case, replication or hydrolysis, the donor fluorophore will be separated from the acceptor, quenching will be eliminated, and the fluorescence signal from the amplification product will be detected, allowing any thermostable DNA polymerase to be used for the proposed amplification/detection method.

The thirty-five-fold signal-to-background ratio presented in this example can probably be increased even further. Published data suggest that when the fluorophore and the quencher are covalently linked to each other, 200-fold quenching may be achieved (Wang et al., 1990, Tetrahedron Lett. 31: 6493–6496). This implies that placing FRET labels in closer proximity to one another on the stem structure will increase the efficiency of quenching. This goal may be achieved by several approaches, such as variation of the linker arms, changing the positions of the labels, or using FRET pairs in which the donor and acceptor have some affinity to each other. Another way to improve the system is to increase the thermostability of the FRET-labeled oligonucleotides to prevent an increase in the background during amplification due to the spontaneous release of the labels into the solution.

The method described presented in this example can be applied to any diagnostic procedure in which the presence of the target nucleic acid is to be detected either qualitatively or quantitatively. It may be applied to the detection of infectious disease agents and microorganism contamination of food or water, as well as to the detection of some forms of cancer. An important step in the development of any application of this method is optimization of the structure of the primers and cycling conditions, since any side product can give a signal. However, optimization is facilitated by the fact that the size and purity of the product can be confirmed by gel electrophoresis, since the DNA amplified with the labeled hairpin primers can be analyzed by any of the traditional methods.

The present example demonstrates the utility of this method for the detection of cDNA of prostate specific antigen. The results show that the specificity and the sensitivity of detection are comparable to that of other amplification-based methods: as few as ten molecules of the initial target can be detected. This method can also be used for a "multiplex" analysis in which several targets are amplified in the same reaction. For this purpose, hairpin primers labeled with different fluorophores can be used. For clinical applications, in which a large number of samples are to be tested, a fluorescence plate reader could be used to read the assay results, either separately or coupled with the PCR machine.

13. EXAMPLE 7

ASSAY FOR THE METHYLATION STATUS OF CpG ISLANDS USING PCR WITH HAIRPIN PRIMERS

13.1. MATERIALS AND METHODS

Genomic DNA was obtained from OH3 (unmethylated P16 DNA) and HN 12 (methylated P16 DNA) cell lines (acquired from Drs. S. B. Baylin and D. Sidransky, The Johns Hopkins Medical Institutions) and treated with bisulfite (Herman et al., 1996, Proc. Natl. Acad. Sci. USA, 93: 9821–9826).

Three sets of PCR primers (FIG. 26) that amplify respectively bisulfite-treated unmethylated DNA (Uup and Ud (SEQ ID NOS:19 and 20, respectively)), bisulfite-treated methylated DNA (Mup and Md) (SEQ ID NOS:21 and 22, respectively), and the DNA not treated with bisulfite (wild type, WT) (Wup and Wd) (SEQ ID NOS:23 and 24, respectively) were chemically synthesized. One of the two primers in each set had a hairpin structure at its 5' end, labeled with FAM/DABCYL.

PCR was performed in 40 $\mu$l of 10 mM Tris-HCl (pH 8.3), 50 mM KCl, 2 mM $MgCl_2$, 0.25 mM each dNTP, 0.5 $\mu$M each primer, 100 ng of the corresponding DNA template and 1 unit of AmpliTaq Gold™ polymerase (Perkin Elmer). Thermal cycling was performed using denaturation for 12 min at 94° C. (these conditions were also required for the activation of the AmpliTaq Gold™ polymerase), followed by 35 cycles of 45 sec at 95° C., 45 sec at 65° C. and 1 min at 72° C. The PCR was completed with a final 5 min extension at 72° C.

13.2. RESULTS

The reaction products were analyzed as described in Section 6. After PCR amplification, the fluorescence intensities of the reaction mixtures were measured. The fluorescence intensity of the reaction mixture amplified in the presence of DNA template (+) differed significantly from the fluorescence intensity of the reaction mixture amplified in the absence of DNA template (−) (Table 2). For example, when a U-primer set (for amplification of a sequence of U (bisulfite-treated unmethylated) DNA, see Table 2) was used with U DNA, it was amplified and the intensity of signal differed significantly from the intensity of the reaction mixture with no template. Similarly, use of an M-primer set led to amplification of M (bisulfite-treated methylated) DNA, and use of a W-primer set led to amplification of W (wild-type chemically unmodified) DNA.

TABLE 2

The fluorescence intensity (expressed as fluorescence units) in 20 $\mu$l of the reaction mixture after PCR in the presence (+) and in the absence (−) of DNA template. U, unmethylated genomic DNA that underwent chemical modification with bisulfite; M, methylated genomic DNA that underwent chemical modification with bisulfite; W, genomic DNA that did not undergo chemical modification.

| U DNA | | M DNA | | W DNA | |
|---|---|---|---|---|---|
| + | − | + | − | + | − |
| 18 | 6 | 20 | 6 | 23 | 9 |

13.3. CONCLUSION

The results show that MET-labeled hairpin primers may be used in an amplification reaction to detect, reliably and sensitively, methylated or unmethylated DNA.

14. EXAMPLE 8

PCR AMPLIFICATION USING A UNIVERSAL HAIRPIN PRIMER

14.1. INTRODUCTION

This example presents experiments in which a universal hairpin primer was used, along with two selected linear primers, Primer 1 and "tailed" Primer 2, to prime a PCR amplification (see Section 5.2.1). The universal hairpin primer was incorporated into the amplification product and was not ligated to one of the two linear primer sequences. The 3' sequence of the universal hairpin primer was identical to the 5' sequence of one of the pair of linear forward and reverse primers used in the amplification, and this 5' sequence (sequence "A" on Primer 2 in FIG. 5) and was not complementary to the target sequence.

During the first cycle of PCR, Primer 1 (FIG. 5), which was complementary to a target DNA (+) strand was extended. Primer 2 (FIG. 5) had a 3' portion that has a sequence complementary to the target sequence (−) strand and a 5' portion, designated "A" in FIG. 5, that had a sequence that was not complementary to the target sequence. (Sequences for Primer 1 and Primer 2 appear below in Section 14.2.) Sequence A was 15 nucleotides in length.

During the second cycle, the product of the extension of Primer 2 (shown by the arrow in FIG. 5) became a template for Primer 1. Primer 1 was extended and the amplification product acquired a sequence, designated "A'," complementary to sequence A.

During the third cycle, the A sequence of the universal hairpin primer annealed to the A' sequence of the amplification product from the previous cycle. The 3'-end of the template was extended, the universal hairpin primer unfolded and was copied, the quencher and fluorophore were separated, and a fluorescent signal was emitted from the amplification product.

During the fourth cycle, the extended universal hairpin primer became a template for Primer 1. During the extension of Primer 1, the hairpin unfolded and was copied, the quencher and fluorophore were separated, and a fluorescent signal was emitted from the amplification product.

Conditions of the reaction and the concentrations of the primers were optimized, so that >80% of the PCR product contained incorporated universal primer and was detectable by fluorescence detection.

14.2. MATERIALS AND METHODS

PCR Conditions.

In one set of experiments (see Table 3, below), amplification of prostate specific antigen (PSA) CDNA cloned into pUC 19 plasmid, Chlamydia genomic DNA, and the P16 gene present in total human genome, was performed using PCR amplification with a universal hairpin primer labeled with Flu/DABCYL (see "Sequence of the universal hairpin primer," below), and three pairs of linear Primer 1 and linear tailed Primer 2 specific for PSA, Chlamydia, and P16, respectively. $10^6$ molecules of PSA and Chlamydia sequences, and 100 ng of human DNA were used per reaction.

Amplifications were performed in 20 μl of 20 mM Tris-HCl (pH 8.8), 50 mM KCl, 1.5 MM $MgCl_2$, 0.001% gelatin, 200 μM each dNTP, 0.5 μM of Primer 1, 0.1 μM of Primer 2, 0.5 μM of the universal hairpin primer labeled with Flu/DABCYL and 1 unit of Taq DNA polymerase (Takara, Shiga, Japan). For amplification of the P16 gene, however, a Hot Start™ amplification was performed, using AmpliTaq Gold™ DNA polymerase (Perkin Elmer) instead of Taq. For optimum amplification conditions, the concentration of the tailed primer (Primer 2) was kept low in order to obtain a majority of PCR amplification product with incorporated universal hairpin primer.

Thermal cycling was performed with 5 min of denaturation at 94° C., followed by 20–40 cycles: 20 sec at 95° C., 30 sec at 55° C. and 1 min at 72° C., and completed with a final 5 min extension at 72° C. The required number of cycles depends on the concentration of the initial target. A PCR reaction with a universal hairpin primer usually requires 3–5 cycles more than regular PCR to obtain a comparable amount of product. Universal hairpin primer only starts to incorporate at cycle 3 (FIG. 5), and there is also competition from the tailed primer throughout the amplification.

Two control reactions were run per each DNA target. Control 1 contained no tailed primer in the reaction mixture. No product would be expected in this case if the universal hairpin primer was specific for the sequence complementary to the tail sequence only and could not hybridize to any other sequence of the DNA target.

Control 2 contained no DNA target in the reaction mixture.

In a second set of experiments (see Table 4), a set of PCR amplifications was run using varying concentrations of the PSA cDNA target and the PSA-specific Primer 1 and tailed Primer 2, and the universal hairpin primer. Another set of (conventional) PCR amplifications was run using PSA-specific Primer 1 and untailed Primer 2.

PCR in this second set of experiments was performed in 40 μl of 10 mM Tris-HCl (pH 8.3), 50 mM KCl, 2 mM $MgCl_2$, 0.25 mM each dNTP, 0.5 μM each primer, 100 ng of the corresponding DNA template and 1 unit of AmpliTaq Gold™ polymerase (Perkin Elmer). Thermal cycling was performed using denaturation for 12 min at 94° C. These conditions were also used for the activation of the AmpliTaq Gold™ polymerase, and were followed by 35 cycles of 45 sec at 95° C., 45 sec at 65° C. and 1 min at 72° C. The PCR was completed with a final 5 min extension at 72° C.

The products of the amplification using linear unlabeled primers was visualized on ethidium bromide stained gels.

Fluorescence Detection.

A Shimadzu RF-5000 spectrofluorophotometer was used to measure the fluorescence spectra of the individual samples. A 5 μl aliquot of the reaction mixture was diluted to 600 μl with 20 mM Tris-HCl, pH 8.8, 50 mM KCl, 2 mM $MgCl_2$ and placed into a 10×3 mm cuvette (NSG Precision Cells, Inc., Farmingdale, N.Y.) at room temperature. For the fluorescein/4-(4'-dimethylaminophenylazo) benzoic acid (DABCYL) FRET pair, a 488 nm excitation wavelength was used and a spectrum was taken between 500 and 650 nm.

The fluorescence intensities were determined after subtracting the background. The background was defined as the fluorescence of the universal hairpin primer in the reaction mixture before the PCR amplification reaction was run.

When the amount of the initial target was not too low (1000 molecules or more), the fluorescent PCR amplification product was also visualized by placing the tube directly against a UV transilluminator image analysis system (Appligene, Strasbourg, France), and photographed with a mounted camera using a green D540/40 filter (Chroma Technology, Brattleboro, Vt.).

Alternatively, to obtain quantitative results, a fluorometric plate reader can be used. In this case the reaction can be performed in a sealed 96-well PCR plate. The same plate is then transferred into the plate reader, and the fluorescence emitted from the top of the plate is measured. The measurement can be done after the desired amount of cycles. If the signal will not be strong enough the same plate can be transferred back to the PCR machine and more cycles can be performed after the short (1–2 min) preheat step. To determine the exact amount of the initial target, the proper internal control should be included. A hairpin primer of a different color should be used for the internal control. Quantitation of the initial target can be made easier if a real-time detection PCR machine is used, e.g., an Idaho Light-cycler (Idaho Technology, Inc., Idaho Falls, Id.).

Sequence of the Universal Hairpin Primer.

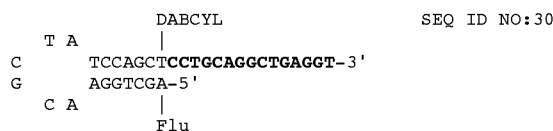

The boldfaced sequence is identical to the tail on the specific primers.

Sequences of Specific Linear Primers.

In each sequence, the tail sequence of Primer 2 appears in bolded lowercase letters.

PSA:

Primer 1:

5'-ggt gta cag gga agg cct ttc ggg ac SEQ ID NO:31

Primer 2:

5'-cct gca ggc tga ggt gaa ggt gac caa gtt cat SEQ ID NO:32

Chlamydia genomic DNA

Primer 1:

5'-gta cta gag gac tta cct ctt ccc SEQ ID NO:33

Primer 2:

5'-cct gea ggc tga ggt ctg taa caa caa gtc agg tt SEQ ID NO:34

P16

Primer 1:

5'-CAG AGG GTG GGG CGG ACC GC SEQ ID NO:35

Primer 2:

5'-cct gca ggc tga ggt CCC GGG CCG CGG CCG TGG SEQ ID NO:36

14.3. RESULTS

As shown in Table 3, a universal hairpin primer can be used in a PCR amplification reaction to specifically detect three different targets. All three genomic sequences, PSA, Chlamydia genomic DNA, and P16, were amplified, and their amplification products were detected by measuring the fluorescence spectra of the amplification reactions with a spectrofluorophotometer.

TABLE 3

The fluorescent intensities of the PCR reaction mixtures with universal hairpin primer on different DNA targets.*

| Target | Complete reaction | no tailed primer control 1 | no DNA control 2 |
|---|---|---|---|
| PSA | 303 | 15 | 10 |
| Chlamydia genomic DNA | 286 | 14 | 5 |
| P16 gene | 140 | 10 | 9 |

*The fluorescence intensity was determined after subtraction of background present before the PCR amplification reaction was run.

Figure 28A:
Figure 28B:

In addition, the products of amplification of PSA and Chlamydia were visualized by placing the tubes on a transilluminator and photographing them through a green filter. The results are presented in FIGS. 28A–B. Fluorescence was significantly enhanced after amplification compared to the controls, indicating that the DNA targets had been amplified.

The sensitivity of PCR amplifications using Primer 1, tailed Primer 2, and the universal hairpin primer was compared with that of conventional PCR amplifications using Primer 1 and untailed Primer 2. As demonstrated in Table 4 (below), the sensitivity of a PCR reaction using Primer 1, tailed Primer 2, and the universal hairpin primer is comparable to that obtained in a PCR reaction using Primer 1 and untailed Primer 2. Under optimized conditions and concentrations of the primers, as described in Section 14.2, as little as 10 molecules of the PSA target could be detected using either the universal hairpin primer or the conventional linear (untailed) sequence-specific primers. The fluorescence intensity was determined after subtraction of background present before the PCR amplification reaction was run.

TABLE 4

The fluorescence intensities of the PCR reaction in the presence of specific and universal hairpin primer and different numbers of molecules of the initial PSA DNA target.*

| Number of target molecules per reaction: | 0 | 10 | $10^2$ | $10^4$ | $10^6$ |
|---|---|---|---|---|---|
| Labeled primer | | | | | |
| Specific | 4 | 55 | 165 | 250 | 320 |
| Universal | 7 | 42 | 140 | 220 | 244 |

*The fluorescence intensity was determined after subtraction of background present before the PCR amplification reaction was run.

14.4. DISCUSSION

The results presented in this example demonstrate that there are several distinct advantages of using universal hairpin primers, rather than conventional linear PCR primers, in a PCR amplification.

First, a universal hairpin primer can be used for an amplification with any previously optimized set of PCR primers. Second, the use of the universal hairpin primer permits a closed tube format; amplification and detection are performed in the same tube, without ever opening it. This ensures that there will be no carry-over contamination with amplicon (amplification products from previous reactions) and consequently no false positive results. Such minimization of carry-over contamination is especially important when large numbers of clinical samples are analyzed. In the past, contamination has generally been difficult to avoid when analyzing large numbers of clinical samples and false positive results are harmful. Use of the universal hairpin primers of the invention in closed tube PCR amplifications avoids the possibility of such contamination. Using this closed tube format and the hairpin primers of the invention in a PCR-based assay, at least three different targets can be specifically detected in one assay.

Third, by using the universal hairpin primers of the invention in a PCR amplification, quantitative results can be obtained. One can quantitate the amount of amplification product by using, e.g., a fluorimetric plate reader, provided that proper internal controls are used, e.g., a known number of molecules of a second known target sequence and the corresponding primers for that target.

Fourth, by using the universal hairpin primers of the invention in a PCR amplification, one does not need to perform a time-consuming post-amplification analysis like gel electrophoresis or dot-blot. By omitting this step, one saves 2–3 hours on each set of amplification reactions.

Finally, the results presented here indicate that the universal hairpin primer can be used to amplify the P16 gene. Hence a universal hairpin primer is suitable for inclusion in a kit for the detection of the methylation status of the P16 gene, which is a tumor suppressor.

15. EXAMPLE 9

USE OF HAIRPIN PRIMERS IN A TELOMERIC REPEAT AMPLIFICATION PROTOCOL (TRAP) ASSAY FOR THE DETECTION OF TELOMERASE-POSITIVE CELLS

The present example demonstrates the detection of telomerase-positive cells in which a TRAP assay is used with a hairpin primer of the invention.

15.1. METHODS AND RESULTS

Experiment 1.

A 17 bp-long nucleotide, 5'-ACGCAATGTATGCGT*GG-3' (SEQ ID NO:29), was added to the 5' end of a RP primer (FIG. 30A). FAM was attached to the 5' end of the oligomer and DABCYL was attached to the T* residue. When the intra-chain stem-loop of the hairpin primer formed, FAM and DABCYL residues were positioned opposite one other (FIG. 30A). In this configuration, the fluorescence emission of the 5' FAM was minimal in unincorporated oligomer due to FRET between FAM and DABCYL.

A series of TRAP assays utilizing this hairpin RP primer demonstrated that the 5' modification of the RP does not significantly alter the efficiency of the TRAP assay (FIG. 30B). TRAP assays were performed using TS primer and the RP primer sequence (SEQ ID NO:37) shown in FIG. 30A, with cell extract equivalent to 10,000, 1000, 100, or 10 cells. Three negative controls were also run (FIG. 30B): "No Taq," in which no Taq polymerase was added in the reaction (negative control 1); "CHAPS," in which CHAPS lysis buffer was used instead of cell extract in the reaction (negative control 2); "+H," cell extract from 10,000 cells was heat-treated prior to the assay (negative control 3). Four reaction tubes (0.05 ml per tube) were prepared for each extract or control and PCR amplification in a thermal cycler (cycle conditions: 94° C. for 30 sec and 55° C. for 30 sec)

was performed for the number of cycles indicated in FIG. 30B. At the end of the cycles, the tubes were removed from the heating block of the thermal cycler and stored in the dark until measured for fluorescence. To perform fluorescence measurements, 0.02 ml of the reaction mix was mixed with 0.60 ml of buffer (10 mM Tris-HCl, pH 7.6, 150 mM NaCl, 2 mM $MgCl_2$) and emission at 516 nm excited by 488 nm light was measured with a Shimadzu RF5000U spectrofluorophotometer.

By optimizing the reaction conditions, a very low level of telomerase activity was detected; the sensitivity of the assay is comparable to those of conventional assays that utilize polyacrylamide gel electrophoresis of PR products (FIG. 30B).

Experiment 2.

In the first step of an in situ TRAP assay, a slide is prepared of selected tissues or cells of interest. Unfixed tissues are frozen quickly in liquid nitrogen and frozen sections are prepared by microtome sectioning. Single cell spreads are prepared by centrifugation of cell suspensions utilizing, e.g., Cytospin™ (Shandon Lipshaw Inc., Pittsburgh, Pa.). The prepared slides are then treated with a solution containing RNase-free DNase in 40 mM Tris-HCL pH 7.4, 6 mM $MgC_2$ and 2 mM $CaCl_2$ for 5–15 hours.

A slide sealing system such as Probe-Clips (GraceBio-Labs, Pontiac, Mich.) is used. Probe-Clips are attached on the slides and the specimens are covered with the DNA solution and incubated for 5 to 15 hours. The Probe-Clips, which form a sealed chamber around the specimen without the usage of adhesives or other toxic solvents, can also be utilized in the TRAP extension amplification reaction.

The TRAP assay is run on the samples on the prepared slides following the instructions provided with the TRAPeze™ kit. Experimental conditions for standard in-tube TRAP assays can be used with minor modification. After amplification, the slides are viewed directly under a fluorescence microscope without detection/washing steps after PCR amplification. Cells will only fluoresce if the gene target of interest is amplified.

16. EXAMPLE 10

USE OF HAIRPIN PRIMERS IN AN AMPLIFICATION REFRACTORY MUTATION SYSTEM (ARMS) ASSAY 16.1. INTRODUCTION

Allele-specific PCR was run, using hairpin primers, to amplify the normal sequence and the W64R mutation of the beta-3-adrenergic receptor (B3AR) gene. The normal product of the gene is a G-protein linked receptor that is expressed predominantly in visceral fat. It is believed to be a regulator of resting metabolic rate and lipolysis, and the W64R mutation has been associated with obesity (Clement et al., 1995, New Engl. J. Med. 333: 352–354).

16.2. METHODS

The amplification refractory mutation system (ARMS) assay (Newton et al., 1989, Nucl. Acids Res. 17: 2503–2516) as used for allele-specific PCR. The upstream allelic primers in the ARMS assay had a hairpin format, and used a common downstream primer. The ARMS assay is designed such that there is a mismatch at the 3' end of the primer when the primer is paired to the incorrect allele.

The sequence of the B3AR gene and the allelic primers are shown in Table 5 (below). Boldface type has been used to highlight codon 64 of the B3AR sequence, and the underlined sequences indicate the area for which the allele-specific primers were designed. Hairpin primers were modified at an internal thymine, as indicated in Table 5, using DABCYL as the quencher, and on the 5' end with FAM as the fluorophore.

TABLE 5

Sequence of the B3AR gene target
and the allelic primers used for the ARMS assay W64 Allele:
(5') . . . TGC <u>TGG TCA TCG TGG CCA TCG CCT</u> GGA . . . (3')    SEQ ID NO:38

R64 Allele:
(5') . . . TGC <u>TGG TCA TCG TGG CCA TCG CCC</u> GGA . . . (3')    SEQ ID NO:39

W64 Allelic Primer:

```
            FAM
     T       |
  G    C AGTAGCA (5')
  A      |||||||
  C    G TCATCGT GG TCA TCG TGG CCA TCG CCT (3')         SEQ ID NO:40
     G       |
           DABCYL
```

R64 Allelic Primer:

```
            FAM
     T       |
  G    C AGTAGCA (5')
  A      |||||||
  C    G TCATCGT GG TCA TCG TGG CCA TCG CCC (3')         SEQ ID NO:41
     G       |
           DABCYL
```

Downstream Common Primer:

(5') CCA CTA CCC TGA GGA CCA CC (3')                     SEQ ID NO:42

The ARMS assay was run in 10 mM Tris-HCl, pH 8.3 buffer containing 50 mM KCl, 2 mM $MgCl_2$, 400 µM each dATP, dCTP, dTTP, and dGTP, and 10% dimethylsulfoxide (DMSO). The primers were used at a concentration of 1 µM each, and Taq polymerase (Takara, Shiga, Japan) at 1.5 U per 20 µL reaction. The 20 µL PCR reactions were run on a PE-2400 thermal cycler (PE Applied Biosystems, Foster City, Calif.) for 4 min at 94° C., followed by 35 cycles of 30 sec at 94° C., 30 sec at 55° C. and 30 sec at 72° C., followed by a 10 min incubation at 72° C. and a 4° C. hold.

16.3. RESULTS

Using the reaction conditions described above, cloned normal (W64) and mutant (R64) templates were tested for amplification specificity and yield. A no target negative control was also run with each reaction. After PCR, 3 µL of each PCR reaction was run on a gel and stained with ethidium bromide. Using the PCR system described above, the normal (W64) target only gave a visible band when the normal primer was present and the mutant target (R64) only gave a visible band when the mutant target was present. No background PCR artifacts were observed in the negative control or in the PCR reactions run with the mismatched target. Each PCR reaction was also tested for fluorescence yield by diluting 5 µL from each reaction into 0.6 mL of 15 mM Tris-HCl, pH 8.0, 50 mM NaCl, and 2 mM $MgCl_2$ buffer. The fluorescence of each reaction was measured on a Shimadzu RF-5000U spectrofluorophotometer using an excitation wavelength of 488 nm and an emission wavelength of 516 nm.

After subtracting the background fluorescence of the negative control from each sample, the PCR run with the normal (W64) allelic primer and the normal (W64) target DNA had a relative fluorescence of 37, while fluorescence from the PCR run with the normal (W64) allelic primer and the mutant target (R64) was the same as the negative control. The PCR run with the mutant (R64) allelic primer and the normal (W64) target DNA had a relative fluorescence of 2, and the PCR run with the mutant (R64) allelic primer and the mutant target (R64) had a relative fluorescence of 19. These results indicate good PCR product and fluorescence yield from an allele-specific PCR using hairpin primers with an ARMS design, and the capability of distinguishing normal and mutant alleles based on fluorescence alone, without the need to run gel electrophoresis.

17. EXAMPLE 11

ASSAY FOR THE gag REGION OF THE HIV-1 VIRAL GENOME USING IN SITU PCR WITH HAIRPIN PRIMERS

17.1. INTRODUCTION

HIV-1 provirus is very difficult to detect with standard in situ hybridization but can be routinely and reliably detected after in situ PCR, but with the additional time and expense of hybridization and washing steps. The present example describes methods of the invention that allow for the accurate and sensitive detection of the target directly after the amplification step.

The following methods are used to detect an HIV-1 DNA target, and employ FRET-labeled hairpin primers in situ PCR. These methods avoid the hybridization step and will not lead to false positive results due to DNA repair. Another advantage of this method is that the generation of the fluorescent signal is by the product itself, rather than by the hybridized probe as in previous in situ PCR methods. The primary use of in situ PCR at present is the detection of viral DNA or RNA. Improvement in sensitivity, as provided by using the labeled primers of the invention, will allow for broader applications such as detection of small gene deletions or mutation detection by allele specific in situ PCR.

17.2. MATERIALS AND METHODS

Tissues that comprise a wide range of potentially HIV-1 infected cells, including those from the central nervous system, lymph nodes, and spleen, are assayed for HIV-1 DNA, using the FRET-labeled primers of the invention and standard in situ PCR methods commonly known in the art (see e.g., Nuovo and Bloch, U.S. Pat. No. 5,538,871; Bagasra and Seshamma, 1994, *Protocol: In situ amplification and hybridization*, Second Ed., John Wiley and Sons, Somerset, N.J.).

A pair of upstream and downstream PCR primers (SEQ ID NOS: 43–44, see below) are chemically synthesized and used to amplify a portion of a sequence from the gag region of an HIV-1 viral genome DNA. One or both oligonucleotide PCR primers that are used can have a hairpin structure at the 3' end, labeled with a MET pair, e.g., FAM/DABCYL.

For example, a hairpin primer may be used in which the single-stranded nucleotide sequence at its 3' end comprises the sequence of SEQ ID NO:43 or SEQ ID NO:44 so as to be able to prime synthesis by a nucleic acid polymerase of a nucleotide sequence complementary to a nucleic acid strand comprising the gag target sequence.

An example of such a hairpin primer, BSK38 (SEQ ID NO:26) is shown in FIG. 27. The primer forms a hairpin structure in which MET will occur when the primer is not incorporated into the amplification product. When it is incorporated into the amplification product, its configuration changes (i.e., it is linearized), and, in the case of a FAM/DABCYL FRET pair, quenching is eliminated, and the fluorescence of the donor is detected.

Alternatively, the pair of primers may be MET-labeled linear primers that do not form a hairpin configuration (see Section 5.4).

When one or both primers are linear primers, they may have the following sequences which are complementary to the gag sequence:

Primer SK 38:
  ATAATCCACCTATCCCAGTAGGAGAAAT (SEQ ID NO:43)

Primer SK 39:
  TTTGGTCCTTGTCTTATGTCCAGAATGC (SEQ ID NO:44)

In control experiments, a conventional in situ PCR (e.g., Nuovo, 1997, *PCR In Situ Hybridization: Protocols and Applications*, Third Edition, Lippincott-Raven Press, New York) is run using two linear primers complementary to the gag sequence, e.g., SK 38 (SEQ ID NO:43) and SK 39 (SEQ ID NO:44). Amplification products are detected through an in situ hybridization step using the SK 19 sequence as probe.

SK 19 (hybridization probe):
  ATCCTGGGATTAAATAAAATAGTAA-
  GAATGTATAGCCCTAC (SEQ ID NO:45).

In situ PCR using the FRET-labeled primers of the invention is performed by carrying out the following steps. First, a sample is placed on a glass microscope slide and then fixed by standard methods. Common fixatives include, e.g., ethanol, methanol, methanol:acetic acid, formaldehyde, paraformaldehyde and glutaraldehyde, or any other fixative known in the art.

The sample is optionally pretreated with a protease, e.g., proteinase K, to aid in penetration of amplification reagents. The concentration of protease and time of treatment is determined empirically for each sample.

An amplification cocktail, which consists of nucleotides, hairpin (or linear) primers of the invention, an amplification buffer, and a thermal stable DNA polymerase, e.g., Taq polymerase, is then added. A coverslip or other suitable solution containment device is attached to keep the concentration of the cocktail consistent during subsequent thermal cycling steps. (For general methods and buffer compositions for in situ PCR, see, e.g., Nuovo, 1997, *PCR In Situ Hybridization: Protocols and Applications, Third Edition*, Lippincott-Raven Press, New York; Nuovo, et al., U.S. Pat. No. 5,538,871)

In situ amplification is then performed in a thermal cycler, for e.g., 30–40 cycles, using conditions for annealing and extension previously established by solution PCR, e.g., first thermal cycle, denaturation for 3 min at 94° C., and annealing/extension for 2 min at 55° C; the remaining 39 cycles consist of 1 min denaturation at 94° C. and 2 min annealing/extension.

Since the unincorporated hairpin primers do not produce signal post-amplification, wash steps are reduced or eliminated. This improves sensitivity of detection because no amplification product is lost during post-amplification wash steps.

After PCR amplification, the MET signal intensities of the reaction mixtures are measured using, e.g., a fluorescence microscope. Cells positive for the HIV gag template should show a signal, e.g., fluorescence; cells negative for gag should show no signal.

18. EXAMPLE 12

CHARACTERIZATION OF THE gag REGION OF THE HIV-1 VIRAL GENOME USING IN SITU PCR WITH HAIRPIN PRIMERS 18.1. INTRODUCTION In this example, a series of HIV-1 infected tissues from the spleen, lymph node, brain, and cervix were assayed for the gag region of the HIV-1 viral genome using in situ PCR with hairpin primers.

18.2. MATERIALS AND METHODS

A hairpin primer and a linear primer were chemically synthesized and used to amplify a portion of a sequence from the gag region of an HIV-1 viral genome DNA.

The linear primer used was SK 39 (SEQ ID NO:44).

The hairpin primer used, BSK38 (SEQ ID NO:26) is shown in FIG. 27 (see also Section 17 above). The single-stranded nucleotide sequence of the hairpin primer comprised, at its 3' end, a 3' portion of the sequence of SK 38 (SEQ ID NO:43). The 5' portion of the primer comprised a hairpin labeled with a FAM/DABCYL MET pair. Since the 3' single stranded sequence was complementary to the gag sequence, it served as a primer.

The primer forms a hairpin structure in which MET will occur when the primer is not incorporated into the amplification product. When it is incorporated into the amplification product, its configuration changes (i.e., it is linearized), and, in the case of a FAM/DABCYL FRET pair, quenching is eliminated, and the fluorescence of the donor is detected.

In control experiments, a conventional in situ PCR (Nuovo, 1997, *PCR In Situ Hybridization: Protocols and Applications, Third Edition*, Lippincott-Raven Press, New York) was run using two linear primers SK 38 (SEQ ID NO:43) and SK 39 (SEQ ID NO:44) complementary to the gag sequence in the amplification cocktail (see below). Amplification products were detected through an in situ hybridization step using the SK 19 (SEQ ID NO:45) sequence as probe.

In situ PCR using the linear primer and the FRET-labeled hairpin primer of the invention was performed essentially as described in Section 17 with a few modifications. Tissue sections were affixed to silane coated glass microscope slides and fixed for one week in 10% neutral buffered formalin, then embedded in a paraffin embedding medium using standard methods known in the art. Section were deparaffinized (by incubating with xylene for 5 min, followed by 100% ethanol for 5 min). The sample was pretreated with 2 mg/ml of pepsin for 30 min. 10–20 $\mu$l per sample of an amplification cocktail were then added to the slide, which was then coverslipped with an autoclaved polypropylene coverslip and overlaid with preheated mineral oil.

The amplification cocktail consisted of the following reagents per 50 $\mu$l of cocktail:

5 $\mu$l PCR buffer II (Perkin-Elmer)
9 $\mu$l MgCl$_2$ (final concentration 4.5 mM)
8 $\mu$l dNTP (final concentration 200 $\mu$M each)
1.5 $\mu$l 2% BSA
2 $\mu$l modified SK38 oligonucleotide (final concentration of 0.2 $\mu$M)
2 $\mu$l SK39 oligonucleotide (final concentration of 0.2 $\mu$M)
21.5 $\mu$l DEPC-treated water
1 $\mu$l Taq polymerase (Perkin-Elmer 5 U/$\mu$l)

In situ amplification was then performed in a thermal cycler for 35 cycles using a "hot start" protocol. Taq polymerase was withheld from the amplification cocktail until the block reached 55° C., then the DNA sample was denatured initially by heating at 94° C. for 3 min, after which cycling began, with denaturation for 1 min at 94° C., and annealing/extension for 1.5 min at 60° C.

After PCR amplification, a high stringency wash was performed (60° C. in 15 mM salt and 2% BSA for 10 min after PCR). The MET signal intensities of cells in the samples were then measured using a fluorescence microscope.

18.3. RESULTS

Figure 34:
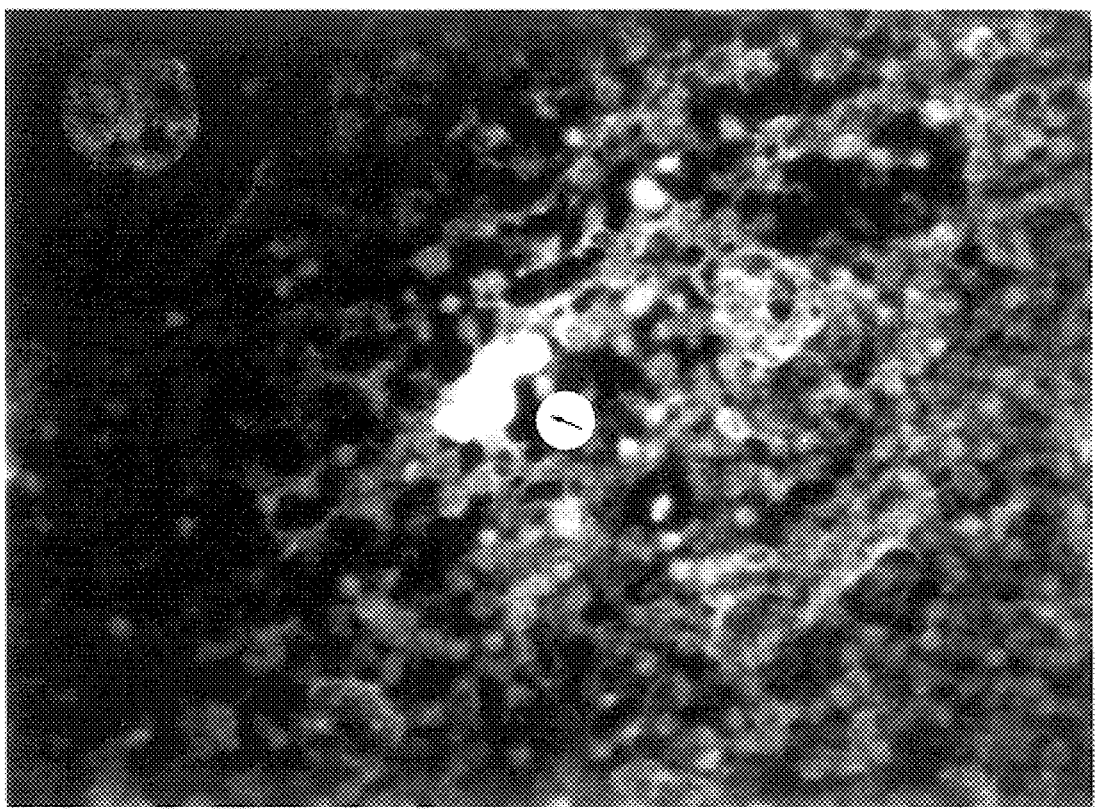
FIG. 34 shows gag positive cells in lymph node tissue from a patient with early HIV-1 infection, after performing in situ PCR using a linear primer and a FRET-labeled hairpin primer of the invention, as described in Section 18, Example 12.

FIG. 34 shows the gag positive cells in lymph node tissue from a patient with early HIV-1 infection, after performing in situ PCR using the linear primer and the FRET-labeled hairpin primer of the invention.

Figure 35:
FIG. 35 shows the same view of the tissue sample as in FIG. 34, at a higher magnification. The gag positive cells show a strong signal and there is low background in the preparation.

FIG. 35 shows the same view of the tissue sample at a higher magnification. The gag positive cells show a strong signal and there is low background in the preparation.

Figure 36:
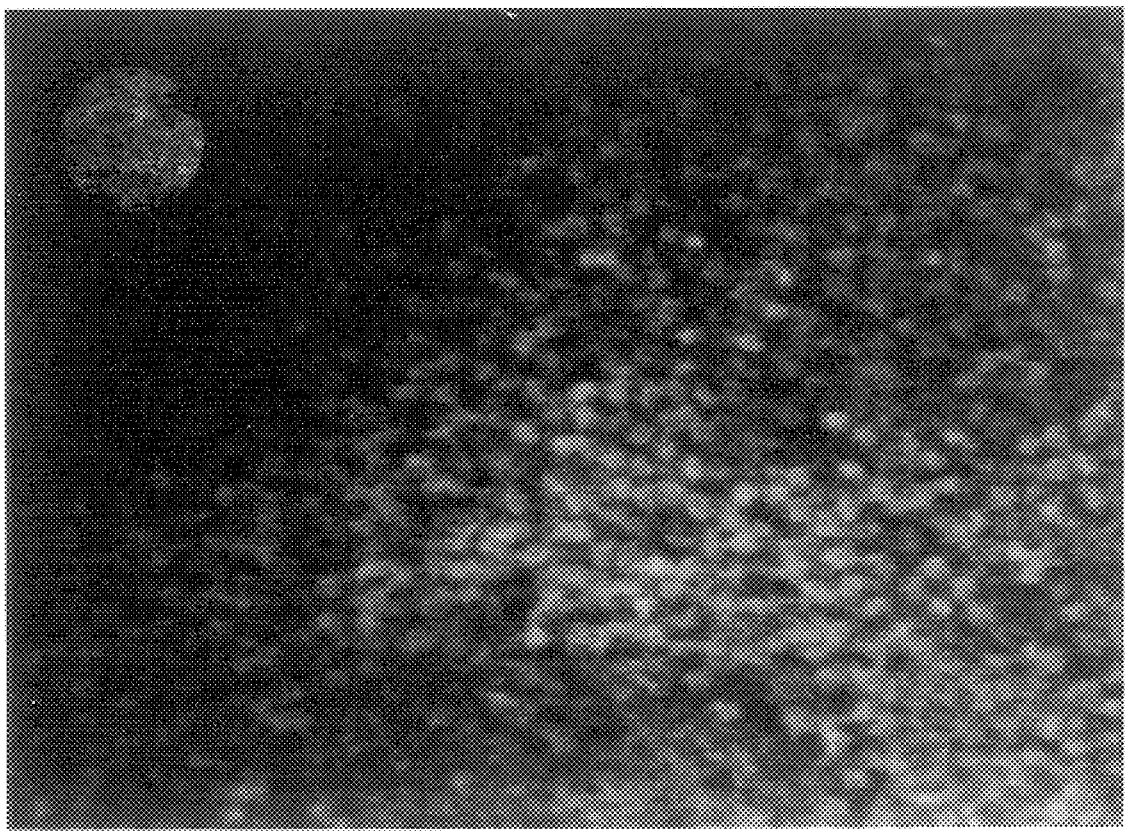
FIG. 36 shows a tissue sample that served as a negative control, in which Taq polymerase was omitted from the amplification cocktail as described in Section 18, Example 12.

FIG. 36 is a negative control in which Taq polymerase was omitted from the amplification cocktail. No gag positive cells were observed.

Figure 37:
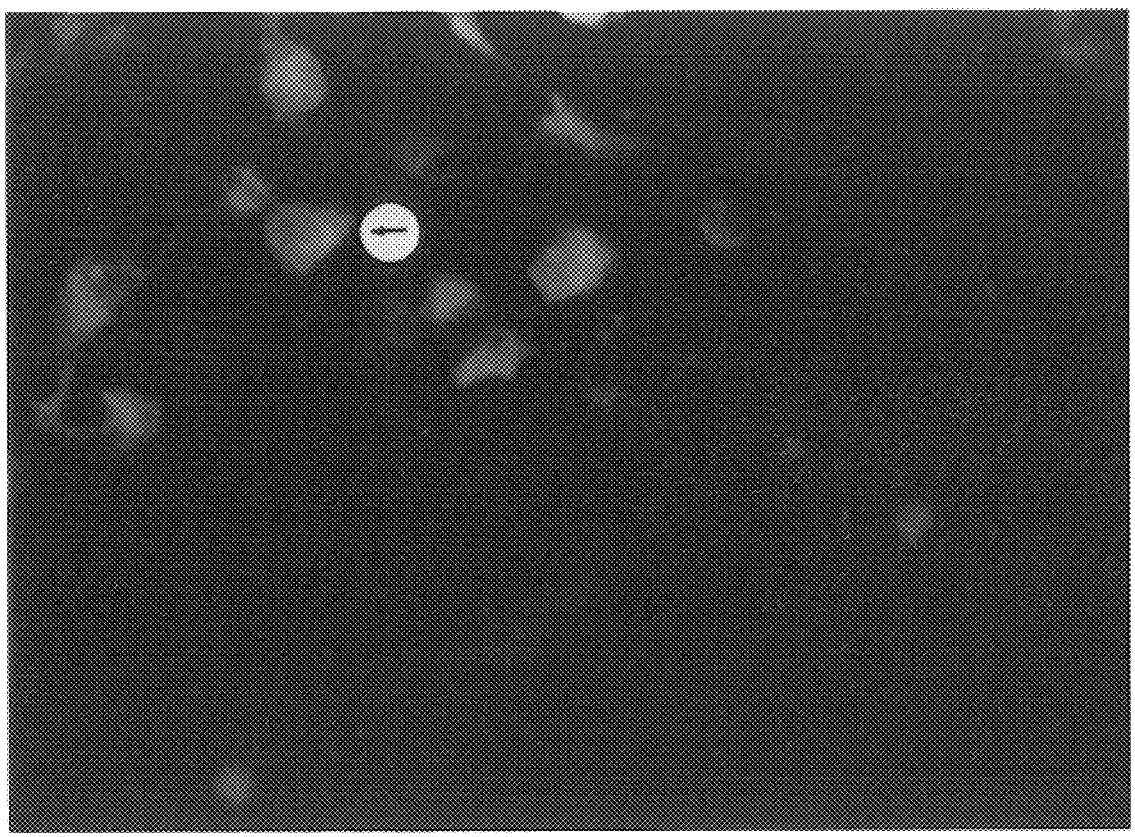
FIG. 37 shows lymph node tissue from an HIV-1 infected patient, after performing in situ PCR using a linear primer and a FRET-labeled hairpin primer, as described in Section 18, Example 12. However the signal-to-background ratio is less than in FIGS. 34 and 35; there is signal in some cells but cytoplasmic background in others due to an inadequate post-PCR wash.

FIG. 37 also shows lymph node tissue from an HIV-1 infected patient after performing in situ PCR using a linear primer and a FRET-labeled hairpin primer. gag positive cells are seen. However the signal-to-background ratio is less than in FIGS. 34 and 35; there is signal in some cells but cytoplasmic background in others due to an inadequate post-PCR wash.

Figure 38:
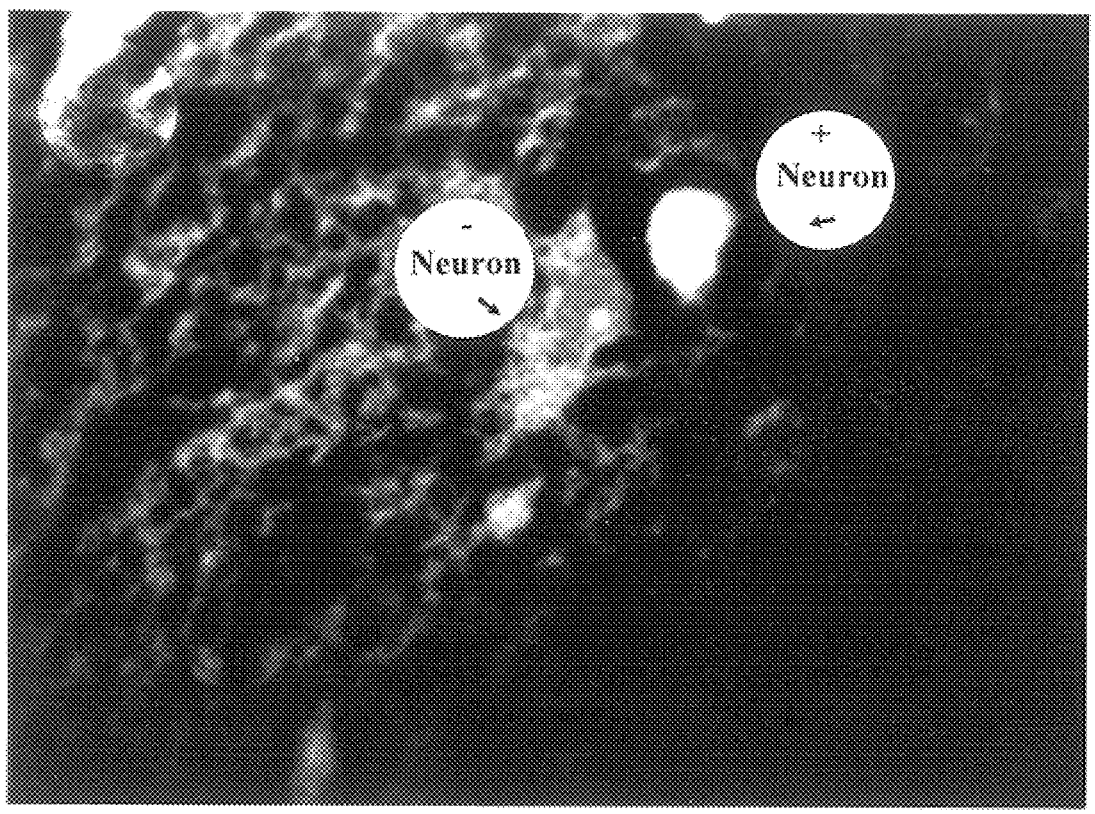
FIG. 38 shows an HIV-1 positive neuron in the cerebrum of a patient who died of AIDS dementia, after performing in situ PCR using a linear primer and a FRET-labeled hairpin primer, as described in Section 18, Example 12. Note the good signal-to-background ratio.

FIG. 38 shows an HIV-1 positive neuron in the cerebrum of a patient who died of AIDS dementia, after performing in situ PCR using a linear primer and a FRET-labeled hairpin primer. Note the good signal-to-background ratio.

18.4. DISCUSSION

Cells from HIV-infected patients, and thus known to be positive for the HIV gag template, showed a fluorescent signal whereas cells expected to be negative for gag showed no signal.

19. EXAMPLE 13

USE OF HAIRPIN PRIMERS IN A CASCADE ROLLING CIRCLE AMPLIFICATION (CRCA) ASSAY 19.1. METHODS AND RESULTS

Cascade rolling circle amplification (CRCA) performed with one hairpin (MET) primer and one non-hairpin primer was used to amplify a "padlock" probe that was circularized by ligation with DNA ligase upon hybridization to a model target sequence (Nilsson, et al., 1994, Science 265:2085–2088), pUC19, and achieved high signal to background ratios and sensitivity down to ~10 template circles. When either rolling circle (forward) hairpin primer 1 or 2 (SEQ ID NOS:46–47) or a reverse hairpin primer 1 or 2 (SEQ ID NOS: 48–49) was labeled with a FAM/DABCYL MET pair (see FIG. 32), normal cascade products were observed, by agarose gel analysis, when using 8 units of Bst DNA polymerase, large fragment in the amplification reaction.

CRCA reactions were run with the following pairs of primers (see FIG. 32): MET-labeled hairpin forward (rolling circle) primer 1 (SEQ ID NO:47) and non-hairpin reverse primer (SEQ ID NO:51); MET-labeled hairpin forward primer 2 (SEQ ID NO:47) and non-hairpin reverse primer (SEQ ID NO:51); non-hairpin forward (rolling circle) primer (SEQ ID NO:50) and MET-labeled hairpin reverse primer 1 (SEQ ID NO:48); and non-hairpin forward (rolling circle) primer (SEQ ID NO:50) and MET-labeled hairpin reverse primer 2 (SEQ ID NO:49).

Several micrograms of double-stranded DNA product were generated, in a 25-μl reaction, in 1 hour at 64° C. Strong MET signals were detected by fluorometric analysis relative to background levels in control reactions (minus ligase). Fluorescent product were also observed by direct visualization of the reaction tubes on a transilluminator.

Figure 33:
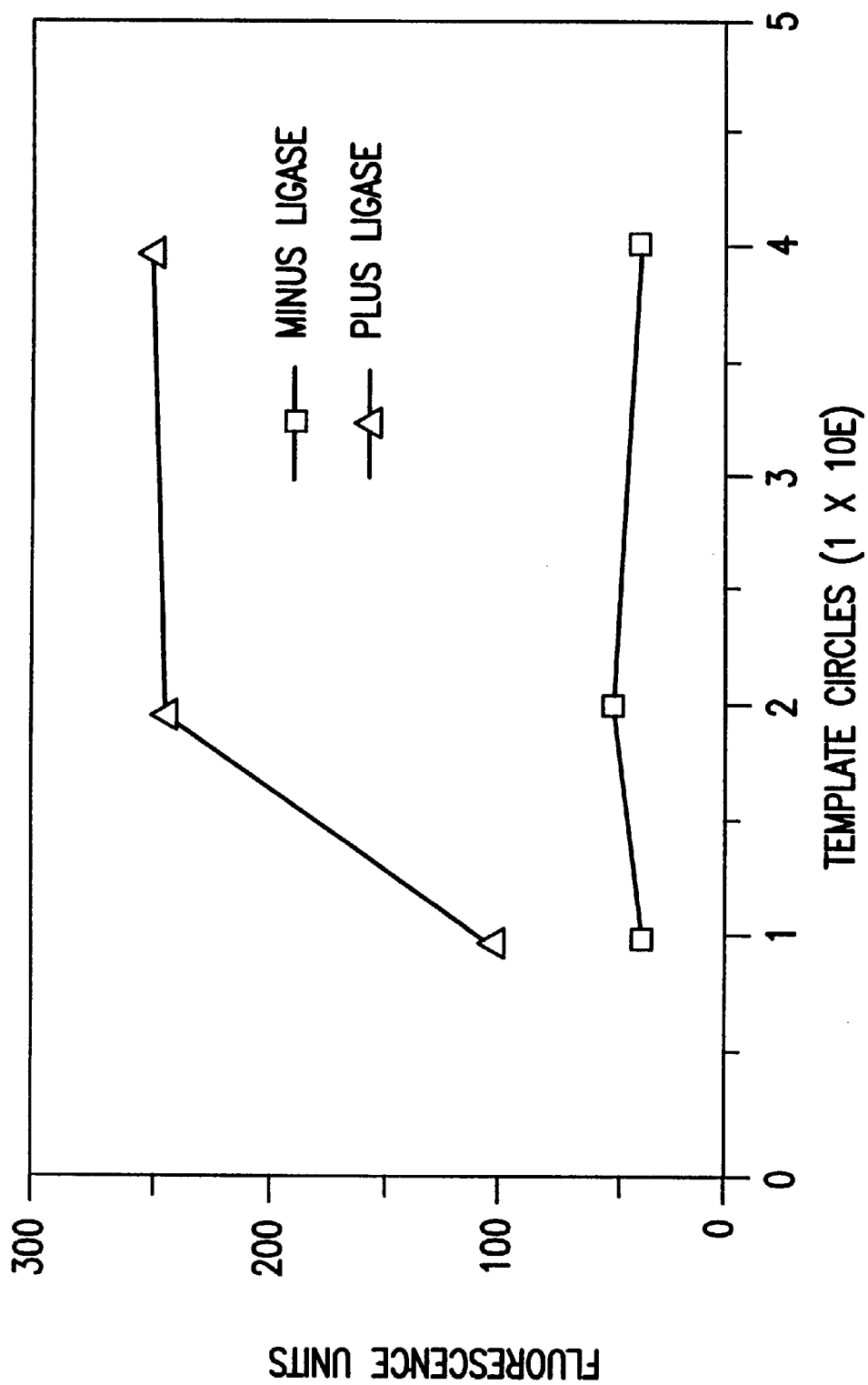

As depicted in FIG. 33, MET signals above background were clearly observed with as few as 10 template circles (+ligase). The CRCA depicted in FIG. 33 was run using unlabeled, non-hairpin forward (rolling circle) primer 1 (SEQ ID NO:46) and MET-labeled hairpin reverse primer 1 (SEQ ID NO:48). Template circles were circularized probe made using pUC19 as target. 8 units of Bst polymerase, large fragment, were used and the CRCA reaction was run for 1 hour at 64° C. Signals from samples were then measured in a spectrofluorometer. Signals remained low at all probe concentrations in the absence of ligase, demonstrating that circularized template is required for CRCA, and that non-specific reactions, where hairpin primers could potentially be incorporated, are suppressed.

Furthermore, the CRCA products were digested with a restriction endonuclease, HaeIII, which cuts only at the ligation junction of the original probe. This digestion yielded double-stranded products that were the unit length size of the probe, demonstrating that the amplified products were true CRCA products.

CRCA was also performed in which the reverse primer was a hairpin primer labeled with a FAM/DABCYL MET pair (either hairpin reverse primer 1 or 2 as shown in FIG. 32), while the forward primer was an unmodified hairpin primer (identical to either forward hairpin primer 1 or 2, as shown in FIG. 32, minus the MET moieties). Similar to the results described above using a hairpin forward primer and a non-hairpin reverse primer, MET signals above background were clearly observed, and normal, low background signals were observed. The use of two hairpin primers may improve specificity and reduce background with other target systems by preventing non-specific interactions between target and/or genomic DNA and the primers.

CRCA using a non-hairpin forward (rolling circle) primer (SEQ ID NO: 50), a MET-labeled hairpin reverse primer 1 (SEQ ID NO:48) and a ras target specific sequence (SEQ ID NO:53), was performed to detect ras mutant and wild-type sequences. Ligation reactions were performed in which the ligation junction contained correct or incorrect basepairs at codon 12 of the ras sequence (SEQ ID NO:53). MET signals were etected when a correctly paired A•T ligation reaction was diluted down to ~$10^4$ input target molecules, while $10^8$ molecules of a mispaired A•G reaction were required for detection, demonstrating about a 10,000-fold discrimination between correct and incorrect basepairs.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of detecting telomerase activity comprising:
   (a) contacting a sample suspected of having telomerase activity with at least two oligonucleotide primers comprising a first primer and a second primer, wherein said first primer comprises the following continuous sequences in 5' to 3' order:
      (i) a first nucleotide sequence of 6-30 nucleotides, wherein a nucleotide within said first nucleotide sequences is labeled with a first moiety selected from the group consisting of a donor moiety and an acceptor moiety of a molecular energy transfer pair, wherein the donor moiety emits energy of one or more particular wavelengths when excited, and the acceptormoiety absorbs energy at one or more particular wavelengths emitted by the donor moiety;
      (ii) a second, single-stranded nucleotide sequence of 3-20 or nucleotides;
      (iii) a third nucleotide sequence of 6-30 nucleotides, wherein a nucleotides within said third nucleotide sequence is labeled with a second moiety selected from the group consisting of said donor moiety and said acceptor moiety, and said second moiety is the member of said group not labeling said first nucleotide sequence, wherein said third nucleotide sequence is sufficiently complementary in reverse order to said first nucleotide sequence for a duplex to form between said first nucleotide sequence and said third nucleotide sequence such that said first moiety and second moiety are in sufficient proximity such that, when the donor moiety is excited and emits energy, the acceptor moiety absorbs energy emitted by the donor moiety; and
      (iv) at the 3' end of said first primer, a fourth, single-stranded nucleotide sequence of 8-40 nucleotides that comprises at its 3' end a sequence that is a substrate for a telomerase; wherein said second primer comprises at its 3' end a sequence sufficiently complementary so as to be able to hybridize to telomeric repeats that result from the activity of said telomerase;
   (b) subjecting the sample to conditions suitable for telomerase activity;
   (c) conducting a nucleic acid amplification reaction under conditions suitable for said first and second primers to prime DNA synthesis;
   (d) stimulating energy emission from said donor moiety; and
   (e) detecting or measuring energy emitted by said donor moiety or acceptor moiety, the presence or amount of said energy indicating the presence or amount of telomerase activity in the sample.

2. A method for determining if a target nucleotide sequence is present in a sample comprising:
   (a) contacting the sample with an oligonucleotide containing:
      (i) a first nucleotide sequence,
      (ii) a second nucleotide sequence at the 5' end of the first nucleotide sequence,
      (iii) a third nucleotide sequence at the 5' end of the second nucleotide sequence, and
      (iv) a fourth nucleotide sequence at the 5' end of the third nucleotide sequence,
         wherein the oligonucleotide is capable of forming a hairpin containing nucleotides of the second and fourth nucleotide sequences, and the oligonucleotide emits a detectable signal if the hairpin is not formed,
   (b) incorporating the oligonucleotide into a double-stranded nucleic acid, and
   (c) determining that the target nucleotide sequence is present in the sample if the signal is detected, or determining that the target nucleotide sequence is not present in the sample if the signal is not detected.

3. The method of claim 2, wherein the first nucleotide sequence contains the nucleotide at the 3' end of the oligonucleotide, the fourth nucleotide sequence contains the nucleotide at the 5' end of the oligonucleotide, and the first nucleotide sequence is not complementary to the fourth nucleotide sequence.

4. The method of claim 3, wherein the first nucleotide sequence is not complementary to the second nucleotide sequence.

5. The method of claim 3, wherein the first nucleotide sequence is not complementary to the third nucleotide sequence.

6. The method of claim 2, wherein the detectable signal emitted by the oligonucleotide if the hairpin is not formed is more intense than a signal emitted by the oligonucleotide if the hairpin is formed.

7. The method of claim 2, wherein the oligonucleotide emits the detectable signal only if the hairpin is not formed.

8. The method of claim 7, wherein the detectable signal is substantial.

9. The method of claim 2, wherein the oligonucleotide further contains a molecular energy transfer pair including an energy donor moiety that is capable of emitting energy, and an energy acceptor moiety that is capable of absorbing an amount of the emitted energy,
wherein the donor moiety is attached to a nucleotide of the second nucleotide sequence and the acceptor moiety is attached to a nucleotide of the fourth nucleotide sequence, or the acceptor moiety is attached to a nucleotide of the second nucleotide sequence and the donor moiety is attached to a nucleotide of the fourth nucleotide sequence; and the acceptor moiety absorbs the amount of the emitted energy only if the hairpin is formed.

10. The method of claim 2, wherein the first nucleotide sequence is complementary to a nucleotide sequence flanking the target nucleotide sequence.

11. The method of claim 10, wherein the target nucleotide sequence is genomic DNA.

12. The method of claim 11, wherein the target nucleotide sequence is cDNA.

13. The method of claim 11, wherein the target nucleotide sequence is mRNA.

14. The method of claim 11, wherein the target nucleotide sequence is chemically synthesized DNA.

15. The method of claim 11, wherein the target nucleotide sequence is a sequence of an infectious disease agent.

16. The method of claim 11, wherein the target nucleotide sequence is a wild-type human genomic sequence, mutation of which is implicated in the presence of a human disease or disorder.

17. The method of claim 11, wherein the target nucleotide sequence is an amplification product.

18. The method of claim 17, wherein the amplification product contains a restriction site.

19. The method of claim 9, wherein the donor moiety is a fluorophore and the acceptor moiety is a quencher of light emitted by the fluorophore.

20. The method of claim 9, wherein the donor moiety is fluorescein.

21. The method of claim 9, wherein the donor moiety is a derivative of fluorescein.

22. The method of claim 9, wherein the donor moiety is 5-carboxyfluorescein.

23. The method of claim 9, wherein the donor moiety is rhodamine.

24. The method of claim 9, wherein the donor moiety is 5-(2'-aminoethyl) aminonapthalene-1-sulfonic acid.

25. The method of claim 9, wherein the donor moiety is anthranilamide.

26. The method of claim 9, wherein the donor moiety is coumarin.

27. The method of claim 9, wherein the donor moiety is a metal chelate.

28. The method of claim 9, wherein the donor moiety is a terbium chelate derivative.

29. The method of claim 9, wherein the donor moiety is Reactive Red 4.

30. The method of claim 9, wherein the acceptor moiety is DABCYL.

31. The method of claim 9, wherein the acceptor moiety is rhodamine.

32. The method of claim 9, wherein the acceptor moiety is pyrene butyrate.

33. The method of claim 9, wherein the acceptor moiety is eosine nitrotyrosine.

34. The method of claim 9, wherein the acceptor moiety is ethidium.

35. The method of claim 9, wherein the acceptor moiety is fluorescein.

36. The method of claim 9, wherein the acceptor moiety is a derivative of fluorescein.

37. The method of claim 9, wherein the acceptor moiety Malachite green.

38. The method of claim 9, wherein the acceptor moiety is Texas Red.

39. The method of claim 9, wherein the donor moiety is fluorescein and the acceptor moiety is DABCYL.

40. The method of claim 9, wherein the donor moiety is a derivative of fluorescein and the acceptor moiety is DABCYL.

41. The method of claim 9, wherein the nucleotide to which the donor moiety is attached is complementary to the nucleotide to which the acceptor moiety is attached.

42. The method of claim 9, wherein, if the hairpin is formed, then the nucleotide to which the donor moiety is attached and the complement of the nucleotide to which the acceptor moiety is attached are five nucleotides apart.

43. The method of claim 9, wherein the nucleotide to which the donor moiety is attached and the nucleotide to which the acceptor moiety is attached are from 15 to 25 nucleotides apart.

44. The method of claim 2 comprising, in between (b) and (c), conducting an amplification reaction, thereby incorporating the oligonucleotide into an amplification product if the target nucleotide sequence is present in the sample.

45. The method of claim 2, wherein the oligonucleotide is incorporated into the double-stranded nucleic acid using a polymerase.

46. The method of claim 44, wherein the amplification reaction is a polymerase chain reaction.

47. The method of claim 44, wherein the amplification reaction is an allele-specific polymerase chain reaction.

48. The method of claim 44, wherein the amplification reaction is a triamplification.

49. The method of claim 44, wherein the amplification reaction is a nucleic acid sequence-based amplification.

50. The method of claim 44, wherein the amplification reaction is a strand displacement amplification.

51. The method of claim 44, wherein the amplification reaction is a telomeric repeat amplification.

52. The method of claim 44, wherein the amplification reaction is a cascade rolling circle amplification.

53. The method of claim 44, wherein the amplification reaction is conducted using an amplification refractory mutation system.

54. The method of claim 44, wherein the amplification reaction is conducted in situ.

55. The method of claim 2 further comprising, prior to (b), contacting the sample with bisulfite to convert unmethylated cytosine residues to uracil residues.

56. The method of claim 2, wherein the oligonucleotide is an oligodeoxynucleotide.

57. The method of claim 2, wherein the first nucleotide sequence contains a restriction endonuclease recognition site.

58. The method of claim 2, wherein the signal is light.

59. A method for detecting a target nucleotide sequence comprising:
   (a) annealing a first oligonucleotide to a nucleotide sequence flanking a target nucleotide sequence, wherein the first oligonucleotide contains:
      (i) a first nucleotide sequence,
      (ii) a second nucleotide sequence at the 5' end of the first nucleotide sequence,
      (iii) a third nucleotide sequence at the 5' end of the second nucleotide sequence, and
      (iv) a fourth nucleotide sequence at the 5' end of the third nucleotide sequence,
         wherein the first oligonucleotide is capable of forming a hairpin containing nucleotides of the second and fourth nucleotide sequences, and the first oligonucleotide emits a detectable signal if the hairpin is not formed,
   (b) extending the 3' end of the first oligonucleotide using the target nucleotide sequence as a template to form an extended first strand, wherein the target nucleotide sequence is annealed to the extended first strand,
   (c) separating the target nucleotide sequence from the extended first strand,
   (d) annealing a second oligonucleotide to the extended first strand,
   (e) extending the 3' end of the second oligonucleotide using the extended first strand as a template to form an extended second strand, wherein the extended first strand is annealed to the extended second strand, and
   (f) detecting the signal to detect the target nucleotide sequence.

60. The method of claim 59, wherein the first nucleotide sequence contains the nucleotide at the 3' end of the oligonucleotide, the fourth nucleotide sequence contains the nucleotide at the 5' end of the oligonucleotide, and the first nucleotide sequence is not complementary to the fourth nucleotide sequence.

61. The method of claim 60, wherein the first nucleotide sequence is not complementary to the second nucleotide sequence.

62. The method of claim 60, wherein the first nucleotide sequence is not complementary to the third nucleotide sequence.

63. The method of claim 59, wherein the detectable signal emitted by the first oligonucleotide if the hairpin is not formed is more intense than a signal emitted by the first oligonucleotide if the hairpin is formed.

64. The method of claim 59, wherein the first oligonucleotide emits the detectable signal only if the hairpin is not formed.

65. The method of claim 64, wherein the detectable signal is substantial.

66. The method of claim 59, comprising, in between (e) and (f), amplifying the extended first and second strands.

67. The method of claim 66, wherein the amplification of the extended first and second strands comprises:
   (i) separating the extended first strand from the extended second strand,
   (ii) annealing the first oligonucleotide to the extended second strand, and annealing the second oligonucleotide to the extended first strand,
   (iii) extending the 3' end of the first oligonucleotide using the extended second strand as a template to form another extended first strand, wherein the extended second strand is annealed to the other extended first strand; and extending the 3' end of the second oligonucleotide using the extended first strand as a template to form another extended second strand, wherein the extended first strand is annealed to the other extended second strand, and
   (iv) repeating (i), (ii), and (iii) for a finite number of times, wherein, in (i), the extended first and second strands respectively are the extended first strand and the other extended second strand of (iii), or respectively are the other extended first strand and the extended second strand of (iii).

68. The method of claim 59, wherein the first oligonucleotide further contains a molecular energy transfer pair including an energy donor moiety that is capable of emitting energy, and an energy acceptor moiety that is capable of absorbing an amount of the emitted energy,
   wherein the donor moiety is attached to a nucleotide of the second nucleotide sequence and the acceptor moiety is attached to a nucleotide of the fourth nucleotide sequence, or the acceptor moiety is attached to a nucleotide of the second nucleotide sequence and the donor moiety is attached to a nucleotide of the fourth nucleotide sequence; and the acceptor moiety absorbs the amount of the emitted energy only if the hairpin is formed.

69. A method for detecting a target nucleotide sequence comprising:
   (a) annealing a first oligonucleotide to a nucleotide sequence flanking a target nucleotide sequence, wherein the first oligonucleotide contains:
      (i) a first nucleotide sequence complementary to the nucleotide sequence flanking the target nucleotide sequence, and
      (ii) a second nucleotide sequence at the 5' end of the first nucleotide sequence,
   (b) extending the 3' end of the first oligonucleotide using the target nucleotide sequence as a template to form an extended first strand, wherein the target nucleotide sequence is annealed to the extended first strand,
   (c) separating the target nucleotide sequence from the extended first strand,
   (d) annealing a second oligonucleotide to the extended first strand,
   (e) extending the 3' end of the second oligonucleotide using the extended first strand as a template to form an extended second strand, wherein the extended first strand is annealed to the extended second strand,
   (f) separating the extended first strand from the extended second strand,
   (g) annealing a third oligonucleotide to the extended second strand, wherein the third oligonucleotide contains:
      (i) a third nucleotide sequence,
      (ii) a fourth nucleotide sequence at the 5' end of the third nucleotide sequence,
      (iii) a fifth nucleotide sequence at the 5' end of the fourth nucleotide sequence, and
      (iv) a sixth nucleotide sequence at the 5' end of the fifth nucleotide sequence,
         wherein the third nucleotide sequence is complementary to the complement of the second nucleotide sequence, the third oligonucleotide is capable of forming a hairpin containing nucleotides of the fourth and sixth nucleotide sequences, and the third oligonucleotide emits a detectable signal if the hairpin is not formed, (h) extending the 3' end of the third oligonucleotide using the extended second strand as a template to form a doubly extended first strand, wherein the doubly extended first strand is annealed to the extended second strand, (i) separating the doubly extended first strand from the extended second strand, (j) annealing the second oligonucleotide to the doubly extended first strand, (k) extending the 3' end of the second oligonucleotide using the doubly extended first strand as a template to form a doubly extended second strand, wherein the doubly extended first strand is annealed to the doubly extended second strand, and (l) detecting the signal to detect the target nucleotide sequence.

70. The method of claim 69, wherein the third nucleotide sequence contains the nucleotide at the 3' end of the oligonucleotide, the sixth nucleotide sequence contains the nucleotide at the 5' end of the oligonucleotide, and the third nucleotide sequence is not complementary to the sixth nucleotide sequence.

71. The method of claim 70, wherein the third nucleotide sequence is not complementary to the fourth nucleotide sequence.

72. The method of claim 70, wherein the third nucleotide sequence is not complementary to the fifth nucleotide sequence.

73. The method of claim 69, wherein the detectable signal emitted by the third oligonucleotide if the hairpin is not formed is more intense than a signal emitted by the third oligonucleotide if the hairpin is formed.

74. The method of claim 69, wherein the third oligonucleotide emits the detectable signal only if the hairpin is not formed.

75. The method of claim 74, wherein the detectable signal is substantial.

76. The method of claim 69 comprising, in between (k) and (l), amplifying the doubly extended first and second strands.

77. The method of claim 76, wherein the amplification of the doubly extended first and second strands comprises:

(i) separating the doubly extended first strand from the doubly extended second strand, (ii) annealing the second oligonucleotide to the doubly extended first strand, and annealing the third oligonucleotide to the doubly extended second strand, (iii) extending the 3' end of the second oligonucleotide using the doubly extended first strand as a template to form another doubly extended second strand, wherein the doubly extended first strand is annealed to the other doubly extended second strand; and extending the 3' end of the third oligonucleotide using the doubly extended second strand as a template to form another doubly extended first strand, wherein the doubly extended second strand is annealed to the other doubly extended first strand, and (iv) repeating (i), (ii), and (iii) for a finite number of times, wherein, in (i), the doubly extended first and second strands respectively are the doubly extended first strand and the other doubly extended second strand of (iii), or respectively are the other doubly extended first strand and the doubly extended second strand of (iii).

78. The method of claim 69, wherein the third oligonucleotide further contains a molecular energy transfer pair including an energy donor moiety that is capable of emitting energy, and an energy acceptor moiety that is capable of absorbing an amount of the emitted energy, wherein the donor moiety is attached to a nucleotide of the fourth nucleotide sequence and the acceptor moiety is attached to a nucleotide of the sixth nucleotide sequence, or the acceptor moiety is attached to a nucleotide of the fourth nucleotide sequence and the donor moiety is attached to a nucleotide of the sixth nucleotide sequence; and the acceptor moiety absorbs the amount of the emitted energy only if the hairpin is formed.

79. A method for detecting a target nucleotide sequence comprising:

(a) annealing a first oligonucleotide to a nucleotide sequence flanking a target nucleotide sequence, wherein the first oligonucleotide contains:

(i) a first nucleotide sequence complementary to the nucleotide sequence flanking the target nucleotide sequence, and (ii) a second nucleotide sequence at the 5' end of the first nucleotide sequence, (b) extending the 3' end of the first oligonucleotide using the target nucleotide sequence as a template to form an extended first strand, wherein the target nucleotide sequence is annealed to the extended first strand, (c) separating the target nucleotide sequence from the extended first strand, (d) annealing a second oligonucleotide to a nucleotide sequence of the extended first strand, wherein the second oligonucleotide contains:

(i) a third nucleotide sequence complementary to the sequence of the extended first strand, and (ii) a fourth nucleotide sequence at the 5' end of the third nucleotide sequence, (e) extending the 3' end of the second oligonucleotide using the extended first strand as a template to form an extended second strand, wherein the extended first strand is annealed to the extended second strand, (f) separating the extended first strand from the extended second strand, (g) annealing a third oligonucleotide to the extended second strand, wherein the third oligonucleotide contains:

(i) a fifth nucleotide sequence, (ii) a sixth nucleotide sequence at the 5' end of the fifth nucleotide sequence, (iii) a seventh nucleotide sequence at the 5' end of the sixth nucleotide sequence, and (iv) an eighth nucleotide sequence at the 5' end of the seventh nucleotide sequence, wherein the fifth nucleotide sequence is complementary to the complement of the second nucleotide sequence, the fifth nucleotide sequence is not complementary to the eighth nucleotide sequence, the third oligonucleotide is capable of forming a first hairpin containing nucleotides of the sixth and eighth nucleotide sequences, and the third oligonucleotide emits a first detectable signal if the first hairpin is not formed, (h) extending the 3' end of the third oligonucleotide using the extended second strand as a template to form a doubly extended first strand, wherein the doubly extended first strand is annealed to the extended second strand, (i) separating the doubly extended first strand from the extended second strand, (j) annealing a fourth oligonucleotide to the doubly extended first strand, wherein the fourth oligonucleotide contains:

(i) a ninth nucleotide sequence, (ii) a tenth nucleotide sequence at the 5' end of the ninth nucleotide sequence, (iii) an eleventh nucleotide sequence at the 5' end of the tenth nucleotide sequence, and (iv) a twelfth nucleotide sequence at the 5' end of the eleventh nucleotide sequence, wherein the ninth nucleotide sequence is complementary to the complement of the fourth nucleotide sequence, the ninth nucleotide sequence is not complementary to the twelfth nucleotide sequence, the fourth oligonucleotide is capable of forming a second hairpin containing nucleotides of the tenth and twelfth nucleotide sequences, and the fourth oligonucleotide emits a second detectable signal if the second hairpin is not formed, (k) extending the 3' end of the fourth oligonucleotide using the doubly extended first strand as a template to form a doubly extended second strand, and extending the 3' end of the doubly extended first strand using the fourth oligonucleotide as a template to form a triply extended first strand, wherein the doubly extended second strand is annealed to the triply extended first strand, and (l) detecting the first or second signal to detect the target nucleotide sequence.

80. The method of claim 79, wherein the fifth nucleotide sequence contains the nucleotide at the 3' end of the third oligonucleotide, the eighth nucleotide sequence contains the nucleotide at the 5' end of the third oligonucleotide, and the fifth nucleotide sequence is not complementary to the eighth nucleotide sequence.

81. The method of claim 80, wherein the fifth nucleotide sequence is not complementary to the sixth nucleotide sequence.

82. The method of claim 80, wherein the fifth nucleotide sequence is not complementary to the seventh nucleotide sequence.

83. The method of claim 79, wherein the ninth nucleotide sequence contains the nucleotide at the 3' end of the fourth oligonucleotide, the twelfth nucleotide sequence contains the nucleotide at the 5' end of the fourth oligonucleotide, and the ninth nucleotide sequence is not complementary to the twelfth nucleotide sequence.

84. The method of claim 83, wherein the ninth nucleotide sequence is not complementary to the tenth nucleotide sequence.

85. The method of claim 83, wherein the ninth nucleotide sequence is not complementary to the eleventh nucleotide sequence.

86. The method of claim 79, wherein the first detectable signal emitted by the third oligonucleotide if the first hairpin is not formed is more intense than a signal emitted by the third oligonucleotide if the first hairpin is formed.

87. The method of claim 79, wherein the third oligonucleotide emits the first detectable signal only if the first hairpin is not formed.

88. The method of claim 87, wherein the first detectable signal is substantial.

89. The method of claim 79, wherein the second detectable signal emitted by the fourth oligonucleotide if the second hairpin is not formed is more intense than a signal emitted by the fourth oligonucleotide if the second hairpin is formed.

90. The method of claim 79, wherein the fourth oligonucleotide emits the second detectable signal only if the second hairpin is not formed.

91. The method of claim 90, wherein the second detectable signal is substantial.

92. The method of claim 79, wherein the complete nucleotide sequences of the third and fourth oligonucleotides are identical.

93. The method of claim 79, wherein the second and fourth nucleotide sequences are identical.

94. The method of claim 79 comprising, in between (k) and (l), amplifying the doubly extended second strand and the triply extended first strand.

95. The method of claim 94, wherein the amplification of the doubly extended first and second strands comprises:

(i) separating the doubly extended second strand from the triply extended first strand, (ii) annealing the third oligonucleotide to the doubly extended second strand, and annealing the fourth oligonucleotide to the triply extended first strand, (iii) extending the 3' end of the third oligonucleotide using the doubly extended second strand as a template to form another triply extended first strand, wherein the doubly extended second strand is annealed to the other triply extended first strand; and extending the 3' end of the fourth oligonucleotide using the triply extended first strand as a template to form another doubly extended second strand, wherein the triply extended first strand is annealed to the other doubly extended second strand, and (iv) repeating (i), (ii), and (iii) for a finite number of times, wherein, in (i), the doubly extended second strand is the doubly extended second strand of (iii) and the triply extended first strand is the other triply extended first strand of (iii), or the doubly extended second strand is the other doubly extended second strand of (iii) and the triply extended first strand is the triply extended first strand of (iii).

96. The method of claim 79, wherein the third oligonucleotide further contains a molecular energy transfer pair including an energy donor moiety that is capable of emitting energy, and an energy acceptor moiety that is capable of absorbing an amount of the emitted energy, wherein the donor moiety is attached to a nucleotide of the sixth nucleotide sequence and the acceptor moiety is attached to a nucleotide of the eighth nucleotide sequence, or the acceptor moiety is attached to a nucleotide of the sixth nucleotide sequence and the donor moiety is attached to a nucleotide of the eighth nucleotide sequence; and the acceptor moiety absorbs the amount of the emitted energy only if the hairpin is formed.

97. The method of claim 79, wherein the fourth oligonucleotide further contains a molecular energy transfer pair including an energy donor moiety that is capable of emitting energy, and an energy acceptor moiety that is capable of absorbing an amount of the emitted energy, wherein the donor moiety is attached to a nucleotide of the tenth nucleotide sequence and the acceptor moiety is attached to a nucleotide of the twelfth nucleotide sequence, or the acceptor moiety is attached to a nucleotide of the tenth nucleotide sequence and the donor moiety is attached to a nucleotide of the twelfth nucleotide sequence; and the acceptor moiety absorbs the amount of the emitted energy only if the hairpin is formed.

98. A method for determining if a target nucleotide sequence is present in a sample comprising:
  (a) contacting the sample with first and second oligonucleotides, wherein the first oligonucleotide is capable of annealing to the second oligonucleotide to form a duplex, and the first or second oligonucleotide emits a detectable signal if the duplex is not formed,
  (b) incorporating the first or second oligonucleotide into a double-stranded nucleic acid using a polymerase if the target nucleotide sequence is present in the sample, thereby preventing the first and second nucleotides from forming the duplex, and
  (c) determining that the target nucleotide sequence is present in the sample if the signal is detected, or determining that the target nucleotide sequence is not present in the sample if the signal is not detected.

99. The method of claim 98, wherein the detectable signal emitted by the first or second oligonucleotide if the first oligonucleotide is not annealed to the second oligonucleotide is more intense than a signal emitted by the first or second oligonucleotide if the first oligonucleotide is annealed to the second oligonucleotide.

100. The method of claim 98, wherein the first or second oligonucleotide emits the detectable signal only if the first oligonucleotide is not annealed to the second oligonucleotide.

101. The method of claim 100, wherein the detectable signal is substantial.

102. The method of claim 98, wherein the first and second oligonucleotides contain a molecular energy transfer pair including an energy donor moiety that is capable of emitting energy, and an energy acceptor moiety that is capable of absorbing an amount of the emitted energy,
  wherein the donor moiety is attached to a nucleotide of the first oligonucleotide and the acceptor moiety is attached to a nucleotide of the second oligonucleotide, or the acceptor moiety is attached to a nucleotide of the first oligonucleotide and the donor moiety is attached to a nucleotide of the second oligonucleotide, and the acceptor moiety absorbs the amount of energy only if the duplex is formed.

103. The method of claim 98 comprising, in between (b) and (c), conducting an amplification reaction, thereby incorporating the first or second oligonucleotide into an amplification product if the target nucleotide sequence is present in the sample.

* * * * *